(12) United States Patent
Borodic

(10) Patent No.: US 11,096,993 B2
(45) Date of Patent: *Aug. 24, 2021

(54) METHOD OF TREATING MACULAR DEGENERATION USING BOTULINUM TOXIN-BASED PHARMACEUTICALS

(71) Applicant: Gary E. Borodic, Canton, MA (US)

(72) Inventor: Gary E. Borodic, Canton, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/015,984

(22) Filed: Jun. 22, 2018

(65) Prior Publication Data

US 2018/0303917 A1     Oct. 25, 2018

Related U.S. Application Data

(63) Continuation-in-part of application No. 15/834,491, filed on Dec. 7, 2017.
(Continued)

(51) Int. Cl.
*A61P 27/02*     (2006.01)
*A61K 38/18*     (2006.01)
(Continued)

(52) U.S. Cl.
CPC .......... *A61K 38/4893* (2013.01); *A61B 3/102* (2013.01); *A61B 3/1233* (2013.01);
(Continued)

(58) Field of Classification Search
None
See application file for complete search history.

(56) References Cited

U.S. PATENT DOCUMENTS 6,428,189 B1   8/2002  Borodic
7,146,209 B2  12/2006  Gross et al.
(Continued)

FOREIGN PATENT DOCUMENTS

WO      2018107005 A1   6/2018

OTHER PUBLICATIONS

Nickla et al., The Multifunctional Choroid. Prog Retin Eye Res. Mar. 2010; 29(2): 144-168. (Year: 2010).*
(Continued)

*Primary Examiner* — Aurora M Fontainhas
(74) *Attorney, Agent, or Firm* — Hayes Soloway PC

(57) ABSTRACT

Formulations and methods of treatment are disclosed for prevention and/or treatment of visual loss from age-related macular degeneration. The disclosed formulations include botulinum neurotoxin. The disclosed formulations may be applied to an intraocular or extraocular region of a patient. If applied to an extra ocular region of a patient, the botulinum-based pharmaceutical formulation may then be transported to the intra-ocular region of the patient, allowing the active ingredient(s) to penetrate into the choroid, neuroretina, and/or retinal pigment epithelium without direct injection into the eye, eliminating risk of retinal detachment, retinal break, retinal hemorrhage, and blindness. The methods described herein allow for increased blood flow to the choroid, which improves removal of metabolites and intra retinal fluid and also serves to arrest, reverse and/or delay early and later stages of age-related macular degeneration.

18 Claims, 15 Drawing Sheets

Related U.S. Application Data

(60) Provisional application No. 62/533,961, filed on Jul. 18, 2017, provisional application No. 62/449,914, filed on Jan. 24, 2017, provisional application No. 62/431,512, filed on Dec. 8, 2016.

(51) Int. Cl.
*C07K 16/22* (2006.01)
*C07K 14/515* (2006.01)
*A61K 38/48* (2006.01)
*A61B 3/12* (2006.01)
*A61B 3/10* (2006.01)

(52) U.S. Cl.
CPC ............ *A61B 3/1241* (2013.01); *A61P 27/02* (2018.01); *C12Y 304/24069* (2013.01)

(56) References Cited

U.S. PATENT DOCUMENTS

| | | |
|---|---|---|
| 7,465,458 B2 | 12/2008 | First |
| 7,537,773 B1 | 5/2009 | Borodic |
| 7,691,394 B2 | 4/2010 | Borodic |
| 8,277,830 B2 | 10/2012 | de Juan, Jr. et al. |
| 8,642,067 B2 | 2/2014 | Trogden et al. |
| 8,846,622 B2 | 9/2014 | Blumenfeld |
| 2004/0028703 A1 | 2/2004 | Bigalke et al. |
| 2004/0058313 A1 | 3/2004 | Abreu |
| 2004/0170665 A1 | 9/2004 | Donovan |
| 2004/0177387 A1 | 9/2004 | Jayakrishna |
| 2004/0234532 A1 | 11/2004 | First |
| 2007/0059336 A1 | 3/2007 | Hughes et al. |
| 2011/0077229 A1 | 3/2011 | Edelman et al. |
| 2014/0105883 A1* | 4/2014 | Borodic ......... C12Y 304/24069 424/94.67 |
| 2016/0051645 A1 | 2/2016 | Borodic et al. |
| 2016/0278627 A1* | 9/2016 | Huang ................. A61B 3/0025 |

OTHER PUBLICATIONS

Gregori; "Spectral Domain Optical Coherence Tomography Imaging of Drusen in Nonexudative Age-Related Macular Degeneration"; Ophthalmology 2011; 118; 1373-1379; 2011.
Natoli et al.; "Retinal Macrophages Synthesize C3 and Activate Complement in AMD and in Models of Focal Retinal Degeneration"; Retinal Cell Biology; 2017; p. 2977-2990; vol. 58; No. 7.
Wong et al.; "Global prevalence of age-related macular degeneration and disease burden projection for 2020 and 2040: a systematic review and meta-analysis"; Lancet Glob Health; Feb. 2014; p. e106-e116; vol. 2.
Ferrara; "Investigating the choriocapillaris and choroidal vasculature with new optical coherence tomography technologies"; Progress in Retinal and Eye Research; 2016; p. 130-155; vol. 52; Elsevier.
American Academy of Ophthalmology "Risk Factors Associated with Age-Related Macular Degeneration" Ophthalmology; Dec. 2000; p. 2224-2232; vol. 107, No. 12; Elsevier Science Inc.
Hageman et al.; "A common haplotype in the complement regulatory gene factor H (HF1/CFH) predisposes individuals to age-related macular degeneration"; PNAS; May 17, 2005; p. 7227-7232; vol. 102 No. 20; The National Academy of Sciences of the USA.
Hanus et al.; "Current Therapeutic Development for Atrophic Age-related Macular Degeneration"; Br J Ophthalmol; Jan. 2016; p. 122-127; 100(1).
Doyle; "IL-18 Attenuates Experimental Choroidal Neovascularization as a Potential Therapy for Wet Age-Related Macular Degeneration"; Science Translational Medicine; Apr. 2, 2014; p. 1-10; vol. 6 Issue 230; American Association for the Advancement of Science.
Holz et al.; "Efficacy and Safety of Lampalizumab for Geographic Atrophy Due to Age-Related Macular Degeneration: Chroma and Spectri Phase 3 Randomized Clinical Trials"; JAMA Ophthalmol.; Jun. 1, 2018; p. 666-677; 136(6).

Li et al; "Preliminary in vitro and in vivo assessment of a new targeted inhibitor for choroidal neovascularization in age-related macular degeneration"; Drug Design, Development and Therapy; 2016; p. 3415-3423; Dovepress.
Miller; "Beyond VEGF—The Weisenfeld Lecture; Investigative Ophthalmology & Visual Science"; Dec. 2016; p. 6911-6918; vol. 57 No. 15.
Lu; "Profile of conbercept in the treatment of neovascular age-related macular degeneration" Drug Design, Development and Therapy; 2015; p. 2311-2320; 9; Dovepress.
Miller et al.; "Advances in Age-related Macular Degeneration Understanding and Therapy"; US Ophthalmic Rev.; 2017; p. 119-130; 10(2).
Lashkari et al.; "A monoclonal antibody targeting amyloid B (AB) restores complement factor I bioactivity: Potential implications in age-related macular degeneration and Alzheimer's disease"; PLOS ONE; May 21, 2018; p. 1-19; 13(5).
Choi et al.; "Ultrahigh-Speed, Swept-Source Optical Coherence Tomography Angiography in Nonexudative Age-Related Macular Degeneration with Geographic Atrophy"; Ophthalmology; Dec. 2015; p. 2532-2544; vol. 122 No. 12; Elsevier Inc.
Tosi et al.; "CD93 as a Potential Target in Neovascular Age-Related Macular Degeneration"; J Cell Physiol.; Jul. 2017; p. 1767-1773; 232(7); Wiley Periodicals, Inc.
Ren et al.; "IBI302, a promising candidate for AMD treatment, targeting both the VEGF and complement system with high binding affinity in vitro and effective targeting of the ocular tissue in healthy rhesus monkeys"; Exp. Eye Res.; Apr. 2016; p. 352-358; 145; Elsevier.
"Highlights of Prescribing Information"; Medication Guide; Revised Jan. 2016; p. 4-42.
"Highlights of Prescribing Information"; Revised May 2018; 41 pages.
"Important Safety Information"; 2016; 2 pages; Allergan.
The CATT Research Group; "Ranibizumab and Bevacizumab for Neovascular Age-Related Macular Degeneration"; The New England Journal of Medicine; May 19, 2011; p. 1897-1908; vol. 364 No. 20; Massachusetts Medical Society.
Borodic GE et al.; "Clinical and Scientific Aspects of Botulinum A Toxin"; Neuro-ophthalmology; Sep. 1991; vol. 4, No. 3; Ophthalmology Clinics of North America.
Frevert et al; Complexing proteins in botulinum toxin type A drugs: a help or a hindrance; Biologics: Targets & Therapy; 2010; p. 325-332; Dove Medical Press Ltd.
Schantz et al.; "Preparation and Characterization of Botulinum Toxin Type A for Human Treatment"; p. 41-47.
Flynn; "Periocular Botulinum Toxin"; Clinics in Dermatology; 2003; p. 498-504; 21; Elsevier.
DasGupta, "Structures of Botulinum Neurotoxin, Its Functional Domains, and Perspectives on Crystalline Type A Toxin", University of Wisconsin, Madison, WI, 13 pages.
Chakravarthy et al.; "Alternative treatments to inhibit VEGF in age-related choroidal neovascularisation: 2-year findings of the IVAN randomised controlled trial"; Lancet; Oct. 12, 2013; p. 1258-1267; vol. 382.
Danis et al.; "Geographic atrophy in patients with advanced dry age-related macular degeneration:current challenges and future prospects"; Clinical Ophthalmology; 2015; p. 2159-2174; 9; Dovepress.
Gemenetzi et al.; "Risk of geographic atrophy in age-related macular degeneration patients treated with intravitreal anti-VEGF agents"; Eye; 2017; p. 1-9; 31; Macmillan Publishers Limited.
Grunwald et al.; "Growth of Geographic Atrophy in the Comparison of Age-related Macular Degeneration Treatments Trials (CATT)"; Ophthalmology; Apr. 2015; p. 809-816; 122(4).
Grunwald et al.; "Risk of Geographic Atrophy in the Comparison of Age-related Macular Degeneration Treatments Trials"; Ophthalmology; Jan. 2014; p. 150-161/e34; vol. 121, No. 1; Elsevier Inc.
Kurihara et al.; "Targeted deletion of Vegfa in adult mice induces vision loss"; The Journal of Clinical Investigation; 2012; p. 4213-4217; 122(11); http://www.jci.org.
Lois et al.; "Retinal Pigment Epithelial Atrophy in Patients With Exudative Age-Related Macular Degeneration Undergoing Anti-Vascular Endothelial Growth Factor Therapy" Retina, The Journal

(56) References Cited

OTHER PUBLICATIONS of Retinal and Vitreous Diseases; 2013; p. 13-22; vol. 33, No. 1; Ophthalmic Communications Society, Inc.

Martin et al.; "Ranibizumab and Bevacizumab for Treatment of Neovascular Age-Related Macular Degeneration: 2-Year Results"; Ophthalmology; 2012; p. 1388-1398; 119(7); Elsevier Inc.

Rosenfeld et al.; "Characteristics of Patients Losing Vision after 2 Years of Monthly Dosing in the Phase III Ranibizumab Clinical Trials"; Ophthalmology; Mar. 2011; p. 523-530; vol. 118, No. 3; Elsevier Inc.

Saint-Geniez et al.; Role of Cell and Matrix-Bound VEGF Isoforms in Lens Development; Investigative Ophthalmology & Visual Science; Jan. 2009; p. 311-321; vol. 50, No. 1.

Young et al.; "Exacerbation of Choroidal and Retinal Pigment Epithelial Atrophy After Anti-Vascular Endothelial Growth Factor Treatment in Neovascular Age-Related Macular Degeneration"; Retina, The Journal of Retinal and Vitreous Diseases; 2014; p. 1308-1314; vol. 34, No. 7.

Kaszubski et al.; "Geographic Atrophy and Choroidal Neovascularization in the Same Eye: A Review"; Ophthalmic Res.; 2016; p. 185-193; 55(4).

Grunwald et al.; Incidence and Growth of Geographic Atrophy During 5 Years of Comparison of Age-related Macular Degeneration Treatments Trials (CATT); Ophthalmology; Jan. 2017; p. 97-104; 124(1).

Thavikulwat et al.; "Evolution of Geographic Atrophy in Participants Treated with Ranibizumab for Neovascular Age-related Macular Degeneration"; Ophthalmol Retina; 2017; p. 34-41; 1(1).

Abdelfattah et al.; "Progression of Macular Atrophy in Patients With Neovascular Age-Related Macular Degeneration Undergoing Antivascular Endothelial Growth Factor Therapy"; etina; Oct. 2016; p. 1843-1850.

Kaynak et al.;"Is There a Relationship Between Use of Anti-Vascular Endothelial Growth Factor Agents and Atrophic Changes in Age-Related Macular Degeneration Patients";Turk J. Ophthalmol; 2018; p. 81-84; 48; Galenos Publishing Home.

Bhutto et al.;"Increased choroidal mast cells and their degranulation in age-related macular degeneration"; Br. J. Ophthalmol.; May 2016; p. 720-726; 100(5).

Nagasaka et al.; "Effect of low-voltage electrical stimulation on angiogenic growth factors in ischaemic rat skeletal muscle"; Clin Exp Pharmacol Physiol.; Jul. 2006; p. 623-627; 33(7).

Zhao et al.; "Electrical stimulation directly induces pre-angiogenic responses in vascular endothelial cells by signaling through VEGF receptors"; J. Cell Sci.; Jan. 26, 2004; p. 397-405; 117(Pt. 3).

Alhelal et al.; "Trigeminal nerve stimulation triggers oral mast cell activation and vascular permeability"; Annals of Allergy, Asthma, and Immunology; Jan. 2014; pp. 40-45; vol. 112, Issue 1.

Singer; "Advances in the management of macular degeneration"; F1000Prime Reports; May 6, 2014; p. 1-5; 6:29.

Boyd, "What is Macular Degeneration?", American Academy of Opthalmology, Eye Health, May 17, 2018, 4 pgs.

Bhutto; "Understanding age-related macular degeneration (AMD): Relationships between the photoreceptor/retinal pigment epithelium/Bruch's membrane/choriocapillaris complex"; Mol. Aspects Med.; 2012; pp. 295-317; 33(4); Elsevier Ltd.

Haustein et al.; "The effect of acetazolamide on different ocular vascular beds"; Graefes Arch Clin Exp Ophthalmol; 2013; p. 1389-1398; 251; Springer-Verlag.

McLeod et al.;"Relationship between RPE and choriocapillaris in age-related macular degeneration"; Invest. Ophthalmol Vis Sci.; Oct. 2009; p. 4982-4991; 50(10).

Polak;"Effects of Insulin on Retinal and Pulsatile Choroidal Blood Flow in Humans"; Arch Ophthalmol; Jan. 2000; pp. 55-59; vol. 118.

Ma; "Combination of antiangiogenesis with chemotherapy for more effective cancer treatment"; Molecular Cancer Therapeutics; Dec. 2008; p. 3670-3684; 7(12); American Association for Cancer Research.

Claudia Verderio, "Entering Neurons: Botulinum Toxins and Synaptic Vesicle Recycling", Journal, 2006, 995-999, vol. 7, No. 10, European Molecular Biological Organization Reports.

Anna Steinberg, "Expression of Messenger Molecules and Receptors in Rat and Human Sphenopalatine Ganglion Indicating Therapeutic Targets", Journal, 2016, 1-8, vol. 17, The Journal of Headache and Pain.

E. Habermann, "I-Labeled Neurotoxin from Clostridium Botulinum A: Preparation, Binding to Synaptosomes and Ascent to the Spinal Cord", Journal, 1974, 47-56, vol. 281, Naunyn-Schmiedeberg's Archives of Pharmacology.

Sadda et al., "Anti-Vascular Endothelial Growth Factor Use and Atrophy in Neovascular Age-Related Macular Degeneration", Elsevier, Inc., American Academy of Ophthalmology, vol. 127, Issue 5, May 2020, pp. 648-659.

\* cited by examiner

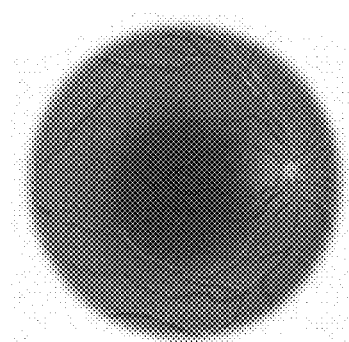 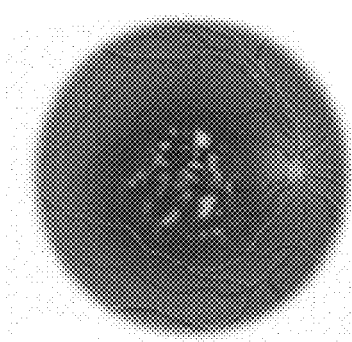 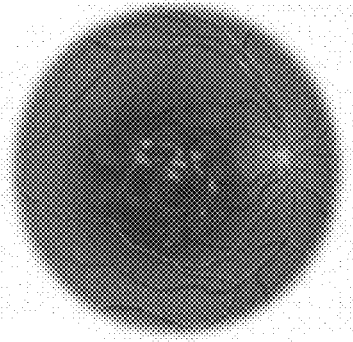
FIG. 1A          FIG. 1B          FIG. 1C
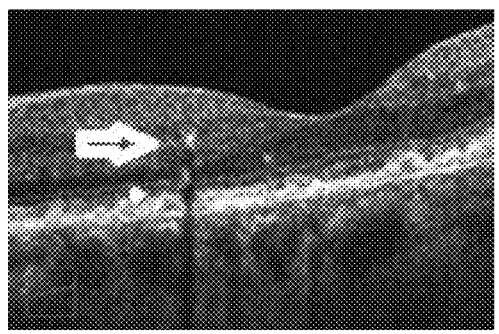
FIG. 1D
FIG. 2

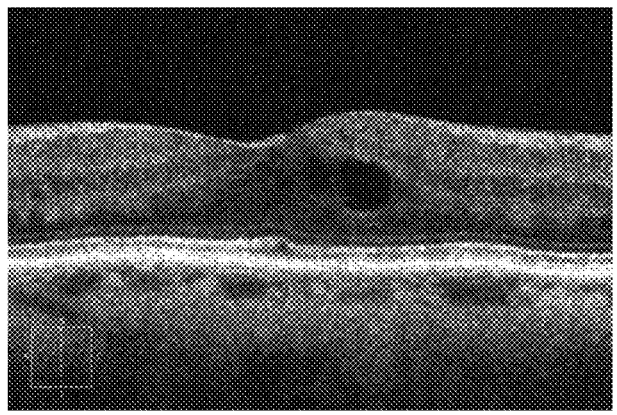
FIG. 13A
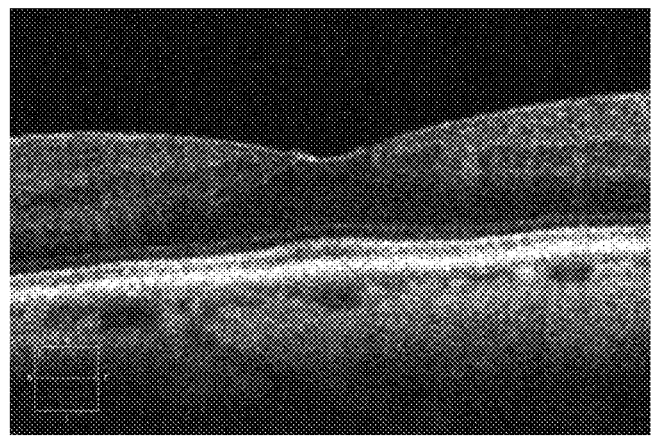
FIG. 13B
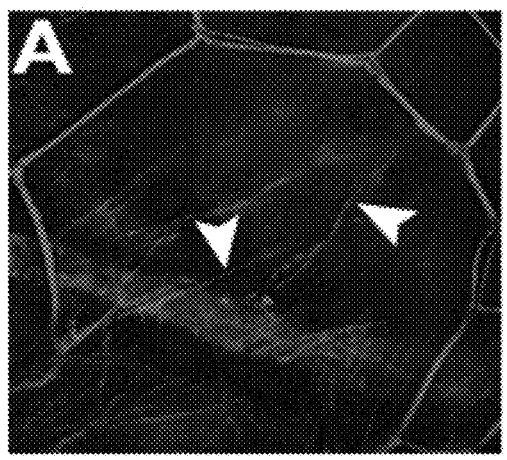 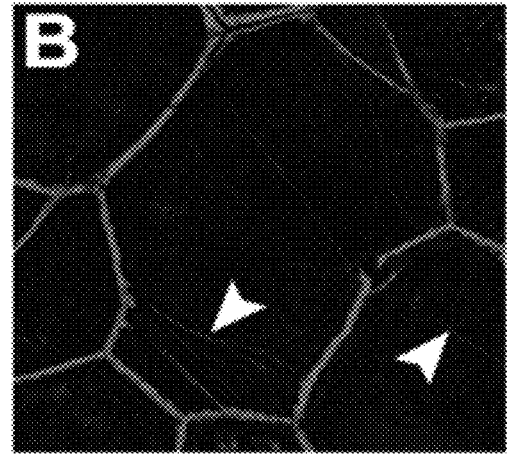
FIG. 14A  FIG. 14B

METHOD OF TREATING MACULAR DEGENERATION USING BOTULINUM TOXIN-BASED PHARMACEUTICALS

CROSS REFERENCE TO RELATED APPLICATIONS

This application is a continuation-in-part of and claims priority to U.S. patent application Ser. No. 15/834,491, filed Dec. 7, 2017, which claims priority to U.S. Provisional Application Ser. No. 62/431,512, filed Dec. 8, 2016, U.S. Provisional Application Ser. No. 62/449,914, filed Jan. 24, 2017, and U.S. Provisional Application Ser. No. 62/533,961, filed Jul. 18, 2017, the contents of which are each incorporated by reference herein.

BACKGROUND

Macular degeneration is a major cause of human blindness, generally occurring in the population over 50 years in age. The condition is genetic with offspring having about a 50% chance of inheriting a clinically significant condition form a parent who became legally blind from the affliction. Macular degeneration accounts for up to 70% of the irreversible blindness in the United States and is one of the most common problems encountered by Ophthalmologists. Worldwide, the projected number of people with age-related macular degeneration in 2020 will be 196 million and is predicted to increase 288 million in 2040. Reducing the rate of disease progression and improvement in duration potency and sustainability of current therapies would be very useful in reducing costs to national and state insurance carriers.

SUMMARY

Novel formulations and methods of treating and possibly preventing visual loss from macular degeneration by administering botulinum toxin-based pharmaceuticals are disclosed herein. Administration of the disclosed formulations can be intra-ocular or extra ocular, and, in some embodiments, may include subcutaneous, sub-muscular, intraneural, topical, intraosseous, and/or interfacial injection. As used herein, the term "intra-ocular" refers to the application of formulation directly to the globe of the eye and the term "extra ocular" refers to the application of formulation to regions other than the globe of the eye (e.g., to the eyelid or to the orbital). In cases where extra ocular injections are employed, complications of intra-ocular injections can be avoided. In some embodiments, repeated injections may be employed to keep biologic effect current and operational. Improvements in vision can be subjectively reported after treatment according to the disclosed methods and, in some cases, SD-OCT, fundoscopy, or other imaging techniques may be used to observe physical changes in the physical structure of the eye.

In some embodiments, an injection may penetrate the orbit and macular via pathways which do not cause a weakening of the extra ocular muscles, thereby avoiding diplopia, ptosis, and other neuromuscular effects which can create complications. As explained below in detail, the disclosed formulations and methods may be designed to target one or more of the following tissues: choroid, neuro retina, retinal pigment epithelium (RPE), peripheral nerves entering the eye, and/or other associated tissues. The disclosed formulations and methods may, in some embodiments, be used to treat both exudative forms of macular degeneration (i.e., with intra retinal fluid, blood, or sub-retinal fluid or blood and non-exudative forms, which can lead to geographic atrophy).

Prior to administering the disclosed formulations to a patient, a clinical assessment may be made by a qualified medical practitioner to evaluate whether treatment according to the disclosed methods is appropriate. Clinical assessment may be made based on one or more of the following: family history, fundus inspection using photography, SD OCT, with careful evaluation of the status of the retinal pigment epithelium for defective signs, including but not limited to presence of pigment in fundoscopy, pigment migration anteriorly into the neuro-retina (intra-retinal hyper pigment), presence and volume of drusen, focal intra retinal hyper reflection, sub drusenoid deposits, sub-drusenoid hyperreflectivity, dynamic reduction in drusen volume, second eye staging for severity, hypo reflectivity, choroidal neovascularization, hypo pigmentation, discontinuity and disappearance of OCT reflectivity lines (e.g., IS-OS, external nuclear layer, RPE layer), retinal and choroidal thickness or associated components, dynamic changes in any measurements, thickening of reflectivity lines, cyst formation, and any configuration of fluid formations. In some cases, activation of the RPE may be a risk factor for macular degeneration progression and an assessment may be made for progression risk based on one or more of: anatomic pathologic findings, history, and tempo of disease progression and status of the second eye.

As explained in detail below, the disclosed formulations and treatment methods may delay degeneration of the RPE, preserve photoreceptors, treat or prevent high risk leakage, treat and prevent neovascularization, prevent cell apoptosis, treat and prevent RPE activation, treat and prevent RPE migration, treat and prevent sheet distortion in the RPE, prevent geographic atropy, prevent retinal atrophy, prevent loss of rods and cones, convert wet stage to dry stage, preserve vision and/or restore vision.

BRIEF DESCRIPTION OF THE DRAWINGS

FIGS. 1A-1C are illustrations of the macula of an eye. In particular, FIG. 1A illustrates a healthy macula, FIG. 1B illustrates a macula suffering from dry macular degeneration, and FIG. 1C illustrates a macula suffering from wet macular degeneration. Wet macular degeneration is often associated with rapid loss of vision and dry macular degeneration is associated with slow progression loss of vision. Forms of dry macular degeneration can also indicate risk for conversion to a wet (exudative state) and should be followed by the clinician over time.

FIG. 1D is an image obtained using optic coherent tomography (OCT), showing breakage in continuity of the retinal pigment epithelium (RPE), as would occur in early-stage age-related macular degeneration.

FIG. 2 is an OCT image illustrating a dense disciform fibrotic scar in end stage macular degeneration. Portions of the scar illustrated in FIG. 2 demonstrate geographic atrophy (GA), with attendant loss of photoreceptors.

FIGS. 13A and 13B illustrate OCT images obtained from a patient treated with the disclosed therapeutic formulations, according to the disclosed methods.

FIGS. 14A-14D illustrate stress fibers in RPE cells.

DETAILED DESCRIPTION

Figure 3:
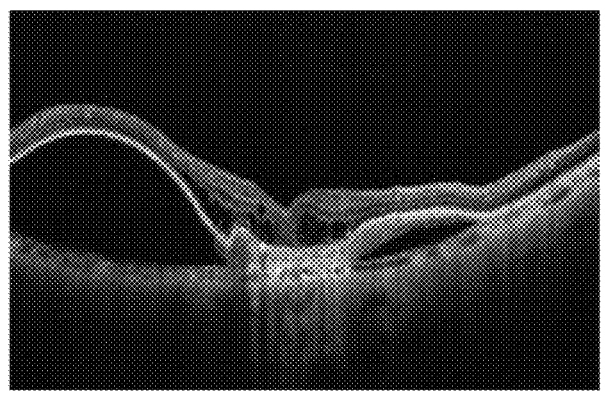
FIG. 3 is an OCT image illustrating leakage of fluid through the RPE under the neuro retina in a case of wet macular degeneration.

Macular degeneration generally destroys central vision in an afflicted individual, causing inability to read, drive and conduct an independent and productive life. The rapid decline of vision is generally associated with the exudative "or wet" form of the disease in which there is a leakage of fluid from newly formed pathologic choroidal vessels through the biologic barrier established by the retinal pigment epithelium. The leak through the retinal pigment epithelium leads to the destruction of photoreceptors with alteration in the structure of the retinal pigment epithelium into a fibrotic scar or an atrophic state with associated photoreceptor destruction.

Current treatments for macular degeneration involve intra-ocular injections of protein-based antibodies (monoclonal antibodies) to vascular endothelial growth factors (VEGF and related targets) resulting in diminished leakage from neovascularization and recession of the new vessel growth with restoration of the vital interface between the neuro retinal photoreceptors and the retinal pigment epithelium. These current therapies require intra-ocular injections due to the short half-life and molecular size of the existing agents. Intra-ocular injections practiced in the field of Ophthalmology carry many risks, including damage to intra-ocular contents (lens, retina, choroid and potential for intra-ocular infections).

In contrast to previous therapeutic approaches for macular degeneration treatment, a novel method of treating, preventing, slowing progression, mitigating, and/or reversing macular degeneration is disclosed. In the disclosed methods, botulinum toxin (in any known form, for example, botulinum neurotoxin or a fragment thereof) or one or more of its peptide fragments or neurotoxin associated proteins (accessory proteins) are injected intro intra ocular regions (i.e., the globe of the eye) and/or extra ocular regions (i.e., outside the globe of the eye, for example, the eyelid) of the patient. Application of the disclosed compounds to one or more extra ocular regions of the patient can treat or, in some cases, present visual loss from macular degeneration or any of its associated conditions. As described herein in detail, botulinum toxin and fragments thereof may undergo axoplasmic transport. Accordingly, providing botulinum toxin and related compounds to a patient's per-ocular region or extra orbital region(s) can allow for a unique route of penetration into intra-ocular regions and penetration into choroid, neuro-retina, and/or retinal pigment epithelium, without direct injection into the eye, avoiding associated complications such as diplopia and surgical damage associated with intra-ocular delivery. In the disclosed remote administration format, botulinum toxin and related compounds may produce barrier-enhancing effects and regression of pathologic processes associated with macular degeneration, all without potential complications associated with intra-ocular injection.

As used herein, the term "botulinum toxin" refers to any known from of botulinum toxin, including but not necessarily limited to: pure botulinum neurotoxin, a fragment thereof, and/or neurotoxin associated proteins. For example, the botulinum toxin may be produced by the bacterium *Clostridium botulinum* (for example, by fermentation) or by recombinant techniques, including engineered variants and fusion proteins. In some particular example embodiments, the botulinum toxin is produced using recombinant or synthetic chemical techniques (for example, a recombinant peptide, a fusion protein, and/or a hybrid neurotoxin prepared from subunits of different botulinum toxin serotypes). The botulinum toxin may be of serotype A-H and, in some embodiments, the botulinum toxin is present as an isolated botulinum neurotoxin molecule (e.g., botulinum toxin type A neurotoxin having a molecular formula of $C_{6760}H_{10447}N_{1743}O_{2010}S_{32}$ and an atomic mass of 150 kDa). The formulation Xeomin® (incobotulinumtoxinA), is an example of a pure botulinum neurotoxin (devoid of associated accessory proteins). In embodiments with an isolated botulinum neurotoxin molecule, one or more exogenous stabilizers (e.g., albumin) may also be included in the formulation. In embodiments with botulinum toxin in a complexed form (i.e., with hemagglutinin and associated proteins present), one or more exogeneous stabilizers may also be present. In some particular example embodiments, the botulinum toxin used in the disclosed formulations and methods includes one or more associated proteins that are devoid of pure neurotoxin. Some example associated proteins that are devoid of pure neurotoxin include but are not limited to hemagglutinin derived from the fermentation processes which create the raw materials for botulinum toxin-based pharmaceuticals (e.g., Hall strain fermentation for botulinum toxin type A) and non-hemagglutinin, non-neurotoxin from the fermentation of the same process. Additionally, hemagglutinin and fragments thereof which carry specific activity on cell to cell adhesion proteins (e.g., cadherin or other associated proteins) can be separated or genetically expressed in suitable carriers which subsequent purification. Fermentation processes prototypes have been described (e.g., Borodic G E, Pearce L B, Johnson E, Schantz E: *Clinical and Scientific Aspects of Therapeutic Botulinum Toxin Administrations*, Ophthalmology Clinics of N America, September, Vol. 4, No. 3, 1991). In some embodiments, purification of end products of fermentation may create the raw materials for the associated proteins. Proteins can be recombinant process expressed from whole or portions of identified genes corresponding to associated proteins.

In some embodiments, the disclosed formulations may include a botulinum toxin (in pure neurotoxin form or with neurotoxin associated proteins present), hemagglutinin (in any known and suitable form), and/or one or more anti-VEGF agents. In some embodiments, the botulinum toxin may be fused to the anti-VEGF agent(s) present, while, in other embodiments, the botulinum toxin may be separate and distinct from (i.e., not fused to) the anti-VEGF agent(s). As demonstrated in example experiments and embodiments described herein, botulinum toxin has been proven to increase potency of existing anti-VEGF agents.

Fusion proteins are produced using genetic material corresponding to a protein or protein fragment, wherein the genes from one protein are ligated (via suitable ligases) to one or more separated genes corresponding to other proteins created a protein hybrid with preservation of the desired biologic activity of each protein to create a useful agent or drug. The fused genetic material may be amplified by PCR in the process, often with addition of connecting materials and elimination of termination codons. In some embodiments, target domains of botulinum toxin can involve selective nerve uptake (near carboxy terminus of the botulinum heavy chain, fragment of botulinum molecule, or accessory molecules), which express proteins involved in forming or regulating expression of structural proteins connecting cells or regulating cytoskeleton, or involved in proteins governing RPE function, or rod con function. Further, proteins with anti-VEGF activity can be fused with botulinum toxin or its fragments or accessory proteins or fragments. Further monoclonal antibodies targeting inflammatory mediators such as complement or other inflammatory autacoids can be added to a fusion protein, which contains a botulinum fragment. Rho and/or ROCK modulators may also be added to the fusion protein, in some embodiments. One or more fragments of VEGF receptors, entire receptors, fragments of nerve growth proteins, VEGF subtypes or fragments which impede angiogenesis, and/or immunoglobulin fractions which improve protein stability and decrease immunogenicity may also be added, in some embodiments.

A unique aspect of fusion proteins relates to fluorescent tags, which can be used to study transport in animal models (and possibly clinically) to further understand axoplasmic flow dynamics to target specific retinal and choroidal tissues from injection outside the globe and penetrating through various structures such as peripheral nerves. In this disclosure, fusion proteins may be formed with botulinum toxin-based carriers, which affect binding and transport through peripheral nerves. The fusion protein may contain both the carrier portions of a botulinum subtype, a fragment of a botulinum type, and a fluorescent marker, in some embodiments. Other additions with biologic effects can be added to the fusion protein. Such compositions can be used to study the pharmacodynamic effect of botulinum toxin-based pharmaceuticals in vivo using standard photography used in ophthalmic practice (e.g., fluorescein angiography). In some such embodiments, the tag can also confirm that adequate drug has been delivered to the lesions on the retina or choroid targeted for treatment. Differential penetration to targeted lesions by the therapeutic agent may also provide important individualized dosing, general dosing, effectiveness of carrier proteins, formulations, and pre-clinical data necessary for qualifying a fusion protein for clinical use. The disclosed methods may also involve direct visualization of retinal tissue in vivo or in vitro for penetration and localization in the retina and choroid.

In these and other embodiments, the disclosed formulations may also include a stabilizing excipient, such as albumin. In embodiments where one or more accessory proteins (i.e., complexing proteins, such as hemagglutinin) are present, the concentration and/or activity of the accessory proteins may be increased from naturally-occurring levels. Numerous configurations and variations will be apparent to those skilled in the art upon consideration of the subject disclosure and teachings provided herein.

Current Macular Degeneration Treatment Methods

Currently, effective therapy for age-related macular degeneration (AMD) is limited to the wet form treated with anti-vascular endothelial growth factors ("anti-VEGF") agents and related fusion proteins with both antibody and receptor. The primary treatment for "wet AMD" is intravitreal injection with VEGF inhibitors. Currently, ranibizumab (Lucentis®) has FDA approval, whereas bevacizumab (Avastin) is used on an off-label basis. Eylea® (aflibercept) has been recently approved for macular degeneration with a slightly improved duration of action. Each of these drugs are given by intra-ocular injection. Eylea®, the newest FDA approved agents, achieves a commercial sale of almost 1 billion dollars per quarter.

Macular degeneration occurs in stages, typically starting with visible alterations of the retinal pigment epithelium on direct observation using photographs made through the human pupil and disruption of the cellular organization of the retinal pigment epithelium on optic coherent tomography (OCT). FIGS. 1A-1C provide illustrations of the various stages of macular degeneration, with FIG. 1A illustrating a normal macula, FIG. 1B illustrating dry macular degeneration, and FIG. 1C illustrating wet macular degeneration.

FIG. 1D is an image obtained using OCT, illustrating breakage in continuity of the retinal pigment epithelium, as would occur in early-stage AMD (age related macular degeneration). Disconnection and disruption of the retinal pigment epithelial cells can lead to tectonic barrier defects within the retinal pigment epithelial sheets and basement membrane (Bruch's membrane) and growth of new blood vessels from the choroid layer of the posterior human eye. During AMD, retinal pigment epithelial cells are often seen breaking away from contiguous and adjacent cells adapting a migration into the neuro-retina (as shown in FIG. 1D). Discontinuity of the integrity of the retinal pigment epithelium is an important component in the pathogenesis of the disease. In stage 1 of the disease, atrophy, migration, autolysis, and disorganization occur in cells and associated pigment, leading to an abnormal appearance of the macular with irregularity of the pigment characterized by disruption in the usual pigment densities surrounding the fovea and irregular cell shapes, often with breakage of retinal epithelial barriers as the disease progresses. Alterations of the retinal pigment epithelium (RPE) leads to the formation of drusens (and drusenoid) pseudo drusens, pigment clumping, speckling, vitelliform regions, and hypopigmentation. In some cases, these symptoms may appear before more devastating changes occur (for example, geographic atrophy, choroidal neovascularization, and sub-retinal hemorrhaging). Methods of increasing the blood flow to the choroid are also disclosed herein. The disclosed methods may, in addition to other advantages, increase the uveal scleral pumping mechanism, causing a suction effect on the RPE, and allowing for maintenance of linear and planar integrity of the RPE. The disclosed methods of administering botulinum neurotoxin may also increase efficacy of removal of molecular metabolites, which are toxic to cellular function.

As the disruption in cell to cell adhesion and cell to basement membrane adhesion advances, the growth of new vessels from the choriocapillaris through the pigment epithelial defects leads to further, more dramatic, vascular and choroidal leakage, disruption of the neural-retinal and retinal pigment epithelium apposition, ultimately resulting in devastating destruction of the photoreceptors (rods and cons) with loss of vision characterized by a central blind spot and loss of a person's ability to read.

FIG. 2 illustrates a dense disciform fibrotic scar with geographic atrophy (GA) in end stage macular degeneration. The eye shown in FIG. 2 is beyond legally blind. The disciform fibrotic scar shown in FIG. 2 is likely formed by collagen and related polarization of filamentous protein from other cellular elements. The retinal pigment epithelium (RPE) shown in FIG. 2 has undergone metaplasia to fibrous scarring (a process involving epithelial to mesenchymal transformation) and flat cellular atrophy and degeneration. This is an irreversible (end-stage) form of macular degeneration and difficult to treat.

FIG. 3 is an image obtained using OCT techniques and illustrates leakage of fluid through the RPE under the neuro retina in a case of wet macular degeneration. The type of leakage illustrated in FIG. 3 is generally associated with rapid vision deterioration and requires immediate medical intervention. Wet macular degeneration (as shown in FIG. 3) can be treated using drugs such as Avastin®, Lucentis®, EYLEA®, and abicipar (Allergan). These current drugs include different antibodies to various isoforms of vascular endothelial growth factors (VEGF), which cause recession of the developing neovascularization and/or leakage, resulting in return or stabilization of vision with partial restoration of the structural derangement in the retina with reduction in sub-retinal fluid.

Treatment with these drugs (anti-VEGF agents) usually require multiple injections and carry the risk of intra-ocular hemorrhage, infections (e.g., eye threatening endophthalmitis), PVR (post-operative proliferative vitreoretinopathy), lens dislocation, cataract, glaucoma, and/or retinal break and detachments. These injections can also be painful. The more injections that are given to a patient, the higher the chance of an administration-related complication. Injections into the eye are more painful than soft tissues surrounding the eye (e.g., lid, orbit, periocular and/or orbital muscles). Experts in the field of monoclonal antibodies and genetically engineered proteins have tried to prolong the duration of anti-VEGF agent action using a fusion protein between an anti-VEGF antibody, fractions of VEGF receptor 1 and 2, and Fc portion of immunoglobulin.

Overview of Presently Disclosed Treatment Approach

Without wishing to be bound by theory, enhancing the duration and potency of anti-VEGF therapy using an agent with a very long duration of action such as botulinum toxins, may add to both safety and to improvement in the targeted relief of leakage, neo vascularization or tectonic instability of the continuity of the retinal pigment epithelium. Extraocular botulinum toxin can be used repeatedly, with well-defined, superior safety results. Extra ocular botulinum injections may, in some cases, eliminate the risk of intraocular hemorrhage, infections (endophthalmitis), lens dislocation, cataract, and/or retinal break and detachments which can occur with existing therapeutic standard.

Fewer injections over longer intervals would be an improvement over existing therapeutic approaches. Many complications of the currently known treatments for macular degeneration are related to the anti-VEGF intra-ocular injection procedure rather than a medicinal side effect of the agent. Botulinum toxins work for a longer period than known agents currently used for this condition. Further, diminished injection frequency would provide safer and more convenient treatment methods for patients.

In some embodiments, botulinum toxin can be used in conjunction with VEGF antibodies to further enhance potency of the injectable. For example, in some cases, treatment of macular degeneration can be accomplished with one or more applications. Additionally, the disclosed botulinum toxin-based compounds may reduce or eliminate the need for frequent intra-ocular injections. Furthermore, botulinum toxin can be used with other agents that promote actin polymerization, such as nerve growth factor. Botulinum toxin may, in some cases, influence and bind to cadherin proteins, catenin polymers and on the Rac 1 system of acting on intracellular and extracellular actin with enhancement of barrier functions along an epithelial or endothelial surface. Botulinum toxin also can be transported by axoplasmic flow, a unique property that allows transport into the eye without causing paralytic neuromuscular effects on extra-ocular muscles. As direct diffusion of botulinum toxin-based compounds may cause paralysis of extra-ocular muscles, the axoplasmic route of entry provides a novel delivery method for intra-ocular disease and may be used for any of the disclosed compounds. In embodiments where an axoplasmic route of delivery is employed, medication may be delivered through nerves entering the back of the eye (posterior delivery) rather than the front of the eye (intravitreal, drop-topical, or intra-cameral delivery). This is a surprising improvement, which advantageously avoids vision-destroying diplopia Fragments of botulinum toxin also can, in some embodiments, be fused with anti-VEGF agents to provide an intra-ocular administration via axoplasmic flow, thereby avoiding the need for intra-ocular injections even for these agents which must currently be used by riskier intra-ocular injections. Botulinum toxin may interact with mast cell leading to alterations in maintenance neurotransmitters, neuropeptides, trophic agents, nerve growth factors, important to maintain a healthy retinal pigment epithelium. Other mechanisms of action are also possible and contemplated.

Anatomy of the RPE and its Impact on Macular Degeneration

The RPE is a neuro-derived structure in utero which forms a cellular sheet with cell structure taking the configuration of a regular (equal sided hexagon) in RPE-RPE cell to cell contact. The apical surface is in the form of a microvilli which maximizes the physical contact with photoreceptors (rods, cones), allowing the physiologic phagocytosis of the photoreceptor membranes while the base of the RPE is attached tightly to its basement membranes (Bruch's membrane). This anatomic arrangement has been geometrically proven to maximize the compactness of the cells minimizing the connection of the cell surfaces. This assessment is also the same arrangement for a honey bee hive, and subject to a proposition made over 2.00 years ago (36 BC) by Roman scholar Marus Terentius Varro (the Honey bee conjecture). Geometric proof followed by Thomas Hales in 1999 (University of Michigan). This conjecture proposed that the regular hexagon sheet minimized connection material while maximizing sheet area. This anatomic allows bees to economize on producing beeswax in constructing the hive. This arrangement indicated the functional barrier is important for RPE cells and the biology of maintaining this barrier effect is a vital target for use of botulinum toxin to treat macular disease.

Figure 4A:
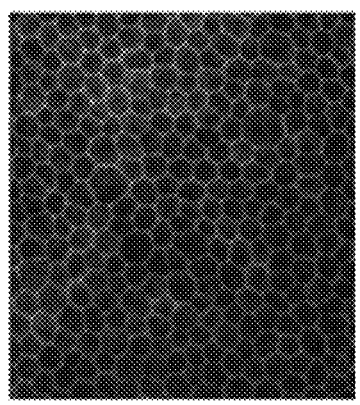
FIGS. 4A-4C illustrate the hexagonal structure of the RPE.
Figure 4B:
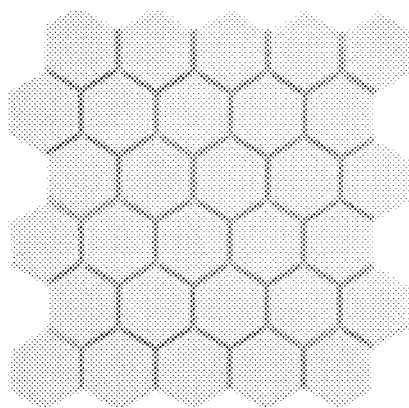
Figure 4C:
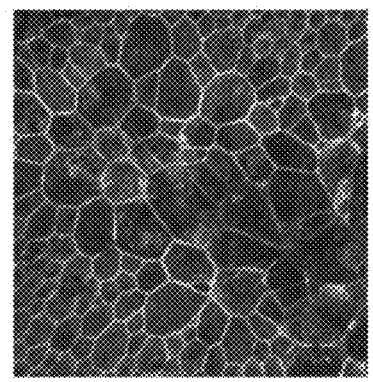
Figure 5A:
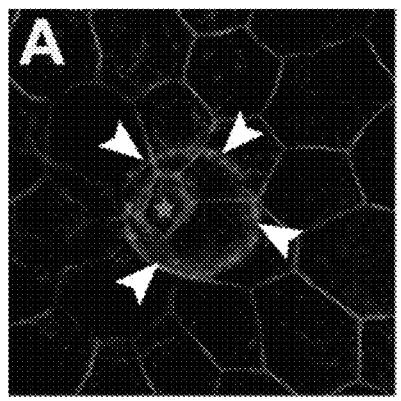
FIGS. 5A-5F illustrate disruption of membranes, sub membrane condensation, alteration of hexagonal shapes of the structure, RPE autolysis, stress fiber formation from actin associated with macular degeneration.
Figure 5B:
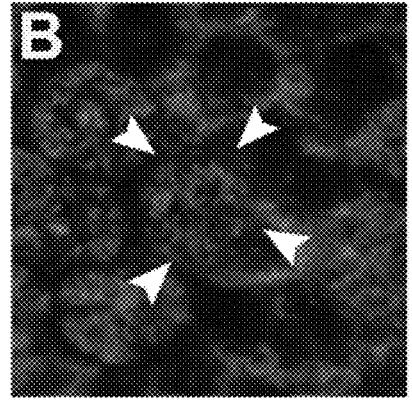
Figure 5C:
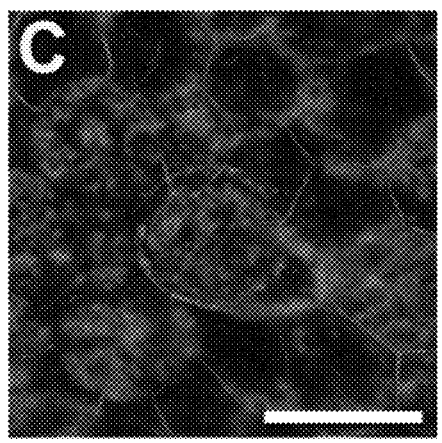
Figure 5D:
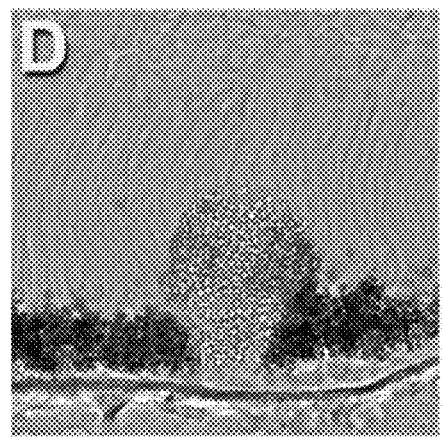
Figure 5E:
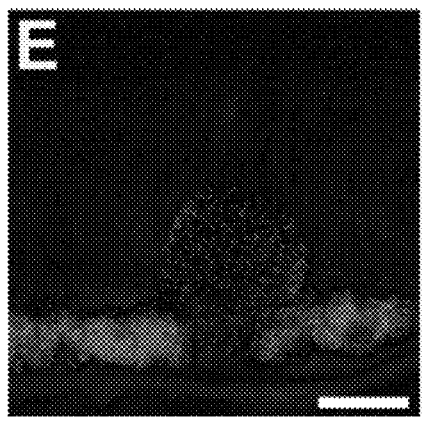
Figure 5F:
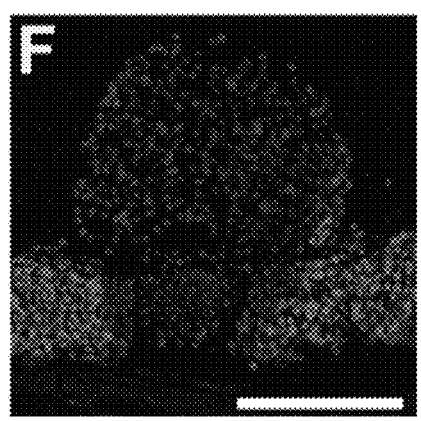

FIGS. 4A-4C illustrate the hexagonal structure of the RPE. In particular, FIG. 4A illustrates healthy RPE and FIG. 4B illustrates interlocking hexagon structures. In the RPE, the structure allows for an economy for actin production, one of the major intracellular protein governing the attachments of the cell to cell adhesion, and the structural protein forming the submembrane support for the hexagon. Further, the microvilli of the RPE surface also is supported in structure by the projection and maintenance of intracellular actin, as well as the RPE attachment of the basement membranes. Actin also attaches to other cell to cell protein such as cadherins which functions as the grout-glue of the RPE sheet and support its functioning barrier effect. Derangement in actin formation, formation of altered forms and arrangement of actin and associated proteins, and regression of microvilli have been described as early changes in stage 1 age related macular degeneration and related diseases. FIG. 4C illustrates an RPE suffering from macular degeneration. As illustrated in FIG. 4C, the actin and microvilli of the diseased cells are misshapen and no longer arranged as orderly hexagons.

Without wishing to be bound by theory, botulinum toxin type A may act as a stimulator of actin on neural tissue. In other words, botulinum toxin may have an effect on neurally-derived RPE, providing a unique opportunity to alter RPE cells in certain disease states, such as age-related macular degeneration. In some cases, cell-to-cell barrier function, enhancement of microvilli surface area, and perhaps other associate structural proteins may provide a method to maintain RPE structure and function. In some embodiments, botulinum toxin may retard the progression of the various stages of macular degeneration and related retinal diseases. Increased blood flow to the choroid can increase the removal of toxic metabolites. In some embodiments, the toxic metabolites removed from the choroid cause or increase suction-related pressure change in the choroid, resulting in detrimental changes in genomic expression, RPE alignment, as well as reduction in EMT and RPE barrier function. The disclosed methods also favorably slow progression of dry macular degeneration and reduce conversion of dry macular degeneration to exudative (wet) macular degeneration. The genomics expression toward actin may function to keep RPE cells in the differentiated state, allow adhesion, and prevent separation from surrounding cells and attachment to its basement membrane. It is conceivable that the genomic effects also keep the RPE cell producing other adhesion proteins (and functionally-related proteins) expressed. Repression mRNA expression of proteins of the RPE cell, which govern motility, cell death, cell atrophy, or metaplasia to a fibrocyte may also be possible and could be used to treat various stages of macular degeneration. This effect can be operational, in part with other mechanisms, but structural changes are critical to RPE, a layer derived from neural tubes, with attendant neural elements. The neural elements of the RPE may allow this useful interaction with botulinum neurotoxin(s) that allow and/or promote a therapeutic response.

Overview of Therapeutic Compounds and Related Methods

In some embodiments of the subject disclosure, a therapeutic formulation is provided. For example, in some embodiments, the therapeutic formulation comprises botulinum toxin (e.g., botulinum toxin types A-G, specifically, C2, C3 and/or various subtypes of A (for example, A1-A5)). The botulinum toxin included in the disclosed therapeutic formulation may be prepared with standardization of biologic activity via dose using LD 50, enzyme cleavage of SNAP-25, time to death assays, neuronal cell based assays, or any other method of measuring biologic activity to produce suitable dosings. Any fusion protein added to a fragment or a native structure of the botulinum toxin which enhances potency can also be used in the disclosed formulations. The disclosed formulations may also include permeation adjuvant peptides or other molecules which can enhance diffusion through membranes or potency duration, such as poly-lysine polymers or albumin, in some embodiments. Suitable adjuvants may include but are not limited to: polycationic or poly ionic peptides, hyaluronidase, and/or derivatives of local anesthetics (e.g., lidocaine, Marcaine).

In some embodiments, an injection can be administered through the pars plana so as to avoid retinal tissues, ciliary body or lens. In some such embodiments, the injected formulation may flow from the injection site into the vitreous body. The formulation may then diffuse into the neuro retina and subsequently diffuse into the retinal pigment epithelium. The toxin may then be taken up by the retinal pigment epithelium, neo vascular membranes, or diffuse through defects in Bruch's membrane, blood retinal barrier, and/or into the choroid. Any suitable level of activity may be utilized in some such methods. The retinal pigment epithelium has an extremely active in membrane vesicular cellular uptake interacting with the rods and cones of the neurologic retina and could, in some cases, easily incorporate the molecular botulinum toxin into its cytoplasm. Alternatively, the botulinum toxin may be given in upstream neural structures (for example, the peripheral nervous system) which eventually penetrate the inner eyeball via axoplasmic flow.

In cases where the disclosed formulations are injected, one or more of the following results may be achieved: (1) leakage from new vessel formation with fluid egression under the neuro-retina or retinal pigment epithelium may be decreased; (2) regression of new blood vessel growth may occur; (3) the retinal pigment epithelium degeneration may regress, resulting in intracellular morphologic changes, including reduction of retinal pigment epithelium activation; (4) cellular element polarity of the retinal pigment epithelium may be preserved, with enhancement of its barrier function and metabolic activity with enhancing density, length, and expression of microvilli; (5) enhancement of the tight junctions within the retinal pigment epithelium and enhancement of pigment epithelial attachment to its basement membrane may occur; and (6) enhancement and increased choroidal blood flow in the choriocapillaris and under the fovea and perifoveal regions.

In some cases, injection results may be measured using one or more of the following: (1) visual acuity and/or validating methods of measuring acuity; (2) contrast sensitivity; (3) fundus photography; (4) fluorescein angiography (including OCT angiography with various orientations for assessment of choroidal perfusion); (5) OCT (for example, examining sub retinal fluid, neovascularization under and through the retinal pigment epithelium, of any physical type); (6) changes in the RPE (drusen/drusenoid heights and volumes, density, distance from basement membrane, migration, loss of photoreceptors, loss of IS-OS and outer nuclear lines, fluid accumulations in retina and subretina, pseudo drusen density, pigment clumping and tears, choroidal thickness, neuro-retinal thickness, RPE atrophy, formation and leakage pattern of choroidal neovascularization, extent of geographic atrophy, hemorrhage, and shape and regularity of lines of retina defined by OCT (for example, ONL, IS-OS, RPE alignment; (7) Amsler grid; (8) auto florescence from RPE lipofusen; (9) focal ERG (electroretinogram); (10) polarity, thickness and shape changes in the retinal pigment epithelium using OCT; (11) visual fields; (12) any subjective instrument which assesses patient satisfaction that has been validated against objective measurements; and (13) use of conventional clinical study methods using controls and repeated injections. In some cases, serial follow-ups may be made with the patient and assessments of the need for repeated injections may also be utilized, as needed. In these and other embodiments, fundus photography and OCT may be used for monitoring treatment effect. The OCT-A is particularly useful for assessing improvement in choroidal blood flow in critical areas of the macula (e.g., in the choriocapillaris). Specifically, OCT-A techniques can be effectively used to evaluate retarding and/or prevention of development of dry macular degeneration using the disclosed methods. OCT-A with standard OCT can detect beneficial effects of botulinum toxin on defects in the Bruch's membrane (e.g., breaches in the Bruch's membrane), fluid in sub retinal space, and/or linear RPE organization and integrity. Laser Doppler techniques can also be used to assess choroidal blood flow, if desired. As used herein, the term "choroidal blood flow" includes, relates to, and/or refers to blood flow in the choriocapillaris.

Effects of Botulinum Toxin on Intra Cellular Cytoskeleton

Botulinum toxin may have important biologic effects on endothelium and RPE, which plays an important role in the pathogenesis of degenerative and exudative forms of human retinal disease. The RPE has been studied using electron microscopy during early stages and later stages of age related macular degeneration. Studies have revealed condensations of intracellular cytoskeleton near the basement membrane (base) of the cells causing disruption of the cell membrane, with cell shape irregularity, loss of polarity, disruption in cell to cell adhesion, accumulation of leaked protein with membrane instability, and derangements of the apical-apical orientation of the RPE cells with the rods and cone cellular structure. A distortion of the RPE can result in one or more of the following: (1) inability of the RPE to sustain its supportive functional and metabolic interplay with macular rods and cones, maintain the tight barrier between the choroid and neuro-retina allowing for emission of reactive macromolecules from the neuro-retina into the choroid. Such exposure excites release of vascular growth factures as well as mediators from choroidal endothelial cells, nerves, mast cells leading to fluid accumulation under the neuro retina (RPE and neurosensory detachment, hall mark of both "wet" and "dry" macular degeneration); (2) leakage from the neo-vascular endothelial tight junctions which occurs because of a deranged cytoskeleton associated with endothelial vasculature; (3) exposure of the antigenic structure of the neuro retina through the blood retinal barrier, causing reactivity of immune cells in the choroid with a limited response from blood containing cellular elements which circulate through the choroid. The immune response can include complement activation, which further damages RPE structure; (4) interruption of the rates of nutrient delivery into the neuro retina leading to toxicity of the rod and cones and RPE; (5) loss of RPE micro-villi, critical for maintaining rod and cone function by removal of photoreceptor breakdown products; (6) destruction of rods and cones; and (7) formation of a geographic atrophic state of RPE.

FIGS. 5A-5F show images of RPE obtained using microscopy techniques. In particular, FIGS. 5A-5F illustrate disruption of membranes, sub membrane condensation, alteration of hexagonal shapes of the structure, RPE autolysis, stress fiber formation from actin (shown in FIG. 5A), barrier function disruption, and migration of the RPE away from the barrier sheet. It should be noted that structure and function relationship of the neuro-retina is one of isolation from blood elements with most of the exposure being to vitreous body, a chamber containing hyaluronidate with no transient perfusion. Defects in the retinal vasculature are fairly consistent in creating retinal pathology. The blood retinal barrier in the retinal and choroidal vascular is important to the health of the neuro retina. The choroid is one of the most densely perfused tissues in the human body and the RPE and photoreceptors are highly metabolically dependent on a close structural relationship with the choroid. Separation of the blood compartment with both retinal and choroidal vascular is important in maintaining neuro-retinal health and functional integrity of photoreceptors. Further, certain antigenic stimuli get exposed with barrier breakdown which excites genetically individuals to react with immune responses at varying levels including but not limited to complement activation, neurogenic reactivity, alteration in regulatory autocoids, alterations in cell functions independent of inflammation, fluid accumulations within neuro-retina, barrier incompetence in choroidal and retino vascular endothelium, and dysfunction of the RPE photoreceptor functions.

The disruptions of the cytoskeletons of endothelium and RPE by cytoskeleton structure in endothelium and RPE are important to the pathogenesis of macular degenerations with respect to leakage of blood containing fluid and membrane altering mediators and function of the choroid of the eye. Generally, increased in generation of pathologic arrangements of actin, microtubule proteins, accumulated as a first step in macular degeneration associated with distortion of RPE and endothelial membranes, which may cause: (1) toxic leakage of sub retinal fluid (wet macular degeneration); (2) loss of cell to cell adhesion and cell to basement membrane adhesion disruption of barrier function (drusen and drusenoid formation, RPE migration); (3) loss of polarity orientation of RPE, which can be important to its role supporting the structure and function of the rod and cones (progressive dry degeneration) and may ultimately result in loss and retraction of RPE microvilli; (4) loss of RPE ability to remove photoreceptor breakdown products (lipofuscin) at a sufficient rate to avoid photoreceptor toxicity (auto florescence increase); (5) pathologic condensation of RPE intracellular fiber elements ultimately reflected by metaplasia of the RPE into a white "fibrocystic" cell type which appears on fundus photography as a "Disciform scar" (see FIG. 2) and formation of geographic RPE atrophy and neurosensory retinal atrophy; (6) disciform scars and geographic atrophy are often seen in patients blinded with macular degeneration reflecting evidence of the nature of the degenerative and deranged process by which the macular is destroyed by alteration in accumulation orientation of intracellular pathologic actin and related fiber accumulation, which fundamentally alters the RPE and causes RPE/photoreceptor death. The ensuing result is retinal pigment epithelial to mesenchymal type differentiation to a fibrocyte, migrated cell, and/or atrophic cell. The ensuing events involves a substantial change in mRNA expression by the RPE to reorganized cell attachments, basement membrane attachment, pigment epithelial motility and migration into the neuro-retina. This process denotes the early changes in macular degeneration with vascular response with growth of vessels into the RPE and choroid denoting the later stages (FIG. 1, stages of macular degeneration). Following barrier function disruption, immune process may ensure, which results in complement activation, mast cell activation, neuropeptides release, which further aggravates disrupted barriers and fluid accumulation; and/or (7) genomic changes resulting in altered RPE morphology, retinal layer tissue dysfunction and loss of photoreceptors.

It should be noted that botulinum toxin can get into cells either via specialized receptors as exists on nerves cells or by facilitation with adjuvant proteins either in vivo or in drug formulation. Vital concentrations may, in some cases, be inherently low with this molecule's ability to effect enormous changes in cytoplasmic physiology or genomic responses and exquisitely low molecular concentrations.

Botulinum and Cytoskeleton Interactions

The disclosed formulations and methods, in some embodiment, involve injections or topical application of a botulinum toxin formulation for the treatment of macular degeneration and other relational degeneration. Botulinum toxin A may have a critical effect on cytoskeleton structures. The C3 version has been noted to interact of the Rho actin polymerization system in cellular biologic experimental observations. While the C2 and C3 toxins may not cause neuromuscular weakness, these agents are cyto toxins able to cause cell death by different mechanisms than type A subtypes, B, C1, D, E, F, and G. Further, as described in detail below, animal injection of type A botulinum into muscle cells may cause a shrinkage of cells associated with diameter morphometric out of proportion to the effect created by nerve cutting (neurogenic atrophy). This rapid rate observation (which was not previously reported) indicates that the A toxin has a fundamental direct effect on the cytoskeleton of muscle cells independent of neuromuscular blockage associated with blocked acetyl choline release on myoneural junctions. This effect may cause a dissolution and re-organization of cytoskeleton actin and related intracellular micro tubules to an extent that the effect can interfere with a degenerative process leading to cell death, critical dysfunction, and block a critical disease degenerating process so as to preserve cell function. Caspase and apoptotic intracytoplasmic enzymes can be depressed, in some cases. The effect would be to maintain polarity of vital cell structures such as the RPE, delay or halt the accumulation of pathological cytoskeleton proteins, with preservation of cell structure polarity and associated cell interacting functionally with the target cell group.

In some embodiments, endothelial cell health can be preserved as well as integrity of any cell undergoing a degenerative process by increases in the intracellular generation of cytoskeleton protein which disfigure the shape or critical cell configuration destroying critical junctions and associated barriers, movement of metabolites, neuro-retinal antigenic exposure, or cell to cell relations. Such changes can be elicited by alterations in expression of cellular adhesion proteins, interactions with vital surface and internal receptors governing cell metaplasia, apoptosis, epithelial mesenchymal transformations, epithelial sheet loosening and adhesiveness to basement membranes, alterations in the quantity of various isoforms of adhesion proteins such as cadherin isoforms and related proteins so as to alter barrier functions of epithelium and endothelium to inflammatory cytokines (such as VEGF) and related proteins. Important barrier functions in macular degeneration include endothelial governing leakage, epithelial cell to cell adhesion governing RPE barrier, choroidal neo-vascular barrier functions along the neo vascular endothelium. Additionally, botulinum toxin can suppress inflammatory autacoids, such as mast cell function.

In the case of the RPE, the tight junctions at the level of the RPE can become incompetent from abnormal cytoskeletal protein accumulation, causing barrier fractures along tight junctions with ensuing antigenic exposures of the neuro retina to choroid, with opportunity for various immunologic and inflammatory proteins to egress, choroidal fluid, and subsequent photoreceptor death based on immunologic reactivity. Using the disclosed techniques involving the administration of botulinum toxin, barrier effects can be improved and barrier leakage can be mitigated, due to increased blood flow in regions affecting the macula. Such as process involves histamine release inferentially present in platelets and mast cells both present in choroid. Vasoactive intestinal peptide and CGRP may also play a role. Mast cells are capable of interplay with autonomic nerves present in choroid and still another target for botulinum modulating or blocking effect. Barrier function seems to be implicit and tissue organization of the retina and choroid and disruption of this function may be viewed as upstream derangement, occurring in macular degeneration. It is noted that retrograde movement (toward the central nervous system) and ante grade movement (away from the central nervous system) of botulinum toxin via peripheral nerves or veins occurs during use of the disclosed compositions and methods. Further, direct penetration of the disclosed formulations into the eye may encounter natural barriers of scleral and cornea. Prior to the filing of the subject application, botulinum toxin has not been advocated for intraocular diseases. This is due, at least in part, to the fact that the eye barrier was previously believed to block the neurotoxin from entering the eye.

Interaction of the RPE and Photoreceptors

The phagocytic interaction of the RPE on the rods and cones is critical for photoreceptors health. Damage to this interplay will result in photoreceptor damage and eventual death with vision loss. Driving this relationship at the sub cellular level is the microtubules within the retinal pigment epithelium which allows for phagocytic interactions at a rapid cellular rate, with active actin and related tubule polymerizations allowing for photoreceptor maintenance. Defects in cytoskeleton assembly maintenance and disassembly can result in photoreceptor damage. Such defects can be reflected in the disorganization of the polarity of the RPE cells as well as alterations in cell shape actin and tight junction integrity and cellular relationships on the basement membrane (Bruch's membrane). Early macular degeneration changes are associated with alterations in RPE morphology and accumulation of dense accumulation of subcellular fibers indicating microfiber dysfunction (Drusen body accumulation). Auto fluorescence is a sign of RPE dysfunction, indicating a compromised RPE with accumulation of Rhodopsin due to defective catabolism and accumulation of lipofuscin pigment seen with blue light filters on retinal cameras. Lipofuscin is an indication of functional RPE dysfunction and often occurs in both wet macular degeneration and in progressive dry macular degeneration with geographic atrophy. Increasing removal of lipofuscin and various other metabolites due to an increase in the blood flow-driven uvea scleral pump is useful in improving the outcome of stages of macular degeneration characterized by RPE-pumping dysfunctions.

Botulinum Toxin and Microtubule Derangements and Microfiber Accumulation

Botulinum toxin has the ability to alter the accumulation formation of subcellular actin and microfibers so as to suppress the pathologic accumulation polymerization of critical cytoskeleton components to provide one or more of the following:
1. Maintain barriers within the RPE essential for maintaining integrity of the neuro-retina and rods and cones maintained by tight junctions.
2. Maintain polarization and cytoskeleton to assure continued function.
3. Maintain integrity of endothelium and suppress neovascularization from the choroid
4. Block or modulate mast cell activity and modulate release of neuropeptides or other mediators in the choroid which can damage or sustain photoreceptors.
5. Microvilli enlargement and enhancements.
6. Barrier function within the basement membrane attachments of the RPE and cell to cell adhesions of the RPE.
7. Block exudative vascular leakage from choroid.
8. Improving choroidal blood flow by increasing the pumping mechanism of the choroid and pressure effects on the RPE.

Botulinum Interplay with Microvilli of the Retinal Pigment Epithelium

The retinal pigment epithelium contains microvilli, a critical structure maintaining the physiologic health of the rod and cones of the neuro-retina. The neuro-retina structures convert images and light into transmittable signal into brain via optic nerve projections allowing for visual decoding within the central nervous system. The effect of age is to dwindle the extent, size and integrity of the microvilli causing a dysfunctional microanatomy between the rods and the cone ultimately leading to the early stages of macular degeneration. The effect of botulinum toxin causes a shift in this deterioration, expression of enhance actin and associated protein polymerization, with rejuvenation and reversal of vital structures of the apex of the retinal pigment epithelium causing cessation of the degeneration and deterioration of the maintenance role of the choroid and retinal pigment epithelium on the neuro-retina.

Botulinum toxin species effects this change act on Rho kinase and ROCK intracellular systems achieving the shift in expression of mRNA toward vital protein expression causing a robust microvilli and reversing or impeding atrophic shift and apoptosis of RPE cells involved in macular degeneration. In genomic studies using neural ganglion with assessment using robust cDNA fragments on gene chips, botulinum toxin has elicited a mRNA response which regulates production of proteins important to actin expression, cell to cell adhesion molecules and anabolic proteins governing enhance cell structures. Photoreceptor proteins have been shown to shift expression after botulinum toxin infusions into cell cultures.

Duration of Action

The disclosed formulations and methods may provide a biologic effect which enhances duration of action over existing therapies, with possible effects lasting between 4-50 weeks and possibly longer upon repeated injections. The increased duration may allow for fewer invasive procedures needed to administer the drug when intra-ocular injections are used. Botulinum toxins have varying durations in clinical practice dependent on the target tissue. The autonomic nerve effects can last longer than the effect on heavily myelinated motor nerves. Most of the nerves within the choroid have minimal myelination and many represent autonomic nerves from ganglionic structure outside the orbit and accessible to injection with a botulinum formulation described herein. Accessing the macular eye without orbital injection, high dose surface applications, intra-ocular implant or injection procedures, but instead through extra-orbital and para orbital injections, is an advantageous feature of the presently disclosed methods. Additionally, the presently disclosed methods can also limit neuromuscular paralysis of the extra-ocular muscles, which can cause vision-destroying diplopia and/or ptosis.

The duration of action of anti-VEGF agents (both FDA approved and in development) have targeted longer duration of action as the need for intra-ocular injection is associated with many complications. Fewer injections or a period of time is more comfortable for a patient and reduces administration risks. The half-life of the aflibercept EYLEA® in rabbit is about 7 days. In contrast, 0.5 mg of ranibizumab (Lucentis®) is about 2.88 days and 1.25 mg of bevacizumab (Avastin®) is 4.3 days.

Given botulinum toxin-based pharmaceuticals have intrinsically long duration of action, fewer injections may be needed as compared to known anti-VEGF agents. Further, botulinum toxin can increase the efficacy and duration of action of existing anti-VEGF therapies, allowing for fewer invasive intra-ocular injections. This was an unexpected result and indicates a unique and unanticipated effect of botulinum administration with paraorbital injections. Further cases have demonstrated increased duration of action of anti-VEGF agents. Botulinum formulations can also act on regulators targeted by anti-VEFG receptors, including various forms of tyrosine kinase enzyme pathways, which suppress VEGF activity membrane permeability, cell transformation and migration, particularly at the choriocapillaris and retinal pigment epithelium.

This potency enhancement of anti-VEGF agents has been seen in several experimental examples provided herein (see, for example, Example 8). For neuromuscular effect, duration of action is generally between 10-14 weeks. With some preparations, duration as long as 20 weeks between treatments may be possible. Further, for autonomic effects, durations for up to 24 weeks have been recorded. As botulinum technology offers superior duration over the currently used and anticipated with anti-VEGF pharmaceuticals, the convenience for patient treatment, with marked risk reduction and the possibility of additive effects are clear advantages. Further anti-VEGF agents have been associated with vaso-occlusive disease (e.g., stroke and arterial occlusions). Despite complications with anti-VEGF agents, assessments with botulinum toxin have not resulted in any serious reported complications at conventional dosing levels (as defined by FDA-approved dosings). Botulinum toxin-based pharmaceuticals as described herein can act similar to anti-VEGF agents and, in some embodiments, can increase potency and duration of ant-VEGF agents (see Example 1).

Dosing

The disclosed therapeutic formulations may, in some embodiments, include botulinum toxin or a fragment thereof. Any suitable form of botulinum toxin may be used in the disclosed formulations, for example, the disclosed formulations may include botulinum toxin A1-A5, B, C1-3, D, E, F, G and H. Additionally, fermentation yields with higher LD 50 units per cc of fluid may be used as a source of botulinum toxin, with or without complexing proteins. In some embodiments, fragments of botulinum toxin may include formulations devoid of neuromuscular junction activity. As will be understood, formulations devoid of neuromuscular junction activity may avoid muscle contractility weakness and complications caused by paralysis (e.g., diplopia, ptosis, dysphagia, facial paralysis and asymmetry, lagophthalmos, jaw and chewing weakness, and other forms of muscles weakness).

The disclosed formulations can be prepared with an appropriate dose of botulinum toxin. For example, in some embodiments, the disclosed formulations may be administered to a patient according to one or more of the following dosings:

0.01 to 0.5 LD 50 units, administered via intra-ocular, extra ocular, peri orbital, subconjunctival peribulbar injection, epibulbar injection, or topically.

0.5 to 5 LD 50 units, administered via intra-ocular, extra ocular, peri orbital, subconjunctival peribulbar injection, epibulbar injection, or topically.

5-10 LD 50 units, administered via intra-ocular, extra ocular, peri orbital, subconjunctival peribulbar injection, epibulbar injection, or topically.

10-20 LD 50 units, administered via intra-ocular, extra ocular, peri orbital, subconjunctival peribulbar injection, epibulbar injection, or topically.

20-40 LD 50 units, administered via intra-ocular, extra ocular, periorbital, subconjunctival peribulbar injection, epibulbar injection, or topically.

40-80 LD 50 units, administered via intra-ocular, extra ocular, periorbital, subconjunctival peribulbar injection, epibulbar injection, or topically.

80-160 LD 50 units, administered via intra-ocular, extra ocular, peri orbital, subconjunctival peribulbar injection, epibulbar injection, or topically.

160-320 LD 50 units, administered via intra-ocular, extra ocular, peri orbital, subconjunctival peribulbar injection, epibulbar injection, or topically.

320-640 LD 50 units, administered via intra-ocular, extra ocular, peri orbital, subconjunctival peribulbar injection, epibulbar injection, or topically.

640-1280 LD 50 units, administered via intra-ocular, extra ocular, subconjunctival peribulbar injection peri orbital, subconjunctival peribulbar injection, epibulbar injection, or topically.

0.5-25,000 LD 50 units, administered via intra-ocular, extra ocular, subconjunctival peribulbar injection peri orbital, subconjunctival peribulbar injection, epibulbar injection, or topically.

0.01 to 3,000 LD 50 units, administered via intra-ocular, extra ocular, subconjunctival peribulbar injection peri orbital, subconjunctival peribulbar injection, epibulbar injection, or topically.

1280-6,000 LD 50 units, administered via intra-ocular, subconjunctival peribulbar injection peri orbital, subconjunctival peribulbar injection, epibulbar injection, or topically.

In some example methods, conventional dosing of botulinum toxin may be used. As used herein, the term "conventional dosing" refers to any FDA-approved dosing of botulinum toxin for an indication of the head or neck. In select embodiments, 300 LD 50 units or less of botulinum toxin may be administered to a patient. For botulinum toxins with lower LD 50 potency, conversion assessment and table subject to existing dose conversions may be used. These example doses are given for a conventional form of botulinum toxin marketed using the trademark BOTOX®.

Conversion Table for Other Forms (Immunotypes, Formulations) of Botulinum Toxin

1. Xeomen:Botox—about 1:1 to 1.5:1.0 (Botox® more potent)
2. Dysport:Botox—about 3:1 to about 7:1 (Botox more potent per unit)
3. Mybloc:Botox about 50:1 to about 100:1 (Botox more potent)

Topical and Subconjunctival Administration

As described herein, clinical efficacy can be derived from topical application of botulinum toxin based pharmaceuticals. Dosing can range from 1-2500 Units using the botulinum toxin with complex. In order to reduce unwanted toxicity, the botulinum toxin protein molecule can be modified so as to reduce or eliminate the neuro-muscle effect so when applied to a mucous membrane surface like the ski, conjunctiva, or mucosal surfaces in the sinus nose, or mouth paralytic or weakening side effect do not occur. Further adjuvant protein can be removed so as to limit toxicity from gastro-intestinal absorption by eliminating botulinum toxin derived hemagglutinin protein represent as the botulinum toxin complex (e.g., BOTOX®). As dosing is determined by LD 50 in Swiss Webster mouse, units generally are accepted but may be converted into alternate forms such as derived from alternate assay or quantitative method.

Importantly, permeators such as lidocaine, albumin, polylysine, or mechanical devices such as contact lens, intra-ocular implants, subconjunctival implants, can be used to provide a delivery system appropriate for intra-ocular administration. Transconjunctival administration through lid or bulbar conjunctiva can be used. Drying techniques of the ocular surface can also be used to enhance penetration. Use of goggles which enhance permeation of the ocular surface can be employed to provide a positive pressure atmosphere or hyperbaric state such as used in hyperbaric oxygen chambers. Micro punctures of corneal and conjunctival epithelial followed by botulinum toxin based protein with or without contact lenses can increase corneal and ocular penetration. Varying concentration allowing for more effective uptake of the internal eye can be employed based on the specific stage of macular degeneration and based on specific pathologic findings clinically or SD-OCT.

It should be noted that subconjunctival injections, although not intra-ocular, place botulinum toxin next to extra-ocular muscles. If a neuro paralyzing formulation is used, any dosages above 2-5 (Botox®) units or dosing equivalents may induce the complications of diplopia and ptosis.

Intra cameral (aqueous humor) injections are known to be safer than intravitreal injections and can provide a superior method of increasing intra-ocular botulinum concentrations, with less chance of damage to intra-ocular contents.

It is important to note that, although the present disclosure often refers to methods that include injections of botulinum neurotoxin, in select embodiments, botulinum neurotoxin and/or preparations containing botulinum neurotoxin may be administered to a patient using alternative delivery methods, such as topical application. In select embodiments that include topical application, botulinum neurotoxin may be administered in dosing ranges of at least 20, at least 25, at least 30, or at least 35. Numerous configurations and variations are possible and contemplated.

Timing and Use of Botulinum Toxin in Conjunction with Conventional Anti-VEGF Drugs Used to Treatment Macular Degeneration Wet macular degeneration (as shown in FIG. 3) can be treated using drugs such as Avastin®, Lucentis®, EYLEA®, and abicipar (Allergan). These current drugs include different antibodies to various isoforms of vascular endothelial growth factors (VEGF), which cause recession of the developing neovascularization and/or leakage, resulting in return or stabilization of vision with partial restoration of the structural derangement in the retina with reduction in sub-retinal sub RPE, and intra retinal fluid. Botulinum toxin reparation described herein can be given prior to an intra vitreal anti-VEGF agent, simultaneous in an extraocular (e.g., para orbital or peri orbital type injection), or after an intravitreal injection. The timing of various treatments may be important as intravitreal anti-VEGF type agents and injections have a short duration of action relative to botulinum toxin preparations. While the onset of activity of a botulinum agent can vary, botulinum toxin can be placed in an optimal phase relative to activity onset of an anti-VEGF agent to enhance potency. Examples 1 and 8 described below in detail demonstrate enhanced anti-VEGF potency induced by a botulinum toxin preparation. As more fully described with respect to Example 8, administration of a botulinum toxin preparation may allow for complete removal of sub-retinal fluid when given prior to a single administration of an anti-VEGF agent, such as avastin or afibercept. The data obtained demonstrates anti-VEGF potency enhanced by prior or simultaneous use of botulinum toxin preparations. Enhancement in anti-VEGF potency can be a valuable improvement in clinical practice in unresponsive patients with wet (exudative) macular edema or any leakage from retinal diseases described herein. Potency enhancement can be made both with prior applications or simultaneous application of botulinum toxin using methods described herein. Such methods include but are not limited to para orbital injection of botulinum toxin preparations, which pose no side effects of diplopia, ptosis, or any orbital or facial muscle weakness.

Furthermore, potency enhancement of anti-VEGF agents can be advantageous for many reasons. For example, a longer duration of action of any anti-VEGF agent (in current use or in future development) will result in fewer loading doses of intra-ocular anti-VEGF agents being needed. Reducing the number intra-ocular injections needed can also cause fewer intra-ocular injections of a glucocorticoid or glucocorticoid slow-release implantation device, should a glucocorticoid agent be used in the macular degeneration treatment. The use of a botulinum toxin-based agent for the treatment of exudative macular degeneration can also be helpful for use in "treat and extend" or pro re nata (PRN) treatment regimens.

The disclosed botulinum toxin-based preparations and methods disclosed herein can be used for duration enhancement and potency-enhancing effects on currently used anti-VEGF agents. The disclosed methods and preparations can, in some embodiments, improve and reduce the cost burden on Federal insurance programs, such as Medicare and Medicaid, as well as private insurance companies, by reducing the number of procedures needed to treat this common cause of blindness. Reduction in intra-ocular injections can also reduce resource costs and, most importantly, make the treatment program safer for patients.

In some embodiments, the disclosed methods involve measuring the impact of patient care by frequency of needed injections based on various forms or ocular coherences tomography (OCT), visual testing, fluorescein angiography of the retina, and fundus photography. Reduction in frequency of intra-ocular injections, particularly using anti-VEGF agents, is a durable measurement for treatment enhancements and can be tested against saline controls. Further, duration of an anti-VEGF agent after loading dose can be a direct measure of benefit against saline controls. Reducing the frequency of intravitreal injections and the extent and amplitude of fluid reduction in the macula as well as the duration of effect after a determined loading dose of an anti-VEGF agent is administered by intra-ocular injections can also be used to determine efficacy of the treatment applied. Onset of effect of an anti-VEGF can also be measured with a botulinum toxin using various forms of OCT measurement and compared against suitable controls. Case studies described herein have indicated longer than expected results in patients with wet and exudative macular degeneration. Additionally, more rapid responses to anti-VEGF agents were observed than expected and a reduction in intra-ocular anti-VEGF injection over an extended period of time were also observed.

Drugs in Trials for Dry Non-Exudative and Wet Exudative Stages of Macular Degeneration Tables 1 and 2 outline various agents in trials or being contemplated for trials for the treatment of dry macular degeneration.

TABLE 1

Summary of Clinical Trials Targeting Macular Degeneration

| Drug/Therapy | Mechanism of Action | Route of Administration | Study Group/Sponsor | Clinical Trial Number |
|---|---|---|---|---|
| Photoreceptor and RPE preservation | | | | |
| Trimetazidine | Anti-ischemic agent with cytoprotective effects | Oral | Institut de Recherches Internationales Servier | |
| Alprostadil (prostaglandin E1) | Increase choroidal blood flow | Intravenous | UCB Pharma | NCT00619229 |
| Moxaverine | Nonselective phosphodiesterase inhibitor | Oral | Medical University of Vienna | NCT00709449<br>NCT01629680<br>NCT00709423 |
| Sildenafil | Phosphodiesterase type-5 inhibitor | Oral | Duke University | NCT01830790 |
| MC-1101 | Increase choroidal blood flow | Topical | MacuCLEAR. Inc. | NCT01601483 |
| Ozonated autohemotherapy | Increase oxygenation | Autohemotherapy | | |
| Fenretinide | Visual cycle modulator | Oral | Sirion Therapeutics | |
| ACU-4429 | | Oral | Acucela Inc. | NCT1802866 |

TABLE 1-continued Summary of Clinical Trials Targeting Macular Degeneration

| Drug/Therapy | Mechanism of Action | Route of Administration | Study Group/Sponsor | Clinical Trial Number |
|---|---|---|---|---|
| Tandospirone | Neuroprotection | Topical | Alcon Research | NCT00890097 |
| CNTF (NT-501) | | Intravitreal implant | Neurotech Pharmaceuticals | NCT0044954 |
| Brimonidine | | Intravitreal implant | Allergan | NCT00658619 |
| RN6G | Anti-amyloid antibodies | Intravenous | Pfizer | NCT01577381 |
| GSK933776 | Anti-amyloid B antibodies | Intravenous | GlaxoSmithKline | NCT01342926 |
| Doxycycline (Oracea) | Promotes photoreceptor survival | Oral | Paul Yates, MD, PhD., University of Virginia | NCT01782989 |
| Prevent oxidative stress injury | | | | |
| AREDS formulation | Antioxidant | Oral | National Eye Institute | NCT00345176 |
| Crocetin | Reduces apoptosis, increases oxygen diffusion through plasma, reduces lipid peroxidation, upregulates trophic factors | Oral | | |
| Curcumin | Reduces lipid peroxidation and formation of reactive oxygen species, modulating the expression of many oxidative stress-regulating genes, such as PDGF, VEGF, HO1, and others | Oral | | |
| Vitamins B9, 12, 6 | Decrease serum homocysteine levels | Oral | | |
| Resveratrol | Modulates cell proliferation, apoptosis, and angiogenesis | Oral | | |
| Inflammatory Suppressors | | | | |
| Eculizumab (SOLIRIS) | Humanized monoclonal antibody targeting complement 5 | Intravenous | Philip J. Rosenfeld, MD, Ph.D., University of Miami | NCT00935883 |
| ARC-1905 | Peylated RNA aptamer targeting complement 5 | Intravitreal injection | Ophthotech Corporation | NCT00950638 |
| FCFD4514S (lampalizumab) | Humanized monoclonal antibody antigen-binding fragment targeting complement FD | Intravitreal injection | Genentech, Inc. | NCT01602120 |
| LFG316 | Humanized monoclonal antibody targeting complement 5 | Intravitreal | Novartis Pharmaceuticals | NCT01527500 |
| Glatriramer acetate (copaxone) | T cells and inflammatory suppressor | Subcutaneous | The New York Eye and Ear Infirmary | NCT00541333 NCT00466076 |
| Flucinolone acetonide (iluvien) | Corticosteroid | Intravitreal implant | Alimera Sciences | NCT00695318 |
| Sirolimus (rapamycin) | mTOR inhibitor | Subconjunctival | National Eye Institute | NCT01445548 |
| Lipid metabolism | | | | |
| Statins | Lowering lipid accumulation in Bruch's membrane | Oral | | |
| Heparin-induced extracorporeal lipoprotein precipitation | Reduces serum LDL, fibrinogen, lipoprotein | Extracorporeal circulation | B. Braun Avitum AG | NCT01840683 |

RPE: Retinal pigment epithelium,
LDL: Low-density lipoprotein,
CNTF: Ciliary neurotrophic factor,
AREDS: Age-Related Eye Disease Study,
PDGF: platelet-derived growth factor,
VEGF: Vascular endothelial growth factor,
HO1: Heme-oxygenase-1,
FD: Complement factor D

TABLE 2

Summary of Clinical Trials Targeting Geographic Atrophy

| Target | Treatment | Clinical trial number | Company | Status of clinical trials |
|---|---|---|---|---|
| Anti-inflammatory | Eculizumab | NCT00935883 | Alexion Pharmaceuticals (Cheshire, CT) | Completed phase II |
| | Sirolimus | NCT00766649 | National Eye Institute (Bethesda, MD) | Completed phase I/II |
| | Lampalizumab | NCT02247479 | Hoffmann-LaRoche (Basel, Switzerland) Roche (Basel, Switzerland) | Phase III currently recruiting |
| | ARC-1905 | NCT00950638 | Ophthotech (Princeton, NJ) | Completed phase I |
| | Glatiramer Acetate | NCT00541333 | The New York Eye & Ear Infirmary (New York, NY) | Phase I suspended participant recruitment |
| Antioxidants | AREDS2 | NCT00345176 | National Eye Institute (Bethesda, MD) | Phase III completed |
| | OT-551 | NCT00306488 | National Eye Institute (Bethesda, MD) Othera Pharmaceuticals (Exton, PA) | Phase II completed |
| Visual cycle inhibitors | Fenretinide | NCT00429936 | ReVision Therapeutics, Inc. (San Diego, CA) | Phase II completed |
| | Emixustat Hydrochloride (ACU-4429) | NCT01802866 | Acucela Inc. (Seattle, WA) | Phase II/III ongoing |
| | ALK-001 | NCT02230228 | Alkeus Pharmaceuticals, Inc. (Boston, MA) | Phase I completed |
| Amyloid beta | MRZ-99030 | NCT01714960 | Merz Pharmaceuticals GmbH (Dessau-Roßlau, Germany) | Phase I completed |
| | RN6G | NCT01003691 | Pfizer (New York, NY) | Phase I completed |
| | GSK933776 | NCT01342926 | GlaxoSmithKline (Brentford, UK) | Phase II ongoing |
| Choroidal perfusion | MC-1101 | NCT02127463 | MacuCLEAR, Inc. (Plano, TX) | Phase II/III currently recruiting |
| Stem cell therapy | MA09-hRPE | NCT01344993 | Ocata Therapeutics (Marlborough, MA) | Phase I/II currently recruiting |
| | MA09-hRPE | NCT01674829 | CHABiotech CO., Ltd (Seoul, South Korea) | Phase I/IIa currently recruiting |
| | HuCNS-SC | NCT01632527 | StemCells, Inc. (Newark, CA) | Phase I/II ongoing |

It is of note that there are no clear agents that consistently work for repressing or stopping dry macular degeneration. Also of note is the fact that no contemplated treatment agents contemplate a botulinum toxin-based pharmaceutical for the treatment of dry or wet degeneration. The mechanisms of action are also listed in Tables 1 and 2. Note that anti-VEFF, choroidal flow enhancers, anti-amyloid antibodies, visual cycle modulators, antioxidants, apoptosis modulators, a number of anti-complement directed antibodies, neuroprotectors, nerve growth factor, phosphodiesterase inhibitors, stem cells, and anti-inflammatory agents are being tried. However, no review or study either contemplated or provided rationale or reduction to practice of a botulinum toxin-based pharmaceutical. Most recently, Lampalizaumab (Genetech, Inc.) has been reported to fail at the 2017 American Academy of Ophthalmology in New Orleans. Recently, studies involving inserting intra-ocular implants complexed with corticosteroids for slow release have been added to Anti-VEGF agents (e.g., EYLEA®) for wet macular degeneration treatment. Further, newer agents, such as angiopoietin, are being tried with anti-VEGF agents to increase potency and duration of action of intravitreal drugs.

At a 2017 Retina meeting, a review of eye delivery mechanisms was conducted which failed to cite trans neural delivery mechanism for the treatment of choroidal or retinal diseases, including AMD. The void gives credence to this novel component to formulations and treatment methods described herein (e.g., trans neural delivery of botulinum or its components to the choroid and choroidal ganglion, with favorable effects on RPE and neuroretina).

Pharmacodynamic Delivery System for the Treatment of Human Macular Diseases (Axoplasmic Flow from Extra-Ocular Injections)

Described herein is not only a unique agent but a unique delivery system for the treatment of human macular diseases. Botulinum toxin has the ability to diffuse from the injection sites affecting a regional biologic effect that is directly and volumetrically related to dose. Biologic effects on structures can be accomplished additionally by retrograde and ante grade axoplasmic flow through autonomic, sensory and motor nerves causing a change by genetic upregulation of proteins governing cell to cell adhesions such as actin, various cadherins, and having a direct action to upregulate structural proteins governing membrane barrier functions, cells adhesion to basement membranes and differentiation of the polarity of epithelial cytoplasm relating to the function of the epithelial barriers. The unique feature is very useful in that intravitreal injections may not be necessary, in some embodiments. Elimination of this step in the treatment of macular degeneration may reduce of eliminate the risk of vitreous hemorrhage, endophthalmitis, retinal detachment, traumatic cataract formation, glaucoma, retinal breaks, and pain associated with a direct injection into the eye. These complications can be devastating and may result in blindness.

A pharmacologic effect from injection of soft tissues around the eye is not associated with the more serious, potentially blinding, complications which can occur with direct injections into the eye. These injection locations may be less painful as well. Dosing of the disclosed formulations can vary between 1-3000 units, preferably 1-300 units and more preferably 1-200 units (BOTOX®). Higher dosing can be used with less potent formulations (Dysport, Xeomen, Myobloc or other preparations). The injections are generally given over the regions involving motor and sensory nerves which enter the eye, especially the trigeminal nerve, oculomotor nerve, and most particularly autonomic nerves such as the pterygopalatine ganglion under temporalis muscle. Transport via venous system is also possible as periocular tissue in the forehead, lids and immediate surrounding anatomic regions drain directly into the orbit with collateral flow into the eye. Autonomic nerves also supply the human eye (pupillary fibers) and transport via collateral autonomic nerves can act as a conduit for a biologic intra-ocular effect delivery from nerves penetrating the poster eye pole overlying the macular (see figure of orbital dissection). This conduit offers a passage for low concentration delivery of botulinum or its fragments to the choroid and retinal pigment epithelium, possibly in concentrated forms. Sensory nerves can further this conduit to the target retinal pigment epithelium. Transcytosis is possible with penetration of botulinum material by retinal pigment epithelial and neuro retinal structures affecting both blood vessel responsiveness to vascular endothelial growth factors, vascular permeability, barrier integrity of the retinal pigment epithelium, and potential for leakage and new blood vessels growth from immunologic cytokines emitted from loss of integrity of the RPE barriers. This process allows botulinum toxin to enhance cell to cell adhesion via possibly modulating action on Rho kinase, ROCK, and other proteins critical in maintaining the RPE actin cytoskeleton, cell to cell adhesion molecules, cell to basement membrane adhesion molecules, and endothelial adhesion molecules rendering the biologic RPE barrier function more robust and inert as well as improve physiologic functions such as processing, catabolizing and removing rhodopsin protein. Further, the effect of the botulinum toxin may prevent vascular leakage and/or diminish and stabilized vascular endothelial growth. Such an effect can also involve the retino-vascular blood retinal barriers as occurs in macular edema from inflammation and diabetes. Additionally, autonomic nerves have been shown to integrate with choroidal autonomic ganglion cells under the macular.

Prior to the filing of the subject application, the intra-ocular effects of botulinum toxin on RPE-retina were unknown. Moreover, it was not known that injections of botulinum into skin of lids, face, forehead, facial bones, facial and jaw muscles, scalp sinus mucosa, nasal mucosa, neck, mouth or palate and in autonomic parasympathetic and sympathetic ganglion which project axons into the eye had any effect whatsoever on the RPE/choroid. This information alone is novel and, in combination with the disclosed formulations and methods can provide safer administration paradigm than intra-ocular injections.

With respect to dosing using BOTOX® or other botulinum formulations (e.g., Dysport, Xeomen), a large dosing can be given in the para orbital region with causing diplopia. The pterygopalatine region is in close proximity to the inferior orbital fissure, which directly communicates into the orbital. Doses under 200 units applied under facial muscles in the temporal region have not led to botulinum diffusion and neuro muscular paralysis of extra-ocular muscles, causing diplopia. As this is an open anatomic region, a contrary effect with large dosing would be anticipated. In over 77 injections given by the inventor to patients, no diplopia has been encountered with dosings of less than 200 units.

Penetration of the Internal Eye by Peri Orbital and Peri-Ocular Injections

Another unique aspect of the disclosed therapeutic formulations and methods is that an effect on the internal eye in the macular region can be achieved by a peri-ocular or peri-orbital injection. Not to be limited to the high dose effects gained by pars plantar injection (discussed with respect to other embodiments), the opportunity to gain entrance into the eye by per-orbital lid, or peri-ocular and neck injections using axoplasmic transport is an operational improvement which avoids serious complications of other methods. Extraocular injections would easily be possible and much easier for patients. Extra-ocular injections targeting upstream nerves remote from the eye which eventually enter the eye allows for selective effect on intra-ocular contents without subjecting muscle tissue to the effects of the toxin causing extra-ocular muscle weakness with diplopia and ptosis. Positioning the injection needle deep into the orbit with resulting botulinum toxin-induced paralysis of the extra-ocular muscles may be undesirable. The risk of repeated intra-ocular injections which can cause intra-ocular hemorrhage, eye destroying endophthalmitis, retinal detachment or retinal breaks, lens dislocations, or increases in intra-ocular pressure. The toxin can reach the targeted choroid, retinae by unique mechanisms such as axoplasmic flow, venous retrograde diffusion, and/or direct diffusion from peri-ocular and paraorbital injections. These indirect mechanisms for the treatment of AMD and associated conditions afford a selective entry into the eye, novel in itself, via nerve transport to avoid undesirable side effects from muscle weakness.

Notably, the choroid nerve fiber structure has proven to be positive for a number of neuropeptide and related neurotransmitters. With age, there has been noted to be a recession of nerves in the choroid in close approximation to the retinal pigment epithelium. Such denervation can render a trophic effect on structure and function of the retinal pigment epithelium to cause RPE dysfunction, loss of cell to cell adhesion and loss of vital RPE barrier function, as well as other structure and functional degenerative changes. Certain neurotransmitters, nerve peptides, present in the choroid can be vital to epithelial health and function. Recession and depletion of such chemicals can result in atrophy, mesenchymal and migratory changes in the RPE, loss of RPE-photoreceptor interplay and ultimately photoreceptor damage with loss of retinal function and vision.

In the ocular surface case presented in the examples (filamentary keratitis), loss of barrier function with cell to cell adhesion and epithelial cell adhesion to basement membrane strands of corneal epithelium break off form filaments exposing corneal sensory nerves resulting in pain and pathologic reactive changes (neovascularization). Filamentary keratitis is a common problem with corneal denervation and a condition called neurotrophic keratitis. Neurotrophic keratitis results from damage to sensory nerves from trauma, recurrent infection with neurotrophic viruses (e.g., herpes simplex, herpes zoster), chronic infections, dry eyes, with mucous and tear deficiencies. The epithelium is often degenerated prior to loss of corneal epithelium and neovascularization, a in a manner similar to macular degeneration. In the case described herein, topical botulinum toxin resulted in repair and mitigation of the filaments in a time course consistent with known botulinum pharmacokinetics and with repeated efficacy. Botulinum here is causing increased cell adhesion to surrounding cells and basement membranes and stimulating nerve structures in a fashion favorable to corneal epithelial function and elimination of filaments breaking off the continuous corneal epithelial sheet. Botulinum stimulates nerve/epithelial structures to produce actin and related adhesion molecules to that epithelium barrier function and structure is facilitated and sensory nerves function is at least partially restored over the pathologic state.

The epithelial discontinuity in such cornea cases proceeds to growth of new vessels. In the case of macular degeneration, the stage 1 dry form of macular degeneration precedes the growth of new vessels which destroys the RPE-photoreceptor interface leading to blindness. Avoiding the discontinuity by enhancing nerve fiber effect from choroidal axons and ganglion cells is a mechanism described herein which is useful for the treatment of macular degeneration. The botulinum enhanced choroidal nerve fiber effect on the RPE provides function stability to the RPE allowing for enhancement of barrier function, maintenance and prevention of degeneration of the retinal pigment epithelium with time. Defects in the choroidal innervation results in loss of important chemical derived from peripheral nerves vital to RPE health. Loss of certain neuropeptides such as vaso-active intestinal peptide (VIP), have been known to be depleted in cases of macular degeneration. Leaching of the toxin through the RPE or nerves surrounding arteries entering the eye can also have an effect to seal leakage from retinal arterioles, leading to the treatment of retino-vascular leakage.

Botulinum toxin by stimulation of peripheral sensory nerves to sustain and stimulate vital intra cytoplasmic structures, such as formative actin molecules, and associated proteins, adhesion molecules, and neurotransmitters and RPE can be vital to maintaining RPE and delaying the effects of macular degeneration. Botulinum toxin has a potent effect to stimulating actin-actin associated proteins formation on peripheral motor nerves and such effects can carry over to the peripheral nerves penetrating the human eye.

Safety

Utilizing peri-ocular botulinum toxins is also safe. For cosmetic, facial movements diseases (hemifacial spasm, blepharospasm, Meiges syndromes, dystonia, bruxism, migraine, tension headache), crows feet, forehead lines, glabellar lines, induced ptosis, facial inflammatory states, well-established dosing parameters have been designed to provide an exquisitely high safety record. As the material is known to be very safe after repeated injections, the unique opportunity is present to provide patients with retina and macular diseases a superb opportunity to understand the risks benefits over existing FDA approved drugs (Eylea®, Lucentis®, and Avastin®). Most of the studies done over the last 3 decades have had safety eye exams and no serious irreversible eye complication has been identified. This opportunity is truly unique for clinical studies and will serve as an impetus to proceed using various endpoints such as acuity (such as defined in ETDRS-early treatment diabetic retinopathy study) and other endpoints mentioned herein.

The disclosed methods can limit applications of anti-VEGF agents (via intravitreal injections) and enhance potency of these anti-VEGF agents, which can lead to enhanced duration of action. Moreover, this synergism serves to decrease the frequency of intra vitreal injections (thus increasing safety by limiting the number of surgically-driven eye stabs) and increasing patient comfort. The disclosed methods can also decrease the use of expensive agents for patient and government insurance agencies (such as Medicare), allowing less expensive agents to achieve a potency and duration improvement over current (even long-acting) agents.

When a botulinum product is used in conjunction with an intravitreal anti-VEGF, it can be given prior to the intravitreal injection or after the intravitreal injections, in some embodiments. Repeated injections of botulinum toxin can be given for years with high levels of safety.

Trans-Neural Delivery to the Maculae

In some embodiments disclosed herein, the peripheral nerves are utilized as a conduit to deliver botulinum toxin-based pharmaceutical into the eye, retina and/or macula without using a direct intra-ocular injection (which inherently increases the risk of complications). The smooth muscle of the vessel walls of the choroid, like those of skeletal and cardiac muscle blood vessels are innervated by both divisions of the autonomic nervous system, which form dense plexuses of fibers around the vessels ("perivascular plexus"). Axon terminals are also found throughout the stroma, terminating on non-vascular smooth muscle, intrinsic choroidal neurons (ICNs), and possibly other cell types. There are also primary afferent sensory fibers that project to the trigeminal ganglion via the ophthalmic nerve; some of these give rise to peptide-positive collaterals that terminate on and around the vessels and intrinsic choroidal neurons.

Figure 6:
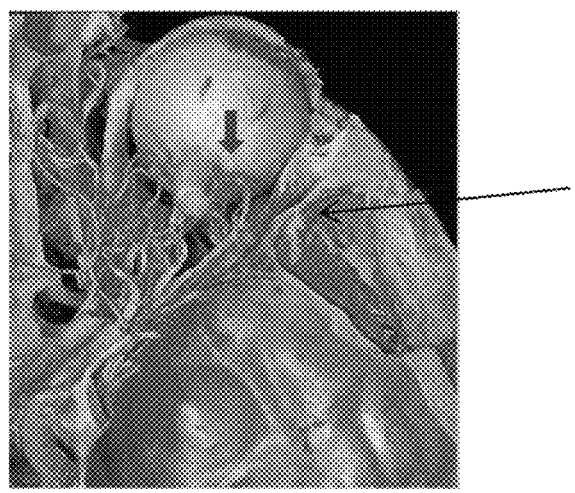
FIG. 6 illustrates a top view of a human dissection orbit with penetration of nerves and vessels into the posterior pole under the macula.

FIG. 6 illustrated a human dissection orbit from above. In FIG. 6, the thin dark arrow represents a needle placement next to orbit. Note proximity and presence of vessels and nerves in this region giving botulinum toxin formulations access to the posterior surface of sclera with nerve vessel penetration into macular and choroid-pigment epithelium. Injections target autonomic nerves and/or sensory nerves in the pterygopalatine fossa.

Figure 7:
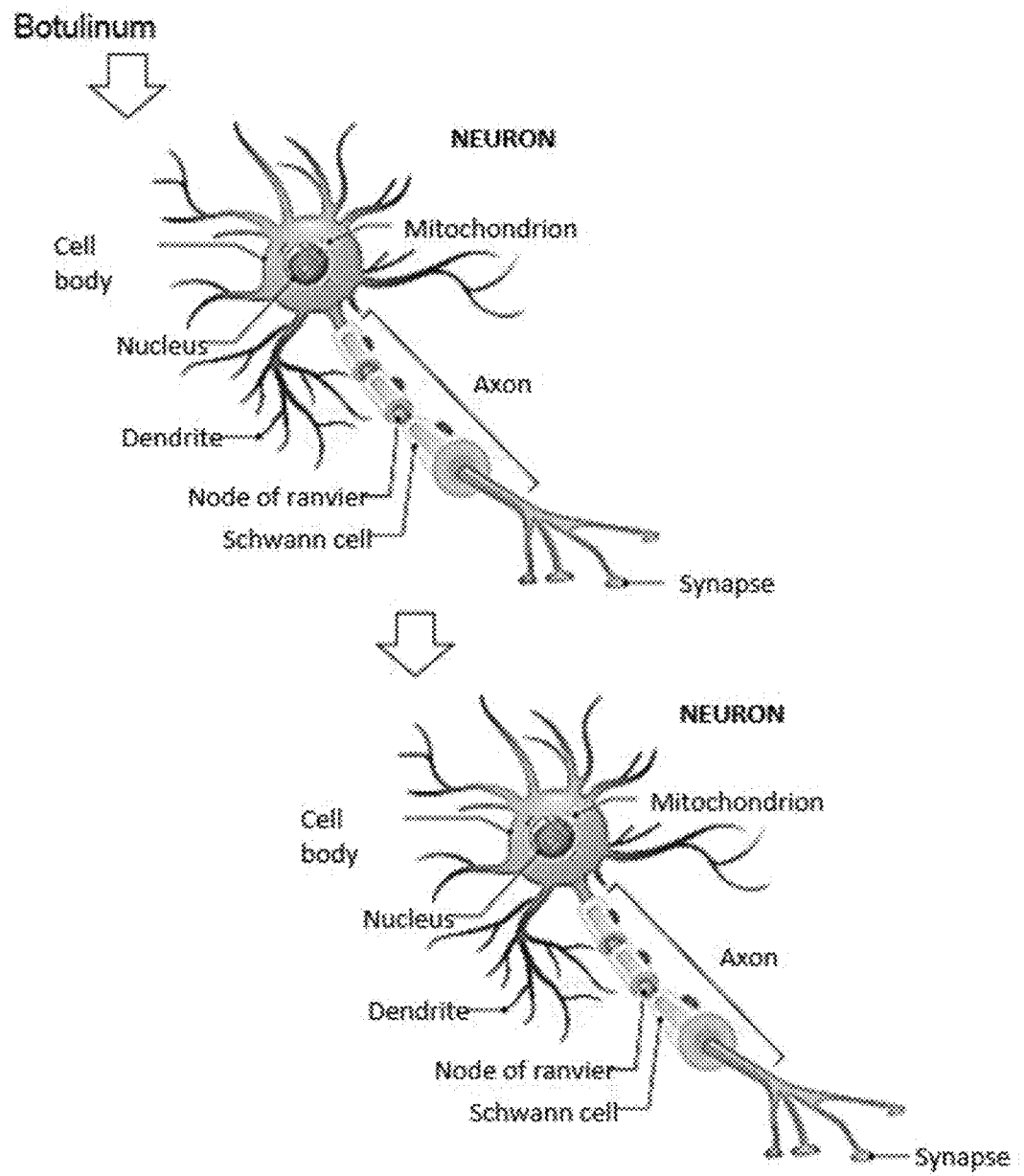
FIG. 7 illustrates extra-ocular administration followed by nerve penetration and transcytosis with eye penetration.

FIG. 7 illustrates extra-ocular administration followed by nerve penetration and transcytosis with eye penetration. Transport along axons in each direction and transcytosis to achieve penetration into the eye (choroid, retinal pigment epithelium and neuroretina). Dendrite-axon penetration, cells transcytosis to new axon and dendrite (retrograde penetration and transport) may also be utilized in some embodiments.

The main parasympathetic input to the choroid originates from the pterygopalatine ganglion located within the pterygopalatine fossa (FIG. 6). These fibers are predominantly cholinergic and are rich in the vasodilators vasoactive intestinal polypeptide (VIP) and nitric oxide (NO). These nerves are targets for botulinum toxin penetration and transport into the eye when injections are given into the region of the pterygopalatine fossa (outside the eye and orbit). The sympathetic innervation of the choroid comes from the superior cervical ganglion. These noradrenergic neurons terminate on the blood vessels and mediate vasoconstriction. This anatomic arrangement allows for neck injections penetrate the eye by axoplasmic flow.

The choroid has been shown to use peptides such as substance-P and calcitonin gene-related peptide in a precentral reflex arc, or axon reflex, a non-synaptic response in which a local stimulus (chemical or mechanical) depolarizes a sensory terminal which travels to the nearest collateral (branch), releasing the peptide onto the effector tissue. Evidence for this reflex has been found in the primary sensory afferents from the trigeminal ganglion in the uvea and choroid, which use both peptides; the reflex may mediate changes in blood flow or a variety of other functions. For instance, in both mammals and birds, sensory fibers projecting to the trigeminal ganglion from the choroid via the ophthalmic branch of the trigeminal nerve elicit vasodilation. These terminals are positive for substance-P and calcitonin-gene-related peptide.

Botulinum toxin may be transported via any peripheral neural path capable of collateral axoplasmic flow and, in some cases, can penetrate into the choroid and into retinal pigment epithelial structures via transcytosis to achieve a biologic effect on target tissues in the macula (see FIG. 7).

Venous delivery is not mutually exclusive of axoplasmic delivery to the eye. Diffusion into the cavernous sinus (venous sinus with carotid artery passing through the center) brings toxin molecules in proximity to the carotid syphon which contains sympathetic nerves throughout its surface (sympathetic plexus). Binding of botulinum to autonomic neurons surround the carotid artery surface in the cavernous sinus results in axoplasmic flow along the ophthalmic artery into the orbit and eventually into the posterior eye and maculae with an effect on neuromuscular junctions.

Veins drain from the periocular region nasal region and via inferior orbital fissure in proximity to the orbital veins in proximity to the vortex veins draining the internal eye. Venous anastomosis allows another conduit for delivery into the choroid and retina.

Axoplasmic Flow (Unique Conduit for Entry into the Choroid and Retina)

Early experiments with radiolabeled full length BoNT/A showed that the toxin is transferred to the ventral roots and adjacent spinal cord segments upon intramuscular injection in the cat gastrocnemius. Similarly, radiolabeled BoNT/A has been shown within the axoplasm of myelinated axons after its peripheral injection in mice. A dose-dependent retrograde transport of BoNT/A in brainstem motor neurons was also shown by electrophysiological and ultrastructural experiments in cats. Further segments of botulinum toxin have also been noted to undergo axoplamic flow (HcA segment). Both full length botulinum toxin and binding segmental forms can undergo long range transport via axoplasm. This phenomenon is exploited in one delivery mechanism demonstrated in the invention and case examples. In compartmentalized cultures of rat sympathetic neurons, BoNT/A moves retrograde into cell bodies when applied at high concentrations into the distal compartments. However, retrograde trafficking of BoNTs has been inferred mainly indirectly, i.e. by observing the appearance of radioactivity or BoNT-cleaved substrates away from the site of administration. Thus, the kinetics and intracellular pathways used by BoNTs for their long-range transport remains unclear but more recently tracking SNAP 25 lysis activity along the neurons axon and cell body over time has been helpful in substantiating initial observations. Transcytosis has been demonstrated and is operational in various embodiment of the invention.

In addition to axoplasmic transport and effects on choroid and retinal structures, botulinum toxin A or its segments and associated proteins can be used in unison or as part of a fusion protein complex involving anti-VEGF proteins to achieve higher and more sustained biologic effects to enhance barrier function, stop leakage and regress neovascularization and its pathologic effects, and/or alter intracellular RPE structural protein expression. A combined molecular approach provides for an alternate method for bringing an anti-VEGF drug to the choroid without and intra-ocular injection and using a carrier protein which further targets a cellular mechanism involving retinal pigment epithelial integrity. Such a formulation may involve use of one or more of the following: botulinum toxin (for instance, a subtype of type A) or fragment (for instance HcA, binding domain), a fusion addition of an anti-VEGF agent (for instance, a non-fused addition of an anti-VEGF agent, Avastin® or another fusion protein with anti VGF properties), and a stabilizing excipient known to facilitate stability and nerve cell axonal uptake.

The anti-VEGF agent can be delivered by botulinum or its fragments which participates by axoplasmic flow and undergoes transcytosis with the anti-VEGF agent causing a multifaceted mode of action causing reversal of leakage from new vessel growth, regression of new vessels, enhancement and promotion of a robust retinal pigment epithelium intercellular attachments to basement membranes and contiguous cells and a reversal of intracellular structural proteins which foster RPE degeneration. This formulation may also react with retino-vascular circulation to limit leakage from the retino-vascular capillaries and post capillary small veins.

The disclosed formulations may be used with conventional para plana injection, intra-ocular injection, or other types of extraocular injection. Additionally, in some embodiments, one or more fusion proteins and axoplasmic transport may be used to produce unique formulations. The disclosed formulations can be used with the conventional para plana injection (intra ocular) of anti-VEGF agents to produce a potency enhancement with respect to using a single anti-VEGF alone (see example), in some embodiments. Further, one or more anti-VEGF agents can be included with a botulinum toxin formulation described herein and applied via an extra-ocular delivery method (as described herein) to produce enhanced potency.

Para-Orbital Injection of Botulinum Toxin for AMD

As previously described, extra orbital injections of botulinum toxin can result in delivery of botulinum toxin to the macular via axoplasmic flow. An anatomic arrangement conducive to macular delivery involves placing the needle over the zygomatic arch aiming the bevel toward the pterygopalatine fossa and in proximity of the external portion of the inferior orbital fissure. The inferior orbital fissure extends very anteriorly (unlike the superior orbital fissure), allowing a 2 cm needle to very closely approach the fissure. Projection of the pterygopalatine ganglion, which projects through this fissure, supplies the globe and allow botulinum toxin close proximity to autonomic synapses as well as veins which drain toward the cavernous sinus. Penetration of botulinum toxin into the globe from this injection point may be facilitated by this anatomic arrangement. Toxin in cavernous sinus veins can infiltrate the sympathetic autonomic nerves on rout the retina via ophthalmic, retinal arteries and ciliary arteries (countercurrent movement of botulinum toxin nerve vs vein). The ganglion noted in the human choroid most likely picks up its innervation by the pterygopalatine ganglion. These ganglions are often seen in close proximity to the posterior pole of the globe. This unique injection location is devoid of major vessels and critical structures, resulting in a very low risk procedure. Sensory (V2) and autonomic nerves are closely abutting the fissure and the fissure may allow some orbital and globe penetration. In these and other embodiments, other para orbital areas may also be used as injection points.

Conversion Table:

For BOTOX®, 1 unit roughly corresponds to 3-7 units of Dystport 0.8-2 units of Xeomen, and 20-150 units of Myoblock. Other formulations may be tested with the conventional mouse LD 50 assay and converted to the LD 50 standard derived from the Hall Strain derived type $A_1$ for comparative unit potencies.

Rho Kinase

A unique aspect of the invention described herein is that type A botulinum toxin has Rho kinase modulating action and can affect expression of actin and cadherin important in preventing apoptotic changes in cell structure (programed cell death cycles). Botulinum type C3 has been long known to have highly significant Rho kinase activity. Herein the effect from immunotype A of botulinum toxin is achieving such effects similar and identical at regional dosing levels below necessary to cause muscle weakness with attendant dysfunction such as diplopia lid malposition's and eyelid weakness is an operational component of the invention. Rho Kinase can effectively interact with the actin cytoskeleton causing anabolic gene expression, enhancing rapid turnover and expression of actin in such as fashion as to alter and enhance cell, tissue and organ function. Effects on other ocular tissue pertinent to Retinal Pigment Epithelial Interaction (Filamentary keratitis) are discussed relative to Example 3.

The effect on epithelial barriers has been demonstrated in another ocular condition known as filamentary keratitis, which can serve as a surface model for the understanding effect on the RPE. This is a condition often associated with dry eye syndromes, and inflammatory syndromes characterized by epithelial strains separating from attachment to the epithelial sheet and underlying basement membranes. The process in a predisposed patient can be chronic and be associated with visual loss, pain, photophobia, and involuntary eyelid closure. Botulinum toxin has been used to close eyelids to treat various forms of corneal ulcers in the past to mimic a surgical tarsorrhaphy, an operation used to close the space between eyelids (palpebral fissure) and protect the ocular surface. In these descriptions, no mention has been made about the intrinsic effect on botulinum toxin on the epithelium, cellular structure of the epithelium, intrinsic effect of botulinum on cell to cell adhesion, cell to basement membrane adhesion from a direct effect of botulinum on adhesion molecules, or an effect on actin-cadherin proteins or any intra or extracellular proteins causing an increased cohesion of corneal epithelium Herein describes an intrinsic effect on corneal epithelium in which increases the cohesive integrity of corneal epithelial cells which improve symptoms of filamentary keratitis, with reduction and disappearance of filamentous. This condition has been treated by concepts describes herein with topical botulinum drops which gain access to the epithelial cells on the eye surface via topical application defects created by the disease. Botulinum toxin causes expression of actin, enhancement the expression and intra-cellular organization of actin, cadherin and associated proteins, which enhance epithelial cohesion and integrity causing diminished filament formation and disease improvement. A similar effect in achieve in macular degeneration which the retinal pigment epithelium achieves an increased integrity from promotion of cell to cell, cell to basement membrane and enhance specialization of intracellular-extracellular function created by the botulinum toxin based agent. With topical (eye drops) use of botulinum toxin, beneficial effects on epithelial structures can be achieved.

For filamentary keratitis, botulinum toxin is directly observed to:
1. Enhance epithelial sheet adhesion on the ocular surface using a slit lamp bi-microscope on the human eye
2. Decreased exposure of underlying nerves
3. Decrease corneal neovascularization in chronic conditions
4. Decrease pain from covering exposed nerve endings
5. Enhanced and rejuvenated microvilli on micro anatomic structure of the epithelial surface causing a vital enhancement of corneal integration with the tear film (needs for oxygen transportation). Such microvilli improvement can be useful in administering botulinum toxin for dry eye syndromes and inflammatory conditions of the ocular surface such as recurrent erosions.
6. Decreased incidence of recurrence Similar effects can be used to treat other forms of keratitis involving basement membrane such as recurrent corneal erosion, basement membrane dystrophy (map dot fingerprint dystrophy0, trophic corneal ulcers, herpes simplex keratitis, thyroid related eye surface disorders, corneal melt syndromes, chemical burns, ocular cicatricial pemphigoid, chronic dry eye syndrome, rosacea keratitis, Stevens Johnson syndrome, and exposure keratitis. Topical formulations can be devised as many of the aforementioned conditions occur on or near the ocular surface.

Topical formulations containing larger concentration of botulinum toxin can enter the eye and provide a superior method of administration over pars plana intra-ocular injections.

Botulinum Toxin Formulations

Example botulinum toxin formulations include type A1-5, B, C1-C3, D, E, F, and/or G botulinum toxin. Fragments of botulinum toxin may be used to elicit specialized cellular effects including isolated genomic expression of cellular constituents involved in enhancing barrier effects, actions on VEGF related pathways, interactions with presently available anti-VEGF drugs, structural proteins, regulators of structural proteins, and inflammatory regulating proteins. The disclosed formulations may, in some embodiments, include stabilizing proteins, poly cationic proteins or permeators (albumin or polycationic proteins), use of lidocaine within preparation or given prior to injections, protein derivative from botulinum with SNAP-25 interactive portions chemically removed, formulations with enhanced hemagglutinin protein typically found in the botulinum complex, enhancement with cadherin binding proteins or agents know to act on Rho kinase, upstream and downstream metabolite and (ROCK). Modulation of ROCK by botulinum toxin compositions described herein (e.g., type A toxin) contributes to therapeutic effects for many disease conditions described herein.

ROCK1 is a protein serine/threonine kinase also known as rho-associated, coiled-coil-containing protein kinase 1. Other common names are ROKβ and P160ROCK. ROCK1 is a major downstream effecter of the small GTPase RhoA and is a regulator of the actomyosin cytoskeleton which promotes contractile force generation. ROCK1 plays a role in cancer and in particular cell motility, metastasis, cells adhesion, and angiogenesis. ROCK1 has a diverse range of functions in the body. It is a key regulator of actin-myosin contraction, stability, and cell polarity. These contribute to many progresses such as regulation of morphology, gene transcription, proliferation, differentiation, apoptosis and oncogenic transformation. Other functions involve smooth muscle contraction, actin cytoskeleton organization, stress fiber and focal adhesion formation, neurite retraction, cell adhesion and motility. Modulation and/or inhibition of ROCK1 influences reduction of stress fiber formation in RPE cells. Stress fibers formed by actin condensation in the RPE cytoplasm often occurs in age related macular degeneration causing RPE barrier function disruption and downstream reactions including neo vascularization, impaired RPE fluid pumping activity, immune exposer of the neuro-retina, influx of neuropeptides, cytokines, and complement. Stress fibers in RPE cells are depicted in FIGS. 14A-14D, as well as in FIGS. 4C, 5A, and 5C. Furthermore, botulinum toxin formulations described herein can be considered to promote retinal neuronal regeneration by changing Rho activity. These formulations can include, in some cases, botulinum complex typically known as BOTOX® (type A botulinum toxin complex).

Formulations are preferably given by injection but may be delivered with an eye drop. Eye drop deliverer may vary between 10-10,000 units but preferable under 3,000 units. Alteration in dosing with different formulations can be derived from the literature.

Preferably, Type A (or subtypes) or type B would be used as the safety of dosing forms are well established for the existing preparations but other subtype and non-neuromuscular subtypes or chemically altered types of botulinum type A are anticipated to be useful.

A botulinum toxin formulation comprising only hemagglutinin proteins devoid of neurotoxin can also be used to isolate and enhance the effects of hemagglutinin on adhesion proteins such as cadherin isoforms and associated intracellular proteins so as to allow for greater biologic effects not limited by the weakening and paralytic effects of the neurotoxin. Further, in a unique embodiment, a formulation with neurotoxin with cleaved portion removing the SNAP-25 and neuromuscular weakening effect but preserving the effects on actin and cell adhesion function can be used for treatment. Such formulations have been cited and studied in past but have not been suggested for use in medical indications such as macular degeneration or use on membrane barrier functions beneficial for the treatment of disease described herein.

Formulation consisting of toxin derivatives with cleaved SNAP 25 activity can also be used as carrier molecules for anti-VEGF agents as well as in conjunction with accessory proteins.

A botulinum toxin formulation comprising enhanced quantities of botulinum related hemagglutinin proteins with neurotoxin can be used to isolate and enhance the effects on cadherin and related adhesion proteins and associated intracellular proteins so as to allow for greater biologic effects not limited by the weakening and paralytic effects of the neurotoxin. In some embodiments, some such botulinum toxin formulations can exhibit pharmacologic effects when injected directly into intraorbital, intra muscular, conal, or subconjunctival regions without causing diplopia.

Epithelial to Mesenchymal Cell Transformations and Botulinum Toxin Effect

Generally, most forms of macular degeneration involve a metaplasia of the retinal pigment epithelium. This process has been described as a conversion of the RPE cells to a fibrocystic cell capable of migrating into the neuro-retina or vitreous of the eye. The process importantly involves break away of the transformed RPE cell from its continuous sheet with reduced cell to cell adhesion allowing for membrane disruption (see FIG. 1B and FIGS. 5D-5F) and possible antigenic recognition of inflammatory cells in the choroid to initiated leakage and growth of new blood vessels. Further growth of new vessels from the choroid most often leak causing an accumulation of cytokines and toxic discharges into the neuro-retina.

Botulinum toxin formulations described herein essentially have the effect to retard or even reverse this process by causing expression and/or modulation of actin, maintaining cell differentiation and structure towards maintaining barrier function, halting the epithelial to mesenchymal transformation of the retinal pigment epithelium and effectively arresting both major forms of macular degeneration (wet and dry).

Because of the impaired conversion to mesenchymal forms from the retinal pigment epithelium by botulinum toxin formulations, it is possible to treat or provide prophylaxis against proliferative vitreoretinopathy following various forms of retinal detachments, a leading and often blinding complication of corrective retinal detachment surgery.

Vortex Blood Flow in the Human Choroid, Uveal Scleral Pump and Botulinum Toxin Effect (Flow-Related Pressure Effects on the Choroidal Pump)

Botulinum toxin has been known to affect blood flow in certain vascular beds causing a reduction in ischemia. This has been most commonly used to reduce Raynauds phenomena, particularly in the setting of scleroderma, a collagen vascular disease associated with fingertip ischemia, necrosis and auto-amputation. Such effects may be the direct result of botulinum on smaller to mid-size arteries or an effect on autonomic nerves regulating blood flow to finger circulation.

As described herein, blood flow can be enhanced in the human choroid by botulinum toxin injections remoted from the human eye or orbital contents, which do not cause neuromuscular weakness and effect an increased suction pressure on the base of the retina, removal of fluid from physical effect relation to Bernoulli's principle, removal of fluid from neural retina, and mitigation of the progression of various stages of macular degeneration (e.g., Drusen, drusenoids, pigment migration, and sub retinal and intra-retinal fluid).

Arterial perfusion to the choroid of the internal eye is mediated by branches of the ophthalmic artery entering via the posterior pole of the sclera with breakout to the long and short ciliary arteries which enter the eye providing a radially-oriented circulation path throughout the choroid of the eye. The choroid, on a flow per cubic mm basis, is the most vascularized tissue in the human body and accounts for about 95% of blood flow in the internal human eye. The flow leaves the anterior toward to cavernous layers entering a capillary net (choriocapillaris) just under the retinal pigment epithelium and finally enters the venous drainage system an exits eye through the vortex veins underlying the choroid.

A previously unappreciated aspect of this arrangement is the changes in directional movement within the choroid from radial flow entry to a flat circular drain with forward flow conversion into a circular vortex directed under the retinal pigment epithelium. This change is re-enforced by the net-like organization of the choriocapillaris. Circular flow with small lobules or larger groups of lobules creates a whirlpool effect, causing suction on the base of the retinal pigment epithelium. The organization of circular flow in addition to the whirlpools oriented in similar spine direction as related in the venous drainage into the vortex veins can be observed in fundus photography and fluorescein angiogram in a human albino choroid which can be studied because of absence of image blocking pigment in the RPE. This whirlpool effect has been named as the Charybdis effect after the whirlpool monster descried in the Odyssey (Homer). The whirlpool in the Odyssey sucked ships into the abbess destroying ancient ships. In the eye, the effect is possible providing a pumping mechanism to:

1. Remove waste products and metabolites from the eye;
2. Provide suction for proximity of rods and cones into the retinal pigment epithelium;
3. Provide movement of fluid through Bruch's membrane at the base of the retinal pigment epithelium;
4. Pressure effects regulating the genomic expressions favorable to barrier membrane integrity, cell adhesion integrity, and barrier effects (Pressure effects can drive uveoscleral flow is a positive direction for and fluid removal from the neuro retinal and sub retinal space);
5. Provide an enhance fluid removal mechanism to the neuro retina for cases of wet macular degeneration or leakage from other causes mentioned herein by enhancing choroidal blood flow;
6. Delay the development and progression of drusen, barrier integrity disruption of the RPE, and forces holding the RPE to Bruch's membrane;
7. Enhance and maintain the genomic of highly differentiated RPE and suppress EMT transformation and migration of the RPE into the neuroretina;
8. Provide a suction force clearing large molecules such as fats cholesterol clearing accumulation on Bruch's membrane, which contributes to cracks and leakage and ultimately to AMD progression;
9. Provide rapid clearance of inflammatory cytokines; and
10. Enhance phagocytosis of RPE with rod and cone projections.

Figure 18A:
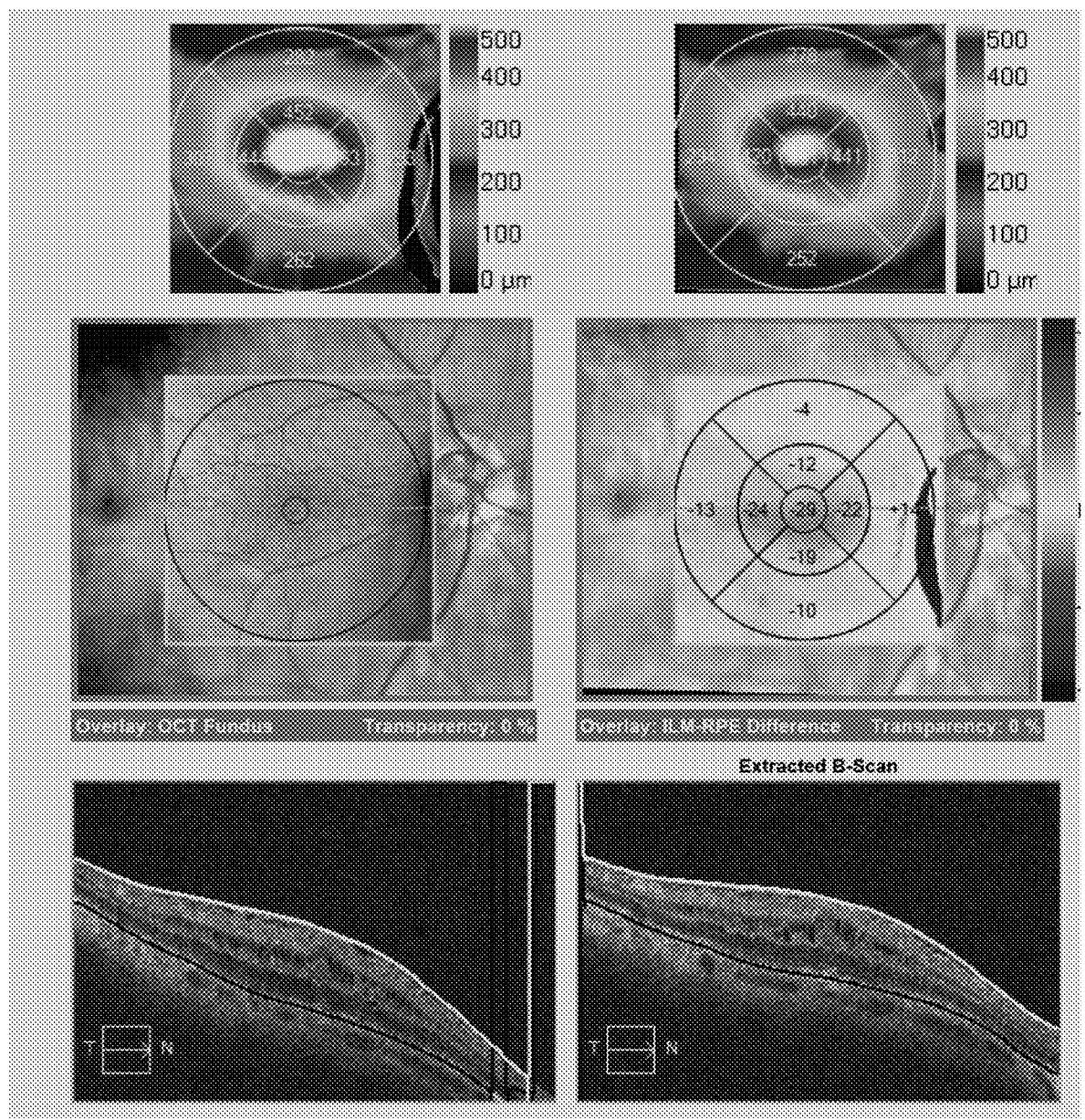
FIG. 18A illustrates images of a patient's eye after treatment administered in accordance with some embodiments of the subject disclosure.
Figure 18B:
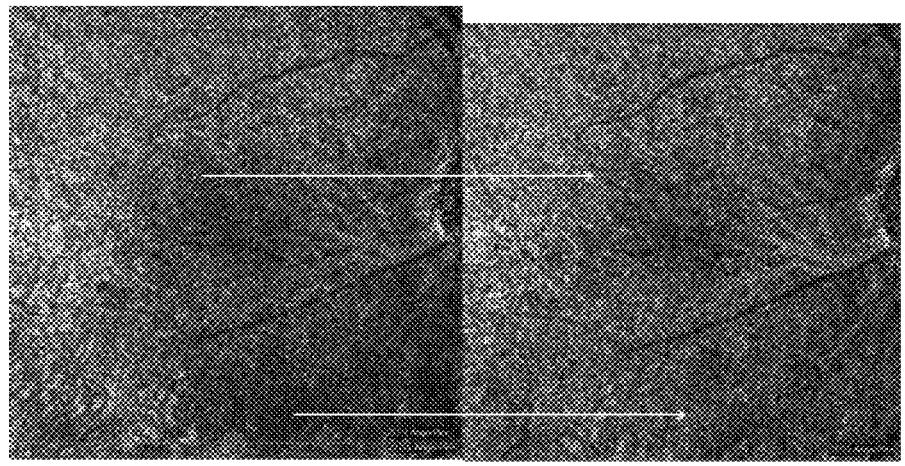
FIG. 18B illustrates an OCT-A image obtained from a patient treated according to the disclosed methods.
Figure 18C:
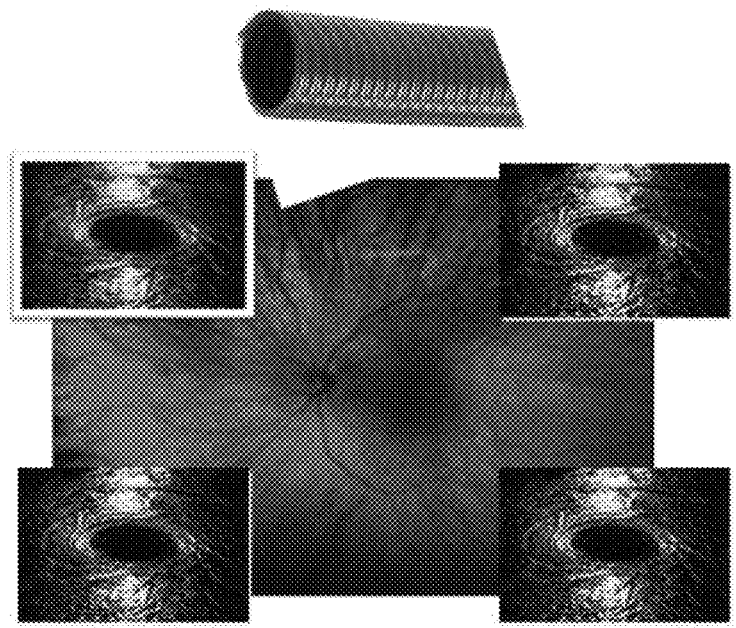
FIG. 18C illustrates an exemplary uveal sclera pump.

Increasing blood flow by effects of botulinum toxin or its fragments in injection formats described herein can cause preservation and enhancement in choroidal blood flow, including the choriocapillaris, increased choroidal pumping action, maintaining functions of the choriocapillaris, arresting or retarding progression of macular degeneration, and decreasing fluid accumulation in the macula (see FIG. 18C). The disclosed methods are thus capable of preserving the choriocapillaris and its function(s) with repeated injections of botulinum neurotoxin.

The above system can be targeted not only by botulinum toxin, but botulinum toxin used in conjunction with other accessory agents that enhance blood flow to the choroid. Accessory agents that can increase blood flow in certain circumstances include but are not limited to: phosphodiesterase type 5 (PDES) inhibitors (Viagra™, Cialis™, sildenafil, tadalafil, and vardenafil), nitrates (e.g., Isosorbide), statins (e.g., Atrovastin), niacin, marijuana, flavonoids, prostaglandins and prostacyclin analogues, agents producing NO (nitric oxide), and/or fish oil.

Targets for Therapy in the Clinical Setting

The disclosed formulations and methods may, in some cases, improve and/or maintain vision in patient afflicted with macular degeneration. Further, the botulinum toxin can be used to reduce anatomic changes in populations at risk for macular degeneration.

Functional measurements can involve various forms of visual acuity testing, contrast sensitivity testing, visual fields, anatomic outcome measurement using coherence retinal tomography or fluorescein angiograms, color vision, OCT, light dark adaptation measurements, or any other measurement of visual function.

The disclosed formulations may be used for one or more of the following:

1. Prophylactic in high risk populations as determined by genetic testing or strong family history
2. Arrest progression of dry degeneration to neo vascular stage with attendant leakage
3. In wet stage to both enhance drying and decrease choroidal leakage from recession of choroidal neovascularization.
4. Use of an enhancer of existing anti-VEGF agent to increase potency and duration of action allowing for fewer intra-ocular injection procedures.

An approach to treating dry macular degeneration involves maintaining the barrier between the neurosensory retina and choroid the source of neovascularization. As such an application involves making injections with barrier enhancing agents at the level of the retinal pigment epithelium, such injections would need to be extra-ocular to achieve a risk benefit ratio suitable repeated dosing in a patient with stage 1 or earlier stages of macular degeneration with leakage. Botulinum toxin via extra-ocular injections would be ideal as the safety factor are well known to be favorable for peri-orbital and facial injections at dosing levels described herein. Such repetition can provide a prophylactic for early macular degeneration cases progressing to stage 2 (wet variety) which is associated with a rapid deterioration in visual acuity and reading potential.

Botulinum Toxin Hemagglutinin in the Complex, Free from Muscle Weakening Neurotoxin, and Role in the Macular Application (VEGF Action)

For the first decades of botulinum use in humans, the toxin has been administered as a complex of neurotoxin associated with non-covalently bound proteins. The type A molecule is composed of neurotoxin, hemagglutinin proteins, and non-hemagglutinin, non-neurotoxin proteins. Most publications to date have indicated the latter two proteins have no role in clinical application of injectable botulinum toxins for various disease states and cosmetic applications.

The non-hemagglutinin may stabilize the formation to shelf life and the hemagglutinin has been shown to be important in to trans epithelial penetration and toxicity to orally ingested botulinum toxin and influence oral ingested toxicity. The hemagglutinin makes the complex more toxic by promoting gastric absorption. Collectively, these proteins may enhance in part or when used in combination the effects on the human retinae causing benefit to macular degeneration.

Contrary to the above, the macular and other epithelial applications to botulinum toxin are influenced by adjuvant proteins within the formulation. In fact, such proteins can be used enhancers, independent pharmaceutical agents to enhance botulinum potency on epithelial structures involving eye applications, and can have substantial directed biologic effects even when used in the absence of neurotoxin.

The examples given herein used BOTOX®, which is a complex with hemagglutinin adjuvant proteins. Botulinum toxin derived hemagglutinins have a direct action on cleaving cadherin E, a critical protein maintaining tight junction between gastric epithelial cells allowing for increase uptake of the botulinum neurotoxin increasing its toxicity. Further and even more remarkable relative to the retinal and eye applications, this effect (contrary to publications) can have an effect on various cadherin types causing a critical interaction with important receptors involved with endothelial cell growth (neovascularization.) Example 1 showed evidence of improvement in leakage and recession of a sub epithelial neo vascular membrane which is associated with improved prognosis for macular degeneration progression. Further, the effect of BOTOX® impedes differentiation of the RPE cells into mesenchymal fibrocytes which attendant death of neuro-retinal photoreceptors.

Cadherin cell connector proteins have been implicated in a number of retinal diseases including juvenile macular dystrophy, butterfly dystrophy, Ushers syndrome, autosomal recessive rod-cone dystrophy. A number of typed polymorphisms to cadherin genes have been linked to these macular and retinal conditions, which effect appearance and degeneration of the RPE. The unexpected result is that cadherin activity via botulinum complex or hemagglutinin known to act on cadherin lysis can in fact cause re-expression of cadherin cell connecting protein which enhance barrier activity.

Cadherin VE is known to be an important protein contained within vascular endothelium important to vascular integrity and growth of new blood vessels. Cadherin VE not only mediated adhesions between endothelial cells but is required for endothelial cell survival and maintenance. Vascular endothelial growth factor (VEGF) requires forms of cadherin to bind to its receptor tyrosine kinase to maintain and actuate endothelial growth. To this extent the hemagglutinin with the complex with or without the neurotoxin can act as an anti-VEGF agent capable of enhancing the effects of Avastin®, EYLEA®, or other forms of anti-VEGF drugs. The use of botulinum toxin with hemagglutinin can provide an action on VEGF function so as to inhibit activity and growth of vessels. This effect augments applications of retinal pigment epithelial barriers function, attachment to basement membrane, cell polarity, microvilli projections, desmosome integrity, and function of the retinal pigment epithelium also produced by the botulinum toxin based formulation.

The serendipity of these observations and applications is that quantities of hemagglutinin have been present in Botox-Occulinum® for years and safety factors of these quantities have been tested in numerous clinical studies, which have demonstrated a very high degree of safety. The complex has been demonstrated to disassociate quickly from the neurotoxin component once injected into a subject indicating free complexing protein are well tolerated not producing complications and substantial adverse events. Further isolates of the hemagglutinin protein via ion exchange or other forms of protein separations allow for the development of possibly more directed pharmaceuticals formulated being a specific anti-VEGF for the treatment of macular degeneration. Not to be limited by mechanism, the case reports presented herein proved the substrate to formulate theory and practice both from observation, unexpected pharmaco dynamics (eye penetration) and important medicinal effects consistent with the novel applications described herein.

Hemagglutinin derived from botulinum toxin can be recombinant produced and purified by removing the neurotoxin from the formation. For type A botulinum and its various subtypes, the final produced may be tested for weakening capacity using regional and mouse LD 50 assays to assure no residual neurotoxin is left in the formulation. The formulation may be administered in a pier ocular peri orbital or intravitreal form in dose quantities that have no effect on red cell agglutination but in a dosing format capable of suppressing neovascularization and retinal pigment epithelial cell leakage and vascular growth under the retinal pigment epithelium.

Botulinum Toxin Complexing Proteins

All naturally occurring serotypes of botulinum toxin (types A-G), have noncovalent associated, complexing proteins and thus forms toxin complexes. Complexing proteins are encoded in two gene clusters located close to each other on the C. botulinum chromosome. The first cluster encodes botulinum toxin itself plus a nontoxic, nonhemagglutinin (NTNHA) protein, while the second encodes three hemagglutinin (HA) proteins (HA1, HA2, and HA3), with HA3 being cleaved in serotype A post-translationally into two smaller components (HA3a and 3b). In botulinum toxin serotypes A-D and G, these components form two different toxin complexes (i.e., a medium toxin complex comprising botulinum toxin and NTNHA (300 kDa) and a large toxin complex that also includes the three HA molecules (500-600 kDa)). In contrast, serotypes E and F produce only the medium toxin complex. Serotype A also forms a third complex with a higher molecular weight (900 kDa). The detailed molecular structure of botulinum toxin type D large toxin complex has been visualized and comprises a 14-subunit complex of neurotoxin, NTNHA, three HA3 molecules (a 70 kDa molecule, also known as HA-70), three HA2 (also known as HA-17), and six HA1. (also known as HA-33) A denaturing capillary electrophoresis method can determine the subunits forming the very large/or higher molecular weight toxin complex of botulinum toxin type A, concluding that it contains single copies of the 150 kDa neurotoxin and NTNHA subunits, as well as 5-6 HA-17, 4-5 HA-23, 3-4 HA-48, and 8-9 HA-34 subunits, with a total mass of 880-1000 kDa.

Any component of botulinum toxin hemagglutinin would be candidate for assessment of Biologic Activity as an Anti-VEGF agent, cell to cell, cell to basement membrane or cytoskeletal stabilizing agent or an agent useful in application toward eye diseases described herein. The formulation may include neurotoxin with the complex proteins, any one or more of the complex proteins or component of the complexing proteins.

Enhancing the quantity of hemagglutinin in existing formulations is anticipated and can be useful for the treatment of spasticity conditions (post stroke and cerebral palsy), blepharospasm, hemifacial spasm, torticollis, prostate hypertrophy, plantar fasciitis, bruxism, arthritic conditions, myofascial pain, migraine headache, tension headache, major depression (MDD), anxiety, and wound healing. The inventor has observed inflammation as a sensitizer for worsening of many of the aforementioned conditions which can be addressed by higher quantities or enhanced quantities of botulinum toxin derived hemagglutinin to existing formulations to achieve a more potent effect.

Dose of HA and Dosing at Higher Concentrations than Previously Used Anticipated

As botulinum as Botox® has been used for decades quantities of HA derived from botulinum toxin type A complex (see Schantz Therapy with Botulinum Toxin) are anticipated to be at levels commonly used varying between the quantity associated between 5 U-8000 U (1 U=LD 50 for a white mouse). Most preferred is the quantity of hemagglutinin associated between 5-4000 U.

Topical Formulations of Isolated Botulinum Toxin Derived Hemagglutinin. Injectable Formulations Applications Higher dosing with botulinum toxin associated hemagglutinin (doses associated with excess of 800 U of botulinum complex) are possible as the lethal component of the complex (neuro-toxin) is not present so systemic weakness is not limited by doses. Inherently this concept allows for unique dosing forms free of paralyzing toxin.

Topical formulations of hemagglutinin derived from botulinum toxin is a viable composition at dose described herein for limiting new vessels formation and scaring on the human cornea from various infections (herpes virus, rosacea, ocular cicatricial pemphigoid, traumatic injury, exposure keratitis, corneal graft rejection, alkaline burns, socket inflammation, or other infections degenerations or dystrophies to the human cornea. Aerosols botulinum derived hemagglutinin are possible to prevent, vascular leakage and treat scaring in lungs, upper respiratory systems, esophagus, pharynx, intestinal tracts, nasal mucosa, rectal region. Infusions via intraperitoneal can be used to prevent scaring in the peritoneum and surface of the large and small intestine. Intravenous infusion can be used to mitigating new vessel growth into malignant tumors, which promote neovascularization such as metastatic tumor to the liver, spleen, lungs, brain, and other organs. Use in allergy is anticipated as well as autoimmune disease, such as Graves disease and auto-immune thyroid disease. Use in various forms of uveitis, to prevent exudation and leakage is anticipated by per-ocular, intravitreal, or intravenous injection. Treatment of leaking blood vessel associated with diabetic retinopathy and blinding diabetic neovascularization can be targeted by the "anti-VEGF" component action of botulinum toxin hemagglutinin activity. Chronic asthma with vascular leakage and scarring can also be targeted, in some embodiments. Eczema and inflammatory skin diseases can be targeted. Various forms of sinusitis can be targeted for treatment. Use in IGE mediated edema can also be targeted. Other inflammatory conditions can be anticipated for an anti-VEGF action.

The novel use of isolated hemagglutinin for macular degeneration circumvents issues related to induced paralysis from the neurotoxin component of the molecule allowing larger dosing of the hemagglutinin than possible when the hemagglutinin is used with a complex with muscle paralyzing neurotoxin.

Extension of Invention to Other Forms of Disease Involving the Retinal Pigment Epithelium Other forms of disease of the retina can be targets for botulinum toxin given by extra orbital and/or per-orbital method, including:
1. Retinitis pigmentosa (RP), recessive, x linked and dominant forms
2. Best disease
3. Stargardts disease
4. Pattern retinal and macular dystrophy
5. Chloroquine retinopathy
6. Lattice dystrophy (with and without retinal breaks)
7. Angioid streaks
8. Birdshot retinopathy
9. Central serous retinopathy
10. Ocular histoplasmosis syndrome
11. Irvine Gass syndrome
12. White dot syndromes
13. Trauma to retinal pigment epithelium
14. Ocular Toxoplasmosis syndrome
15. Ocular conditions associated with pseudo exfoliation syndrome
16. PVR (post-operative proliferative vitreoretinopathy)
17. RPE damage associated with choroiditis
18. Macular hole (partial and complete)
19. Early and late stages of Retinal Detachment (both rhegmatogenous-break related and non-rhegmatogenous, non-break related).
20. Diabetic macular edema
21. Diabetic retinopathy (any stage) (both retino-vascular barrier effect enhancement by botulinum toxin, and RPE enhancements in barrier and fluid leak functions)

In each of the above diseases disruptions of the retinal pigment epithelium can occur causing damage to photoreceptors by leakage of choroidal fluid containing cytokines, leukocytes, antibodies and various immune reacting agents destructive to photoreceptors leading to visual loss and blindness.

Agents that augment the epithelial barrier elicit an increased integrity of the pigment epithelial barrier enhancing the protection of the photoreceptors and visual function, even in conditions not associated with age related macular degeneration. Further botulinum toxin can have an effect on neuropeptide and other agents of neurogenic inflammation which when transported to choroid acts to suppress barrier damage and subsequent visual loss associated with macular degeneration as well as other forms of degenerative and inflammatory diseases. Further, even if effects do not address genetic causes or other processes, the enhancement of the RPE photoreceptor system can be neuroprotective for photoreceptors by mechanisms of enhancement of RPE function supporting the phagocytosis, transport of apical rod cone structures.

In the case of retinal degeneration such as retinitis pigmentosa, the defect may involve primarily the photoreceptors with retinal pigment epithelial changes being secondary to excessive degenerative rod and cones material undergoing phagocytosis with toxic accumulation in retinal pigment epithelial cells followed by RPE degeneration and dysfunction. An agent which may augment the RPE tolerance for toxic protein accumulation will retard visual deterioration based on RPE loss. Other mechanism at the level of the photoreceptors can play a role. Stabilization of barrier membranes with endothelial cells may further be operational in preventing or migrating against progression of photoreceptor damage and protection. The cause of macular edema in RP is possibly related to inflammatory autacoids and antibodies entering the neuroretina and elicited a breach in the blood retinal barrier at the retinal circulation. The edema suggests that RPE leakage from vascularized choroid may be important in the progression of RP. Further intrinsic functions of the RPE such as preservation of microvilli, increased efficiency of phagocytosis based on actin stimulation in submembrane regions, increased metabolic turnover of accumulated dysfunctional rhodopsin protein in the photoreceptors can play a role in reducing the visual loss over time in the various forms of retinitis pigmentosa.

Genetic defects have been associated with retinitis pigmentosa, a hereditary condition associated with night blindness and degeneration of rods and cones in the neuroretina leading to progressive and often relentless loss of vision.

Proliferative Vitreal Retinopathy (PVR) and Epithelial Mesenchymal Transformation (EMT)

PVR is one of the most devastating complications occurring after retinal detachment surgery. The reaction of the RPE here is to undergo EMT with proliferation of cell into the vitreous with conversion to fibrocytes leading to traction membranes causing recurrent retinal detachments which are poorly treated with existing measures. The application of botulinum toxin by extra ocular or intra-ocular administration stabilizes the retinal pigment epithelial from fibrous and migratory conversions leading mitigation of the fibrotic conversion surrounding retinal detachment surgery. Application as a prophylactic before, during and after the surgery proves useful measure to decrease incidence and progression of this complication.

Pseudo-Exfoliation Syndrome is still another condition associated with abnormality in cell to cell adhesion. Here migration of pigment epithelial cell from uvea can often causes glaucoma by cell accumulation in the trabecular meshwork. Use of botulinum toxin by intra ocular or extraocular injections can result in tightening of the adhesions between pigment cells leading to less pigment dispersion, allowing a novel method to treat this disease. Further, this condition can be associated with higher cataract surgery complication rate from lens and zonule dislocation. This agent can be used for stimulating a tighter connection between pigment epithelium and zonules.

In some embodiments, formulations comprising botulinum toxin may be injected or topically applied to a patient for the treatment of surface epithelial ulcers and stabilization of biologic tissue barriers. Botulinum toxin has conventionally been used to treat spasmodic muscle contractions, relax muscles causing effects on muscles tone, blocking autonomic function causing secretions, causing diminished sensation of pain such as headaches of various causes, and smoothing muscle generated skin wrinkle. Application to non-muscular portions and regions of skin can cause epithelial tightening by the mechanisms described herein.

Another novel application of botulinum toxin which when used topically or by injection causes a rapid healing of an epithelial ulcers or stabilize biologic tissue barriers disrupted by various disease processes other than macular degeneration. The effect centers around a novel biologic observation that actin and related cyto-structure subcellular elements are stimulated by botulinum toxin causing upregulation of cyto architectural protein after injections, causing preservation of cellular structures through enhancement of the cytoskeleton, preservation of cell internal structures, and enhancements of adhesions between cells, enhancement of actin production and microtubules cross connections between cells which support and enhance biologic barriers.

Targeted ulcers occur in the colon, skin along extremities and lower legs, decubitus ulcers, pressure ulcers, corneal ulcers, mouth and tongue ulcerations, esophageal ulcers, stomach ulcers, poorly healing surgical and cutaneous wounds, burn induced wounds, ulcers induced by vasculitis, infections by bacteria and fungus, around surgically induced ostea, per rectal ulceration, radiation induced ulcerations, mouth and gingival ulcers, gingival retraction, conjunctival ulcers, and post infectious ulcers. Injectable and topical methods of delivery are operational for these injections.

Critical epithelial/endothelial barriers include not only the retinal pigment epithelial barriers, but corneal epithelial integrity, urologic epithelial barriers in urethra and bladder, blood brain barriers, endothelial barriers in blood vessels and corneal endothelium, repair of endothelial microvilli with the GI tract and enhancement of dental gingival barriers important in generation of tooth decay and periodontal disease. The biologic barriers are enhanced by augmentation of the actin and related protein cyto skeleton causing enhancement of barrier integrity necessary for the health maintenance of the target organ and related tissues.

Botulinum toxin has been conventionally used to treat spastic muscles, temporally denervate glands (eccrine and sebaceous glands, salivary glands, prostate gland, lacrimal gland, mucous secretions from nasal mucosa, acid secretion in stomach. Muscular targets have been to induce myoneural blockage causing neurogenic muscular atrophy by blocking acetyl choline release by blockage of vascular release of acetyl choline. The targets involve binding of the heavy chain to the presynaptic membrane via the c-terminus of the botulinum toxin heavy chain to the membrane receptor with penetration of the light chain into the cytoplasm causing cleavage of SNAP-25, a mechano-fusion protein essential in exocytosis. The blockage of myoneural junctions occurs on a dose-dependent area surrounding injections in a fashion that the effects are targeted to involved area and that undesirable diffusion causing complications does not occur. Beyond these applications, botulinum toxin is used herein to produce increased integrity of an epithelial surface to enhance to cell to cell integrity of the surface, enhance the barrier function of the surface and function to sustain the surface from degenerative changes occurring in senescence or in disease processes.

The cellular effect which enhances the applications of botulinum toxin to novel indications which are difficult and often impossible to effectively and definitively treat. The invention stems from a formerly described "epi phenomena" associated with neuro-muscular injection blockade. Injections of botulinum toxin causes blockage of exocytosis of acetyl choline from pre synaptic vesicles, flaccid muscular paralysis, with subsequent atrophy of the muscle cells. The epi phenomena involves sprouting of the nerve around the myoneural block with growth of the sprouts away from the neuromuscular junction. Prior observers have interpreted this cellular response was secondary just to the myoneural block, however this explanation ignores the observation that this effect is a direct effect of botulinum toxin to enhance actin and related cyto architectural protein stimulated directly by the toxin and associated proteins causing increased protein synthesis and expression of the actin and related cyto architecture which causes the sprouting. This observation is operational to the inventions and clinical applications described herein and define a subcellular process by which the toxin produced benefit to targeted tissues.

Actin and related adhesion and associated protein cyto architecture is critical for many cell and cellular tissue functions, longevity, and barrier integrity. Programed cell death can occur by spontaneous cellular destruction of the cyto skeleton protein and such proteins are critical to cellular polarity, specialization, and cell adhesion. Upregulation of actin and related proteins in disrupted cell and tissue cause by inflammation, degeneration, infections, metabolic derangements, trauma, or burns helps cells and tissues to resist death and destruction. This essential effect of botulinum toxins is critical to the practice of use of botulinum toxin to assist in the healing process, enhancing wound healing, enhancing epithelial healing and the velocity of healing. Cyto skeleton enhancing drugs can be enormously helpful to be used to preserve cells from destruction based on various causes.

Botulinum Toxin Types (Topical Application and Injection) to Achieve Cytoskeletal Changes similar to C2, C3)

Botulinum toxin exists as types A(1-5), B, C, C2, C3, D, E, F, G. The toxin type C2,3 cause a cytotoxic effect causing cell death by influencing the lysis of actin, increased tissue and cell permeability and integrity causing a cytotoxic effect. The other neurotoxins cause organism death by flaccid paralysis, asphyxiation from respiratory paralysis. The essential component to this invention involves using various forms of non type C2, C3 toxin to achieve intra cellular and intercellular enhancing effect on actin and related protein production as a cyto-protective effect of the botulinum use by application at lower doses (e.g., various forms of type A toxin). In effect, various forms and doses (concentrations) of botulinum toxin can have opposite effects on the cyto skeleton proteins depending on tissue type and cell cycles. This observation and derivative application is essential to understanding the practice of the invention. Type A botulinum toxin by enhancement and preservation of the cyto skeleton can be protective and not toxic at given dosing and application methods described herein. This concept is counter intuitive to the know effects of certain isoforms of botulinum toxin such as type A.

Epithelial Surfaces

Epithelial surfaces tend to have cellular and tissue integrity requirements important to the health and resilience to various forms of diseases and injuries.

The skin and mucous membranes are the apparent epithelial surfaces in the human body. The skin functions to maintain moisture content in the body and protect against life threatening dehydration with humidity, temperature, convection changes. The skin involves tightly compacted squamous epithelial cells important to the function of the biologic barriers. These cells arise from germinal cells attached tightly to a basement membrane and to each other on a plane that is normal to the epithelial surfaces. Actin and related microtubule structure are strongly expressed in the cytoplasm of these cells and respond to various insults such as burns, viral diseases, trauma, autoimmune diseases, degenerative conditions, and hereditary defects. The subcellular elements important to the contribution of the skin as a functioning barrier include actin and microtubule organization of the skin cell allowing for a high number of adhesions including transcellular tubular organization, desmosomes and hemi-desmosomes, and cell membrane integrity. Diseases and genetic experimental models involving actin and related protein derangements causes a disruption of the barrier leading to structural changes, dehydration, protein loss and damage and structural skin disfigurement.

Herein, an approach is described which alters the actin and related microtubule elements of the skin cells so that:
1. The integrity of the skin barrier is maintained by topical or injectable botulinum toxin so that evaporation, protein leak, release of proteases enzymes, immuoglobulins, and leukocytes potentially harmful to the epithelial barrier.
2. Enhance epithelial cell integrity and proliferation so that ulceration and other forms of skin discontinuity can heal more effectively.
3. Function as a preventative therapy to keep wound ulcers from forming such as cutaneous pressure ulcers, ocular exposure ulcers from facial paralysis or exophthalmos, esophageal ulcers with the esophageal mucosa due to reflux, bladder ulceration from irritates such as radiation or chemo therapy, peptic ulceration in in patient with active or past duodenal ulcers, genival retraction from breakdown of gingival epithelium from bacteria or genetic predisposition.

Mucous membrane surfaces are also subject to ulcerations, and dysfunctions related to loss of barrier integrity. Such loss of integrity can lead to leakage of enzymes, immunoglobulins and related cellular elements such as polymorphonuclear leukocytes capable of further damage to barrier functions and other cellular functions of the mucous membrane surfaces. Botulinum toxin when applied by injection or topically can function to enhance the integrity of the mucous membrane epithelial barrier by causing a microtubule alteration in the mucous membrane cellular structure allowing for increased barrier function of the epithelial cells.

Herein, an approach is described which alters the actin and related microtubule elements of the mucous membranes and intercellular binding proteins (cadherins) cells so that:

(1) the integrity of the skin barrier is maintained by topical or injectable botulinum toxin so that evaporation, protein leak, release of proteases enzymes, immuoglobulins, and leukocytes potentially harmful to the epithelial barrier and/or (2) epithelial cell integrity and proliferation are enhanced so that ulceration and other forms of skin discontinuity can heal more effectively.

Examples of mucous membrane surfaces applicable include but are not limited to: Conjunctival, Vaginal, Rectal, Alveolar, Glomerular and renal tubules, Intestinal, Gastric, Esophageoal, Nasal Mucosa, Oral mucosa, Dental-Gingival mucosa (periodontal disease), Bronchiolar and tracheal mucosa, Bladder mucosa, Urethral mucosa, Ureter Mucosa, and/or Gall Bladder and biliary duct mucosa.

Conventionally, botulinum toxin is used to removed dynamic lines and wrinkles based on a neuromuscular weakening effect. This approach has been employed for decades and is the source of billion-dollar revenue market. This approach also has been the target for United States FDA approval pathways for these indications using forced frown lines as an endpoint. Muscle injections are described as the target for injection to produce the favorable aesthetic results.

The disclosed formulations and therapeutic methods may, in some cases, tighten the cell to cell adhesions in epithelial surfaces provide more insight and utility to aesthetic application. Application of botulinum toxin by injection to non-muscular regions at multiple puncture sites on surfaces away from muscle tissue can prove beneficial to skin texture and be effective in removing non-dynamic wrinkles (wrinkles not generated by resting muscle tone or contractions of muscles). The disclosed formulations may be delivered along multiple punctures sites far lower than necessary to produce a muscle weakening effect.

Botulinum Toxin Action on the Rho Protein Family

Certain immune-types of botulinum toxin are known to act as cytotoxins causing cell damage and poisoning by non-neuromuscular mechanisms. These are the botulinum C2, C3 types which are distinctive both in chemistry and cellular effect. These toxins are known to enhance actin dissolution by actin and disruption of tight junctions with vascular leakage, hemodynamic instability and death. This toxin act as ADP ribosylating toxin which interfere with actin formation and integrity. Recently, botulinum toxin type A has been shown to interfere which fibroblast migration and function and reduce cutaneous scars. The observations indicate by observers that other botulinum toxins have an effect on actin cytoskeleton elements in a way that impairs actin formation and cellular functions associated with actin such as cell motility, and tissue functional integrity. These biologic effects are negative when toxin is given at high doses to cause impairment of cellular function.

Cell motility requires actin cell polymerization and dissolution occurring rapidly to accomplish this function from member of the Rho protein family (Cdc2, Rac, Rho). These proteins are also involved in the maintenance of cell polarity, motility, important to many tissue barrier functions.

Contrary to the above, the invention described herein involves a positive effect on barrier cells to enhance and strengthen cell to cell contact and cell to basement membrane contacts for non-motile epithelial cells constituting a biologic barrier as well as enhancing (not depressing) cell migration when a defect is present or enhancing biologic barriers important to disease processes when there is a defect in epithelial adhesion and transformation. Improvement in barrier dysfunction results from the cyto architectural effect from the toxin. The type A botulinum toxin has been associated with reorganization of actin fibers in neural derived cell cultures indicating a contrary effect to related type C2, C3 and type D toxin. Rather than disrupt cell to cell contacts, type A toxin is able to cause actin and related proteins to reorganize the cytoskeleton in a configuration that tightens cell to cell contact, increase integrity of biologic barriers, enhance function of epithelial barriers and promote epithelial and endothelial growth ton seal defects in endothelial and epithelial cell barriers. The mechanism can relate to interacting to similar enzymes in the Rho family adjusting relative rates of actin and related protein reorganization to that the tight junctions are enhanced and biologic interactions of actin with its attachment protein cadherin and specialized cell intermediate filaments enhance cell function and barrier functions.

The above appears contrary to published reports but just as the neuromuscular effects are controlled by dose. These cytological effects are also subject to doses conventionally used to treat medical conditions described herein. Such doses can modulate the actin skeleton in a way to enhance the barriers and cellular adhesive quality increasing the function within the epithelial barrier to mitigate a disease process based on a subliminal effect on the cytoskeleton with enhancements of adhesion from actin, cadherin interactions.

Complex Vs Pure Neurotoxin

Current efforts in pharmaceutical design have sought to remove the accessory protein from botulinum toxin preparations. These proteins include hemagglutinin and non-hemagglutinin non-neurotoxin proteins. Recently, botulinum-associated protein hemagglutinin has been associated with interaction and weakening of cadherin proteins in tissue types. Cadherin interactions can be important in maintaining the integrity of the neural synapse. This disruption is tight to further disrupt the actin cell element of the presynaptic neuron and provide for an enhance of botulinum toxin uptake at the presynaptic structure causing a more effective penetration of botulinum toxin uptake enhancing the potency and effectiveness of the injectable or topically applied botulinum formulation. The interaction with cadherin protein can trigger genomic response causing enhanced cadherin and associated proteins for cell and tissue repair.

The effectiveness of some formulations of botulinum toxin have been observed by clinicians not to be equivalent to botulinum complex (BOTOX® vs XEOMEN). Any membrane interactive substance which can increase permeability of botulinum toxin into the neuron may be useful to enhance potency. Recently, two studies on rhytids and adult onset spasmodic torticollis) which reported increased potency based on an adjuvant poly-lysine (poly-cation) which was designed to increase penetration to the motor neuron axon tip. Alternate methods are described herein of increasing the concentration of the hemagglutinin to enhance effect of the formulation on muscle to axon nerve tip intercellular attachment protein in such a way to increase permeation of the neuron to the axon tip and enhance potency.

Prophylactic Therapy in Stage 1 Macular Degeneration

The therapies disclosed herein, in some embodiments, include benign placement alternatives to intra-vitreal injections which represents the current placement method in using anti-VEGF pharmaceuticals such as Eylea®, Lucentis®, and Avastin®. In some embodiments, the disclosed methods provide an opportunity for a novel treatment approach of providing a prophylactic therapy for high risk patients, patients diagnosed with stage 1 AMD, and/or patients with high risk features to progress to geographic atrophy or stage 2 (exudative) AMD.

In current practice, macular degeneration is often diagnosed as stage 1 before the disease progresses to the rapid vision-destroying stage 2 degeneration involving intra-retinal and sub-retinal leakage from new vessels growth and new vessel growth under or over the retinal pigment epithelium. In some embodiments, a method of preventing any stage of macular degeneration is provided that involves: identifying a patient with high risk for AMD based on genomic testing for high risk polymorphisms genes structures noted to be associated with macular degeneration. In these and other embodiments, the method continues with providing an extra-ocular injection in the orbit, Para orbital, peri orbital region (sinuses or temporal), and/or pterygopalatine fossa lateral orbital region, in a manner that allow botulinum effect on the posterior eye, macular or intra-ocular structures. The method may continue with monitoring the patient and eventually decreasing the incidence of macular degeneration on the targeted eye or eyes using the methods as described herein for macular degeneration assessment.

There are risk factors for the development and progression of AMD that may be used in connection with the disclosed methods. For example, possible risk factors that may be considered include but are not limited to: number and volume of drusen and drusenoid lesions, extent and position of geographic atrophy in target or contralateral eye, number and position of hyper-reflective foci into the neuroretina (either position over drusen-drusenoids), loss and disorganization of continuity of IS-OS line or outer nuclear layer, hyper or hypo pigmentation, hyper-reflectivity and deposits within the drusens, dynamic changes in number and size of drusens, soft drusen, hyperreflective foci, IS-OS lines ONL, and presence and number of pseudo-drusen. Additionally, genetic testing may be employed in connection with the disclosed methods to assess polymorphisms associated with severe macular degeneration as well as complement factors and other genes associated with severe disease.

Macular Edema

There are many known causes of macular edema. For example, macular edema is frequently associated with diabetes, where damaged blood vessels in the retina begin to leak fluids, including small amounts of blood, into the retina. This is the most common cause of visual loss associated with diabetes. Sometimes deposits of fats may also leak inside the retina. This leakage causes the macula to swell. In this situation, the biologic barrier is defined by the retino-vascular endothelium and supporting pericytes in the retinal circulation.

Eye surgery, including cataract surgery, can increase your risk of developing macular edema due to blood vessels becoming irritated and leaking fluids. Macular edema that develops after cataract surgery is called cystoid macular edema (CME). Some of the other macular edema causes include: type 1 and type 2 diabetes, age-related macular degeneration (AMD), uveitis, retinal vein occlusion (branch and central retinal vein occlusion—Example 8), blockage in the small veins of the retina, due to radiation, macular telangiectasias, side effects of certain medications, and certain genetic disorders, such as retinoschisis or retinitis pigmentosa, incontinea pigmenti. The disclosed formulations are methods may be used to treat, prevent, or cure macular edema caused by one or more of these conditions.

By mechanisms described herein, the barrier occurring around the retinal vessels (endothelium and peri-cytes) can be augmented causing less leak, less macular edema, and/or preservation of vision. For these indications, injections can be given via pars plana (intra-ocular injections) or through soft tissue injections surrounding the eye in a similar manner described for macular degeneration. Topical applications with higher doses used to achieve greater penetration can also be used. Such higher doses are within the ranges from 1-5,000 units.

Renal Function (Barrier Function) and Nephrotic Syndrome

Nephrotic-range proteinuria is the loss of 3 grams or more per day of protein into the urine or on a single spot urine or on a single spot urine collection, the presence of 2 g of protein per gram of urine creatinine. Nephrotic syndrome is the combination of nephrotic-range proteinuria with a low serum albumin level and edema. Nephrotic syndrome has many causes, including primary kidney diseases such as minimal-change nephropathy, focal glomerulosclerosis, and membranous nephropathy. Nephrotic syndrome can also result from systemic diseases that affect other organs in addition to the kidneys, such as diabetes, amyloidosis, and lupus erythematosus. Nephrotic syndrome may affect adults and children of both sexes and of any race. It may occur in typical form, or in association with nephritic syndrome. The latter connotes glomerular inflammation, with hematuria and impaired kidney function.

Nephrotic syndrome can be primary, being a disease specific to the kidneys, or it can be secondary, being a renal manifestation of a systemic general illness. In many cases, injury to glomeruli is an essential feature. Kidney diseases that affect tubules and interstitium, such as interstitial nephritis, will not cause nephrotic syndrome.

Primary causes of nephrotic syndrome include the following, in approximate order of frequency: Minimal-change nephropathy, Focal glomerulosclerosis, Membranous nephropathy, and Hereditary nephropathies. Secondary causes include the following, in order of approximate frequency: Diabetes mellitus, Lupus erythematosus, Viral infections (e.g., hepatitis B, hepatitis C, human immunodeficiency virus [HIV]), Amyloidosis and paraproteinemias, Preeclampsia, and Allo-antibodies from enzyme replacement therapy.

Nephrotic-range proteinuria may occur in other kidney diseases, such as IgA nephropathy. In that common glomerular disease, one third of patients may have nephrotic-range proteinuria. Nephrotic syndrome may occur in persons with sickle cell disease and evolve to renal failure. Membranous nephropathy may complicate bone marrow transplantation, in association with graft versus host disease. From a therapeutic perspective, nephrotic syndrome may be classified as steroid sensitive, steroid resistant, steroid dependent, or frequently relapsing.

In a healthy individual, less than 0.1% of plasma albumin may traverse the glomerular filtration barrier. Controversy exists regarding the sieving of albumin across the glomerular permeability barrier. On the basis of studies in experimental animals, it has been proposed that ongoing albumin passage into the urine occurs in many grams per day, with equivalent substantial tubular uptake of albumin, the result being that the urine contains 80 mg or less of albumin per day.

However, studies of humans with tubular transport defects suggest that the glomerular urinary space albumin concentration is approximately 3.5 mg/L. At this concentration, and a normal daily glomerular filtration rate (GFR) of 150 liters, one would expect at most 525 mg per day of albumin in the final urine. In health, urine albumin is less than 50 mg/day, because most of the filtered albumin is re-absorbed by the tubules. Amounts above 500 mg/day typically point to glomerular disease.

The glomerular capillaries are lined by a fenestrated endothelium that sits on the glomerular basement membrane, which in turn is covered by glomerular epithelium, or podocytes, which envelops the capillaries with cellular extensions called foot processes. In between the foot processes are the filtration slits. These three structures—the fenestrated endothelium, glomerular basement membrane, and glomerular epithelium—are the glomerular filtration barrier. A schematic drawing of the glomerular barrier is provided in FIG. 8.

Figure 8:
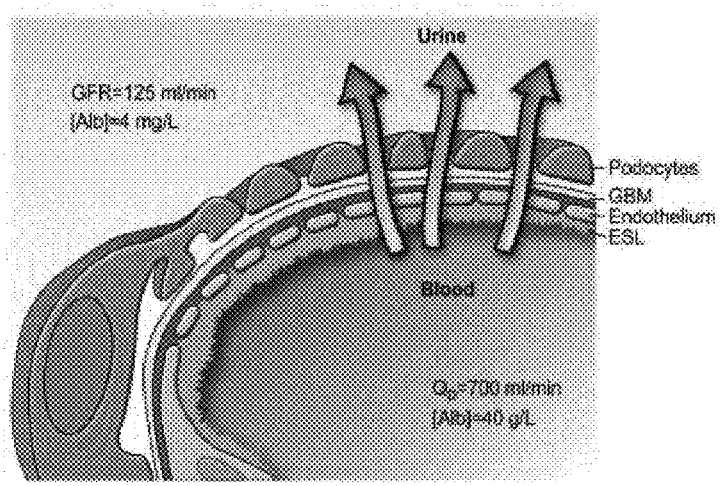
FIG. 8 shows a schematic drawing of the glomerular barrier.
Figure 9A:
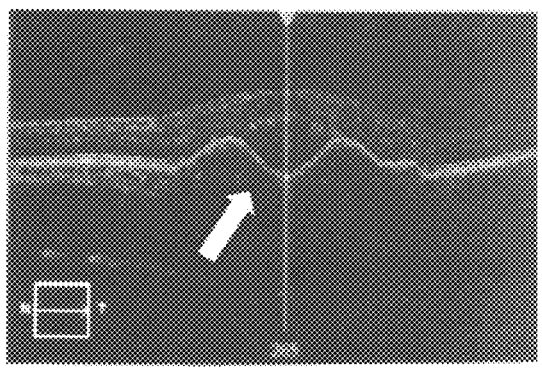
FIGS. 9A-9F illustrate OCT images obtained from patients treated with the disclosed therapeutic formulations, according to the disclosed methods. Enhancement effects of anti-VEGF agents are also visible in FIGS. 9A-9F.
Figure 9B:
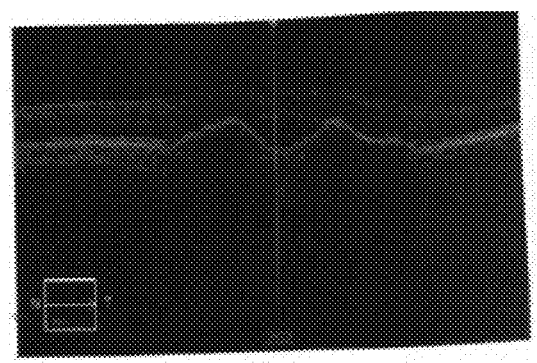
Figure 9C:
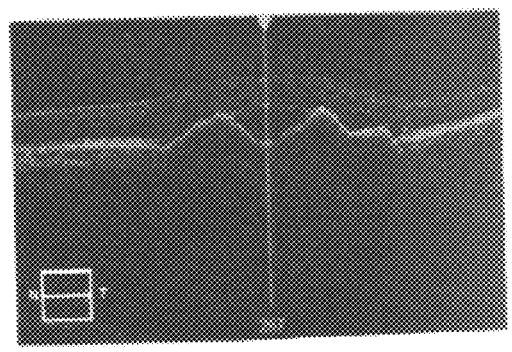
Figure 9D:
Figure 9E:
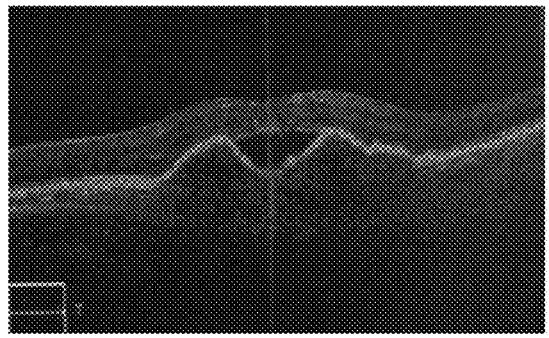
Figure 9F:
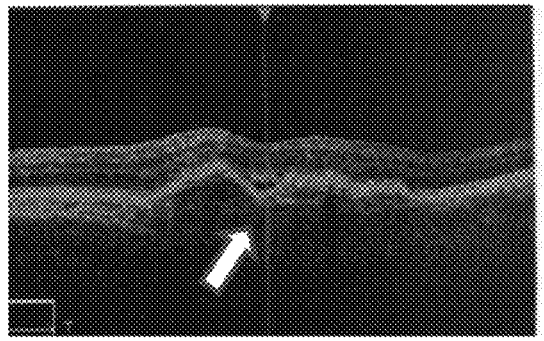
Figure 10A:
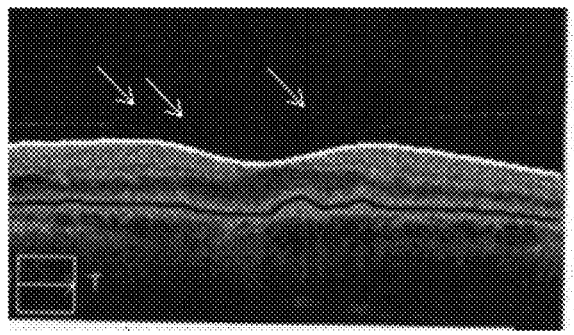
FIGS. 10A-10B illustrate OCT images obtained from a patient treated with the disclosed therapeutic formulations, according to the disclosed methods.
Figure 10B:
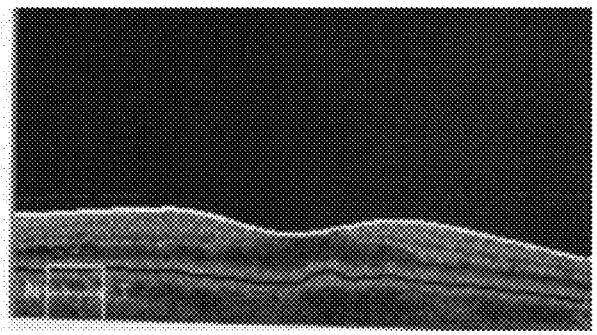
Figure 11A:
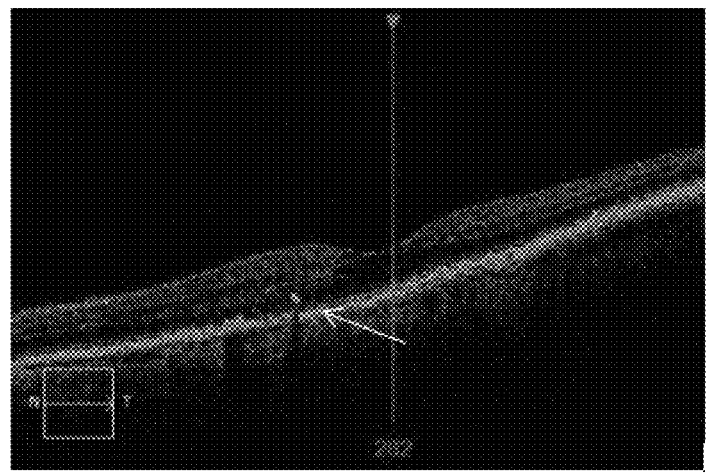
FIGS. 11A-11D illustrate OCT images obtained from a patient treated with the disclosed therapeutic formulations, according to the disclosed methods.
Figure 11B:
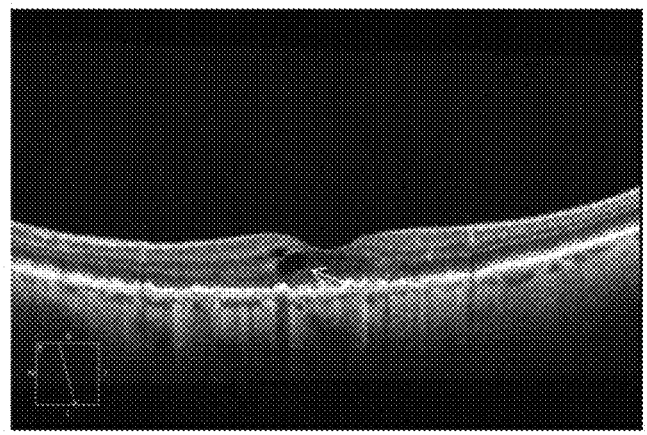
Figure 11C:
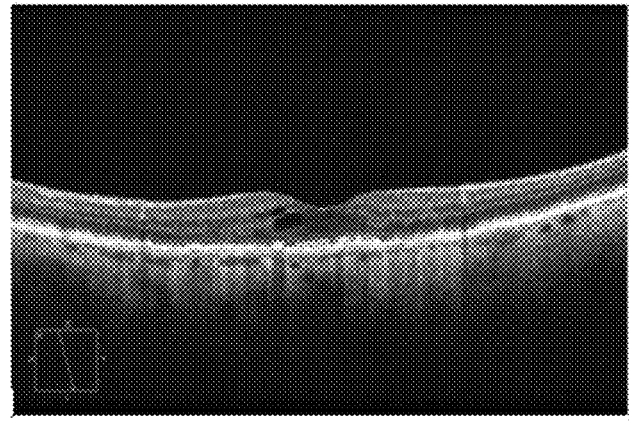
Figure 11D:
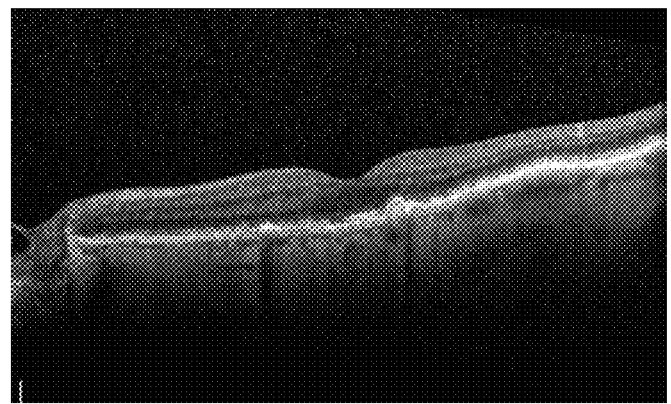

FIG. 8 shows a schematic drawing of the glomerular barrier. In FIG. 8, the abbreviation "GBM" refers to the glomerular basement membrane and "ESL" refers to the endothelial cell surface layer (often referred to as the glycocalyx). Primary urine is formed through the filtration of plasma fluid across the glomerular barrier (arrows); in humans, the glomerular filtration rate (GFR) is 125 mL/min. The plasma flow rate (Qp) is close to 700 mL/min, with the filtration fraction being 20%. The concentration of albumin in serum is generally 40 g/L, while the estimated concentration of albumin in primary urine is 4 mg/L, or 0.1% of its concentration in plasma.

Filtration of plasma water and solutes is extracellular and occurs through the endothelial fenestrae and filtration slits. The importance of the podocytes and the filtration slits is shown by genetic diseases. In congenital nephrotic syndrome of the Finnish type, the gene for nephrin, a protein of the filtration slit, is mutated, leading to nephrotic syndrome in infancy. Similarly, podocin, a protein of the podocytes, may be abnormal in a number of children with steroid-resistant focal glomerulosclerosis.

The glomerular structural changes that may cause proteinuria are damage to the endothelial surface, the glomerular basement membrane, or the podocytes. One or more of these mechanisms may be seen in any one type of nephrotic syndrome. Albuminuria alone may occur or, with greater injury, leakage of all plasma proteins (ie, proteinuria) may take place. Proteinuria that is more than 85% albumin is selective proteinuria. Albumin has a net negative charge, and it is proposed that loss of glomerular membrane negative charges could be important in causing albuminuria. Nonselective proteinuria, being a glomerular leakage of all plasma proteins, would not involve changes in glomerular net charge but rather a generalized defect in permeability. This construct does not permit clear-cut separation of causes of proteinuria, except in minimal-change nephropathy, in which proteinuria is selective.

The renal tubules are also governed by barrier function in the cell to cell adhesion and attachments to basement membranes. Targeting the kidney or nerves entering the kidney can be useful to treat renal diseases in which barrier function are essential.

As botulinum toxin is capable of stimulating proteins which are essential to cells to cell adhesion and attachments to basement membranes, the enhancement of the adhesion complexes at the glomerular barrier and tubules can be useful to treat kidney disease. The kidney lies in the retroperitoneum close to the mid to lower back making this organ assessable to injections through back muscles, and organ via innervation with axoplasmic transport. Needle can access the kidney from back injections and diffusion through dosing nomograms. In some cases, the treatment objective may be to slow progression on diabetic need for dialysis or to treat or prophylactically treat glomerular disease with high risk patients (for example, advanced stage diabetics, system lupus patients, para-proteinemias, patients with systemic amyloidosis, or primary nephrotic syndromes).

Periodontal Disease Tooth Loss

Teeth are attached to the surrounding and supporting alveolar bone by periodontal ligament (PDL) fibers. PDL fibers run from the bone into the cementum that naturally exists on the entire root surface of teeth. They are also attached to the gingival (gum) tissue that covers the alveolar bone by an attachment apparatus. Because this attachment exists superficial to the crest, or height, of the alveolar bone, it is termed the supracrestal attachment apparatus. This apparatus is subject to deterioration in Periodontal disease.

The supracrestal attachment apparatus is composed of two layers: the coronal junctional epithelium and the more apical gingival connective tissue fibers. The two layers together form the thickness of the gingival tissue and this dimension is termed the biologic width. Plaque-induced periodontal diseases are generally classified destructive or non-destructive. Clinical attachment loss is a sign of destructive (physiologically irreversible) periodontal disease. The quality of the epithelial layers define the extent and progression of periodontal disease.

The barrier function of the epithelial layers helps prevent and retard periodontal disease. Repeated use of botulinum toxin by topical application, regional injection can cause a tighter seal from augmentation of cell to cell adhesion protecting the quality of bone loss and PDL integrity. In gingivitis, inflammation localized to the supracrestal region of the periodontium leads to ulceration of the junctional epithelium. Although this is technically a loss of clinical attachment, the term clinical attachment loss is used almost exclusively to refer to connective tissue attachment loss. Use of repeated botulinum injections can result in prevention and therapy of ulceration, epithelial erosion, with subsequent loss of PDL integrity, connective tissue attachment and loss of bone.

Example 1—Exudative (Wet) Macular Degeneration not Responsive to Conventional Therapy A 71 year old man was diagnosed with progressive macular degeneration with substantial sub retinal and sub foveal fluid, which was unresponsive to repeated Avastin® intra-vitreal injections and Eylea Intra vitreal injections (10 injections)(FIG. 9A-9E). Patient was treated with 100 units of per-ocular botulinum toxin type A (BOTOX®) in forehead, orbicularis and deep temporal fossa which resulted in a substantially augmented response to an anti-VEGF agent on subsequent injection with substantial resolution of sub foveal fluid (see FIG. 9A-9E).

The patient noted his vision was augmented after the combination of anti-VEGF and botulinum formula than the prior unsuccessful Anti-VEGF therapy. The interpretation was that the botulinum toxin given before the next anti-VEGF enhanced the response and converted this patient wet macular degeneration to a dry state (due to the antecedent botulinum toxin injections).

Anatomic improvement in this patient included flattening of the retina as documented with ocular coherence tomography, decrease in sub-retinal and intra retinal fluid, decreased choroidal neovascular membrane, and thickening of the RPE (FIG. 9F). These anatomic findings are typical for positive response to exudative (WET) age related macular degeneration.

Example 2—Non-Exudative Macular Degeneration (Dry Macular Degeneration)

The results of this example are shown in FIGS. 10A and 10B. Elderly female with well-documented non-exudative macular degeneration in each eye and about 20/40 vision in each right and left eye receives botulinum injection comprising about a total of 100 unit to head, per-orbital region and an area into the pterygopalatine fossa targeting the autonomic and sensory ganglionic structures in this region. The patient notices slow improvement in contrast sensitivity and clarity of vision, which lasted about three months. She desired another injection with the type A botulinum toxin (BOTOX-A®, Allergan) in order to maintain vision. On ophthalmologic exam no other reasons for the subjective improvement in vision could be established on pre-injection and post injection examinations.

Optical coherence tomography indicates flattening and regression of drusen bodies as well as increased surface regularity of the retinal pigment epithelium (FIG. 10). Findings were concomitant with subjective visual improvement.

Without wishing to be bound by theory it is believed that the injections in peri orbital nervous structures allowed for axoplasmic transport into the eye improving functioning of the retinal pigment epithelium function and possibly structure allowing improved vision.

Example 3—Filamentary Keratitis (Improvement of Corneal Epithelial Integrity and Adhesion Based on Direct Surface Examination of an Epithelial Sheet)

A 71-year-old man was treated for blepharospasm for 10 years. He noted improvement after injections ranging from 40-80 units. Concomitantly, he was diagnosed to have filamentary keratitis. After botulinum administration by drop form (20 units) and by injection into lids, the filaments disappeared or were markedly improved associated with decreased light sensitivity, decreased pain, improved vision, and increased regularity of the epithelium, as demonstrated by computerized reflective corneal topography. The increased adhesiveness of the epithelium resulted in improvement in his corneal surface with improved vision, reduced surface distortion and lessened pain with concomitant resolution of detached filaments.

Example 4

An 82-year-old woman with long standing stage 1 macular degeneration had been followed for stage 1 macular degeneration for about 4 years. She noted some decrease in vision in the left eye over one year. OCT (Zeiss) showed accumulation of intra-retinal fluid over degenerated retinal pigment epithelium as a change from a previous scan (see FIGS. 11A-11D). Previous scan showed dry degeneration with irregularity in sheet configuration of the RPE with evidence of RPE discontinuity and breakup with neural retinal RPE migration (focal hyper reflective lesions moving into neuroretina) (FIG. 11A).

Injection of botulinum toxin after advice to patient of side effects was made using 70 units under the temporal muscle in several locations and in peri-orbital region (multiple dose injection). Region of the pterygopalatine fossa was also targeted for diffusion effect. FIG. 11B shows peri-foveal leakage with conversion of the macular degeneration to wet variety.

The plan for treatment with Avastin® or Eylea® was made within 2 weeks. Sub muscular injection toward the pterygopalatine fossa was made with 70 IU of botulinum toxin type A. Repeat OCT san after 10 days showed no resolution of fluid (FIG. 11C). After 14 days there was complete resolution of the fluid (see FIG. 11D).

This case demonstrated the tempo of effect required about 14 days consistent with a delay expected with axoplasmic flow. This case demonstrated converting stage 2 macular degeneration (wet variety) to stage 1. No intra ocular injection with Eylea® or Avastin® was necessary and intra-ocular injections were aborted. The patient was referred for continued monitoring.

Example 5

Figure 12A:
FIGS. 12A-12C illustrate OCT images obtained from a patient treated with the disclosed therapeutic formulations, according to the disclosed methods.

An 87-year-old woman with 20 years of hem-facial spasm. She developed dry macular degeneration 4 years prior. About 2 years after she converted to wet degeneration with leaks into the sub retinal space and neuro-retina, several injections of Avastin® resulted in drying of the neuroretina with improvement in vision. She remained stable for about two years when a routine OCT exam revealed re-accumulation of fluid in the peri foveal region. A botulinum toxin injection was given for her hemi facial spasm in doses routine for this condition. Additionally, a deep injection of 20-30 unit was directed toward the pterygopalatine fossa directed at nerve ganglion. Her pre-injection photo is shown in FIG. 12A.

Figure 12B:
Figure 12C:
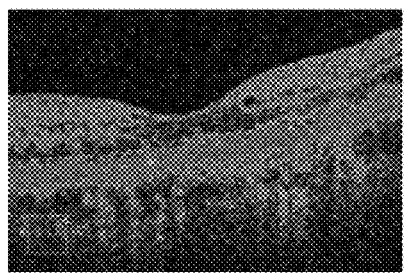
Figure 14C:
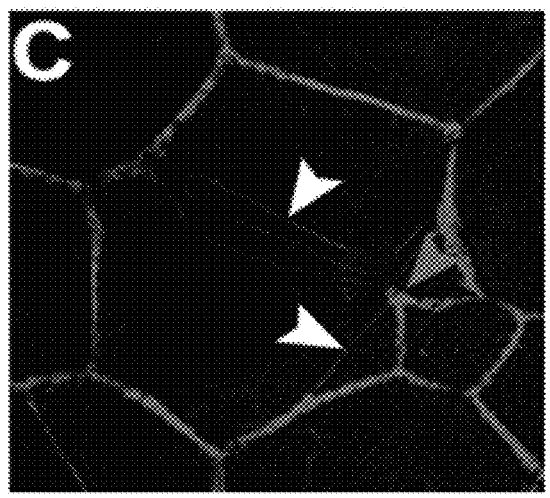
Figure 14D:
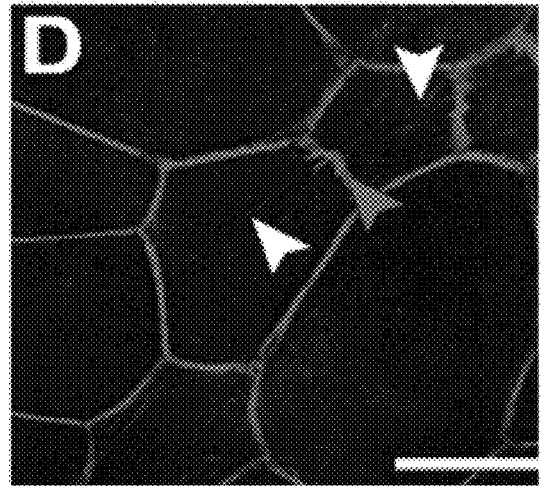

After two weeks improvement in perifoveal fluid was noted to occur (FIG. 12B). Vision improved in the left eye from 20/40 to 20/25. Note the fluid accumulation on both sides of the fovea is substantial mitigated after two weeks. Further, increase structural regularity (surface smoothness of RPE is enhanced, black and white, and external limiting membrane and IS-OS interface are more defined). At 10 weeks, know duration end for botulinum toxin and fluid accumulation begins to recur. Repeat injections after re accumulation of fluid in 10 weeks resulted in a second cycle response with complete resolution of intra-retinal edema. Dosing injections were increased to 100 units.

Example 6—Macular Edema

A 90-year-old man with a 35-year history of type 2 diabetes presents with macular edema 5 years after cataract surgery. Micro aneurysms/leakage are documented in the macular by inspection and angiography. Macular edema is documented by OCT. 40 U of botulinum type A toxin is injected in region of pterygo palatine fossa outside the eye and eye socket. After 3 weeks there is complete resolution of macular edema. The experimental results of this example are provided in FIGS. 13A and 13B. In particular, FIG. 13A illustrates the macular edema prior to injection and FIG. 13B illustrates the macular edema symptom reduction visible 3 weeks after temporal injection toward the pterygo-palatine fossa (with spatial computer registration). Repeat injections are planned.

Example 7—Retrospective Review

After initial observation (Example 1), a retrospective review of several hundred records of general eye patients treated for types blepharospasm and cervical dystonia (treated with botulinum toxin), diseases in older age groups, was conducted for progressive age related macular degeneration. No patient had a macular degeneration progression while under repeated botulinum injections. The absence of this common problem in patients over the age of 60 was unusual and suggests cause effect with concomitant botulinum treatment. Dosing ranges for these patients was typically between 10 and 600 units.

Example 8—Central Vein Occlusion

An 84-year-old woman with central vein occlusion OD who, for other medical reasons, could not receive anti-VEGF therapy for a period of 5 months, presented with extreme macular edema and hand motions vision. 50 Units of botulinum toxin was injected on the involved side. After 2 weeks the macular edema was reduced by 60-70% on SD OCT with some visual improvement (CF 3 ft) in the involved eye. Repeat dosing of 100 units was given to the patient. Vision slowly improved to 20/800 in the involved eye. Botulinum toxin with anti-VEGF (Avastin™) improved to 20/100.

An added extended botulinum toxin injection in para-orbital regions maintained the macular with CRVO-related edema for a period of 10 months without recurrence. This example case indicated additive effects of botulinum toxin with respect to potency and duration of action of conventional therapy with Avastin™.

Example 9

Figure 15A:
FIGS. 15A and 15B illustrate OCT-A images obtained from a patient treated according to the disclosed methods.
Figure 15B:
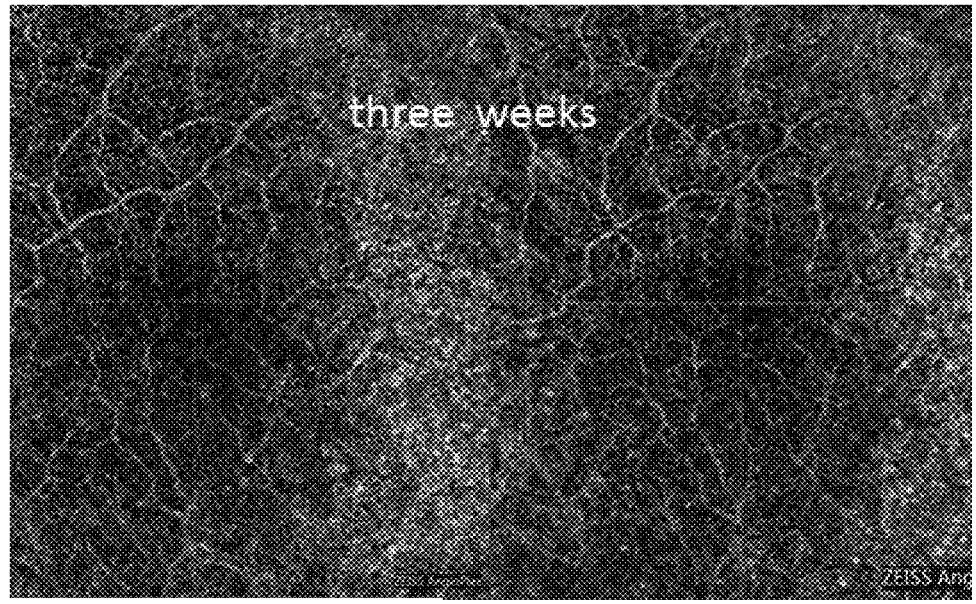

An 86-year-old light skin male presented with evidence of early drusen in both macular regions and notices a small decline in vision to 20/30 (minus 2) OD and 30/30 (minus 1) OS. OCT-A images of the patient's eyes after treatment are shown in FIGS. 15A and 15B (FIG. 15A illustrates the left eye and FIG. 15B illustrates the right eye). The OCT-A images shown in FIGS. 15A and 15B were obtained using a Spectral domain (5000 Zeiss) and show sub-foveal choriocapillaris and defective flow in sub foveal choriocapillaris in both eyes. This patient received botulinum toxin injections into the para orbital region directed into the pterygopalatine fossa at a single dose of 25 units (BOTOX® units) on each side. After the botulinum toxin injections, the patient experienced an improvement in vision in both eyes.

FIGS. 15A and 15B show increased capillary flow (choroidal blood flow) under the fovea after three weeks on both the right and left side. Note the increase in density of the signal and the fill in of the choriocapillaris.

Example 10

An 83-year-old woman presented with peri foveal geographic atrophy in the left eye and moderate dry macular degeneration in the right eye. After an injection of 60 units on the left side (with severe geographic atrophy) and an injection of 15 units on the right side (moderate dry AMD) she experienced the following changes in vision: the side with peri foveal geographic atrophy has clearer vision around the blind spot than previously. She described the vision around the corresponding scotoma (blind spot) was even better than the right eye. Without wishing to be bound by theory, the difference in botulinum toxin dose provided to the respective eyes may have affected the type of results experienced. In other words, the dose of 60 units may have a greater effect on the patient than the dose of 15 units.

Figure 16:
FIG. 16 illustrates an OCT-A image obtained from a patient treated according to the disclosed methods.

A photograph of the patient's eye obtained using OCT-A techniques three weeks after treatment is shown in FIG. 16. FIG. 16 shows improvement in the choroidal choriocapillaris perfusion. In particular, the increase in flow denoted by contrast within the peri foveal region in the choroid and the increase in choriocapillaris signal in the region can be seen in FIG. 16.

Example 11

An 81-year-old man with a history of exudative macular degeneration for past six years was treated as follows.

Repetitive Avastin™ injections were given in both eyes which resulted in a dry macula state for 4 years with visual acuity of better than 40/40 OD, 20/40 OS. A focal area "T" with fluid accumulation occurred over the past two years which slowly increased in size. The cyst was located in the peri foveal, which seemed to start causing a decrease in vision in the left eye.

Figure 17A:
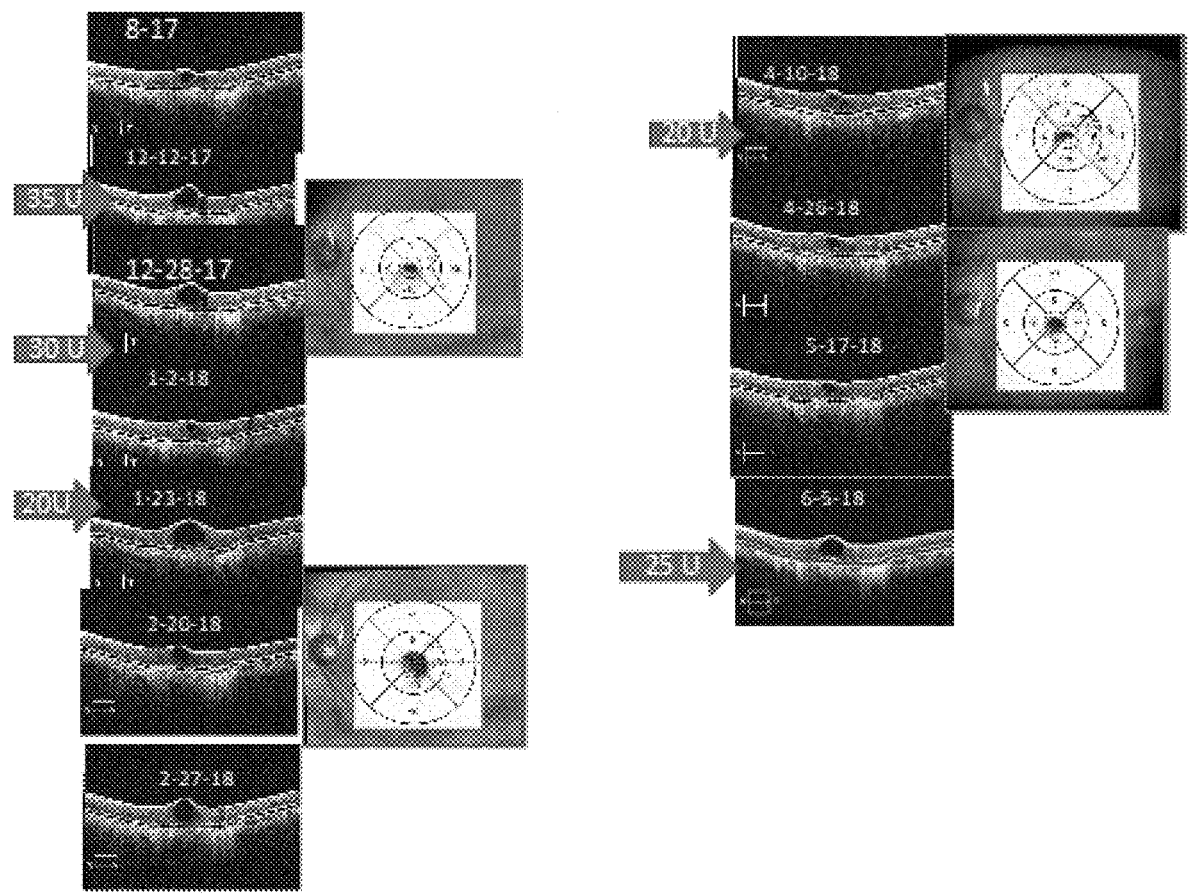
FIG. 17A illustrates numerous OCT-A images obtained from a patient treated according to the disclosed methods.

An injection of botulinum toxin directed into the pterygopalatine fossa was administered on both sides after informed consent was provided. After treatment, the patient's vision improved in both eyes. The focal fluid in the left eye shrunk after three weeks (see FIG. 17A). The cyst slowly recurred after 8 weeks. Another trial injection was made not involving conjunctival, or orbit regions. The cyst again shrunk for about 8 weeks. Another trial of botulinum A toxin was injected into the para orbital region again causing shrinkage of the cyst. OCT-A images demonstrated improvement in blood flow after the pterygopalatine injections.

Figure 17B:
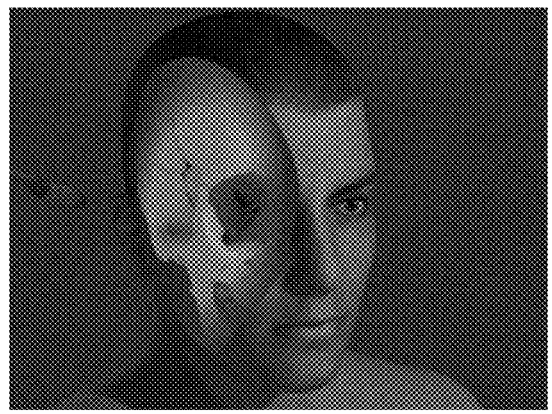
FIG. 17B illustrates an exemplary pteryo palatine injection, in accordance with some embodiments of the subject disclosure. The images shown in FIGS. 15A, 15B, 16, 17A, and 17B illustrate increased blood perfusion based on red blood cell movement in the parafoveal region.

Note that this case demonstrated an improvement in perifoveal fluid accumulation with repeated effectiveness. Further, the duration of effect was consistent with the known duration of effect of botulinum type A toxin on multiple cycles, thus adding to the credibility and reproducibility of the observations. The patient noted improvement in vision from 20/40 to 20/25 coincident with the structural improvement in the fovea in his left eye. Further blood flow improvement was demonstrated using OCT-A in the region of the foveal fluid, demonstrating an increased clearance at least in part effected by the uveal scleral pump improvement provided by botulinum toxin. In particular, the botulinum toxin injected appears to have induced an increase in blood flow (see FIG. 17A). That is, greater flow appears to have caused an increase in fluid clearance from the neuro-retina. FIG. 17B illustrates an exemplary pterygopalatine injection.

Example 12

A 73-year-old man presented with a history of high myopia, lattice retinal dystrophy, a history of retinal detachment, and dislocated IOL due to zonular dehiscence. The patient may also have Marfans syndrome. An anterior chamber lens was implanted with subsequent development of macular edema associated with epiretinal membrane formation. The patient refused intraocular injections of Eylea and was alternatively given para-orbital injections of botulinum toxin. Topical steroid failed to improve the macular edema. Steroids and botulinum toxin administered via para-orbital injections produced substantial improvement in the macular edema (see FIG. 18A). Further, increased blood flow to the choroid was demonstrated 2 weeks after paraorbital botulinum toxin was injected (see FIG. 18B). Note that the effectiveness of the uveal scleral pump was used to dry the macula in this complex case by para orbital injections.

Figure 18D:
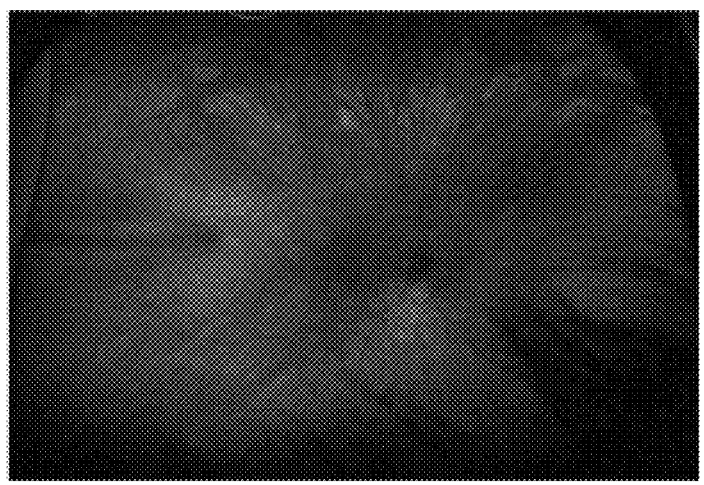
FIG. 18D illustrates an image showing features of an exemplary patient's eye, in accordance with some embodiments of the subject disclosure.

FIG. 18C illustrates an exemplary uveal sclera pump in which the choroid acts as a flow generated suction pump bringing fluids out of the eye. The integrity of the Bruch's membrane and retinal pigment epithelial barrier is dependent on the pump. A defect in pumping contributes greatly to macular degeneration. Note the circular orientation of the choroidal vortex venous system shown in FIG. 18C in an addition orientation to increase flow dynamic in the choroid under the RPE. Defects in the RPE and Bruch's membrane can cause leaks in the pumping system, leading to fluid accumulation. FIG. 18D is an image showing features of an exemplary eye.

Selected Example Embodiments

In some embodiments, a method of preventing and slowing the development of macular degeneration is provided. In some such embodiments, the method comprises administering a formulation comprising botulinum neurotoxin, a fragment thereof, and/or a neurotoxin associated protein to a human or mammalian patient suffering from or at risk for losing vision from macular degeneration. In these and other embodiments, the botulinum neurotoxin, fragment thereof, and/or neurotoxin associated protein is selected from the group consisting of: botulinum toxin A1-A5, B, C1-3, D, E, F, G and H.

In another example embodiment, a method of enhancing activity of anti-VEGF injectable agents is provided. In some such embodiments, the method comprises administering a formulation comprising a botulinum neurotoxin, a fragment thereof, and/or a neurotoxin associated protein to a patient suffering from exudative forms of macular degeneration, wherein the formulation is administered to the patient via intra-ocular injection or extra ocular injection and administering an anti-VEGF agent to the patient. In select embodiments, the formulation comprises a fusion protein containing botulinum neurotoxin or a fragment thereof and the anti-VEGF agent. In these and other embodiments, the formulation is administered to the patient separately from the anti-VEGF agent. In certain cases, the anti-VEGF agent is selected from the group consisting of: a ranibizumab, a bevacizumab, and an aflibercept.

In other embodiments, a method of diminishing progressive visual loss from retinitis pigmentosa is provided. The method may comprise, in some cases, administering a formulation comprising a botulinum toxin or a fragment thereof to a patient suffering from retinitis pigmentosa, wherein the formulation is administered to the patient via intra-ocular injection or extra ocular injection.

In other embodiments, a method of diminishing visual loss from diabetic macular edema from diabetes, central or branch vein occlusion, degenerative retinal disease, retinitis pigmentosa (RP) retinal disease, or uveitis is disclosed. The method may include, in some cases, administering a formulation comprising a botulinum toxin or a fragment thereof to a patient suffering from macular edema from diabetes, branch vein occlusion or uveitis, wherein the formulation is administered to the patient via intra-ocular injection or extra ocular injection.

In select embodiments, a method of preventing age-related macular degeneration in a patient is described. The method may include administering a formulation comprising a botulinum toxin or a fragment thereof to the patient, wherein the formulation is administered to the patient via intra-ocular injection or extra ocular injection. In these and other embodiments, the patient may be at risk for macular degeneration as determined by medical history or genetic evaluation.

A method of treating periodontal disease and tooth loss in a patient is also described herein. The disclosed method includes administering a formulation comprising a botulinum toxin or a fragment thereof to the patient, wherein the formulation is injected or topically applied to gingiva, peripheral nerves, oral mucosa, or skin in a facial or peri-oral region.

In another example embodiment, a method of treating chronic nephrotic syndrome in a patient is described. The disclosed method includes administering a formulation comprising a botulinum toxin or a fragment thereof to the patient, wherein the formulation is injected or topically applied to a kidney or surrounding regions, including one or more nerves entering the kidney. Numerous other example embodiments will be apparent to those skilled in the art upon consideration of the subject disclosure.

Definitions and Abbreviations

Unless otherwise defined herein, the following terms have the stated definitions.

AMD—age related macular degeneration.

VEGF—vascular endothelial growth factor. VEGF binds to two members of a receptor tyrosine kinase family, VEGF receptor (VEGFR)-1 and VEGFR-2. VEGFR-2 is considered the main VEGF receptor and mediates the proliferative effects of VEGF on vascular endothelial cells. VEGF binding to VEGFR-2 induces the dimerization and subsequent autophosphorylation of receptors by intracellular kinase domains, which leads to a mitogenic and proliferative signal. VEGF-C and VEGF-D bind to VEGFR-3, another member of this family of receptor tyrosine kinases.

Botulinum toxin—any immunotype, fraction of botulinum, subtype, derived from *C botulinum* species by fermentation or genetic expression in recombinant system.

HA—hemagglutinin derived from production of Clostridia botulinum in fermentation or other natural process, or recombinant, or any other expression systems (accessory protein).

RPE—retinal pigment epithelium in a mammal. HA is also a botulinum accessory protein.

OCT—Spectral domain, or any other version or enhancement of ocular coherence tomography. OCT angiography (OCT-A) is a type of OCT imaging technique. Specifically, OCT-A is an imaging technique in which imaging of red blood cell movement in the retinal and choroidal vessels occurs, reflecting blood flow and blood flow rates.

NHNT—Non-neurotoxin, non-hemagglutinin protein produced by fermentation of *C botulinum* or by recombinant production. NHNT is also an accessory protein.

Anti-VEGF—any known VEGF monoclonal or fusion protein, or VEGF agent which suppresses angiogenesis and/or leakage. Anti-VEGF terms used herein refers to an agent which recognized multiple isoforms of VEGF. Agents may include pieces of the VEGF receptors or entire receptor structures.

Complement protein—any complement factor involved in complement activation cascade.

Injection—administration of botulinum toxin (and other compounds, if applicable) with any form of a needed or microneedle.

Blepharospasm—condition treated with peri-ocular administration of botulinum toxin (commonly with a dosing range of between 10 and 300 units).

Neuropeptide—any know neuropeptide including but not limited to Substance P, CGRP, VIP.

ELM—external limiting membrane of the retina.

IS/OS—line defining the inner and outer segments of photoreceptors.

Stress fiber—condensation of contractile actin and associated proteins which distorts cell membranes and disrupted barrier effect in a given tissue or epithelial layer.

CRVO—central retinal veins occlusion.

BRVO—branch retinal vein occlusion.

nAMD—stage 2, 3 AMD with neovascularization (active angiogenesis stages with leakage).

Biologic barrier—any biologic barrier depending on cell to cell adhesion and cell to basement membrane adhesion to maintain tissue function.

mRNA—messenger RNA.

Conventional dosing—any FDA-approved dosing of botulinum toxin for an indication of the head or neck.

Formulation—as used herein, the term 'formulation' refers to a composition of one or more biologic agents with or without excipient present.

Fusion protein—addition of one or more proteins produced industrially for the purpose of preserving the biologic activity of each protein to enhance the utility of the composition. Generally, the fusion protein represents ligated genes or gene fragments fusion and expressed in appropriate cell system often using PCR to enhance quantity of the genes present for the expression system.

Macromolecule—a large molecule having a relatively large molecular weight, such as a nucleic acid, protein, carbohydrate, or lipid.

Activity—the term "activity" refers to the specific activity or biologic activity of a given compound as measured using conventional, industry-accepted methods. The activity of a compound is used to quantify purity or concentration and is calculated as units per mass.

Rho—Rho family GTPase.

Ras—related C3 botulinum toxin substrate maintaining epithelial differentiation, cytoskeletal reorganization, cell growth.

Ras 2—protein involved in cyto skeletal reorganization.

Ras 3—protein involved in intercellular signaling pathways.

ROCK1—protein kinase regulator of actomycin cytoskeleton promotes contractile force generation, important in angiogenesis, cell motility. Major downstream effector of RhoA.

IU—Botulinum LD 50 for 20-30 gm Swiss Webster mouse, "Mouse unit."

HcA—Fragment of botulinum type A heavy chain serving as binding domain to nerve cells.

SNAP-25—Synaptosomal-associated protein 25 is a component of the trans-SNARE complex, which is proposed to account for the specificity of membrane fusion and to directly execute fusion by forming a tight complex that brings the synaptic vesicle and plasma membranes together. Substrate for L chain botulinum activity.

Regular hexagon—six-sided closed figure with equal sides.

Ophthalmologist—A medical doctor trained to treat medical and surgical diseases of the eye. Duties include injecting the globe and periocular region.

EMT—epithelium mesenchymal cell transformation.

GA—geographic atrophy (end stage form of dry AMD).

RPE atrophy—shrinking, flattening and loss of vital physiology of the retinal pigment epithelium.

CNV—choroidal angiogenesis (neovascularization protein to leak fluid and hemorrhage. Occurs under the RPE, under retina and intra neuroretina.

Leakage—abnormal and pathological movement of fluid through a biologic barriers into intra-ocular structures. The term "leakage" is used herein to refer to fluid accumulation in the neuroretina, subretina space, or choroid (sub RPE). Such leakage is commonly associated with distortion of vision and obstruction of photoreceptors.

Uveoscleral pump—a pumping mechanism generated by blood flow into the choriocapillaris, which produces a low-pressure cell in the region of the internal choroid, thereby providing pressure for the attachment of RPE to Bruch's membrane, suction force removing waste metabolites from the neuroretina and internal eye, and a mechanism for removal of physiologic fluid in the neuro-retina as well pathologic edema in disease states. The pump keeps the alignment of RPE cells maintaining barrier function, facilitating RPE phagocytosis, and treating pathological edema. Defects in the pumping mechanism may be related in cause to early and late stages of macular degeneration.

Laser Doppler technique—another method of determining choroidal blood flow.

Geographic atrophy—atrophy of the retinal pigment epithelium with drop out or degeneration of cellular structure and destruction of the rods and cones in close opposition to the apex of the RPE. This process is most commonly seen in dry forms of macular degeneration but can co-exist with exudative wet forms of macular degeneration. Halting the progression of geographic atrophy is a targeted endpoint for measuring agents effective in treating dry macular degeneration.

The invention claimed is:

1. A method of treating or slowing the development of macular degeneration in a patient, the method comprising:
   identifying a patient with macular degeneration with evidence of choroidal blood flow reduction in a choriocapillaris or a choroid of the patient; and
   injecting a botulinum neurotoxin into the periorbital or para orbital region of the patient, but not into an intra-ocular or a subconjunctival region of the patient to increase choroidal blood flow, wherein the botulinum neurotoxin is botulinum neurotoxin type A,
   wherein the botulinum neurotoxin is transported by axoplasmic flow into the intra-ocular region of the patient by a nerve fiber conduit and the axoplasmic flow does not subject extra-ocular muscles of the patient to weakening effects of botulinum neurotoxin,
   wherein injecting the botulinum neurotoxin avoids diplopia and/or ptosis by accessing the choroid and retina by axoplasmic transport,
   wherein injecting the botulinum neurotoxin avoids risk of retinal detachment endophthalmitis, cataract formation, vitreous hemorrhage, retinal break, and glaucoma, and
   wherein the botulinum neurotoxin injected conforms with conventional dosing and preserves or improves vision of the patient.

2. The method of claim 1 further comprising measuring choroidal blood flow of the patient using Ocular Coherence Tomography with Angiographic capability (OCT-A).

3. The method of claim 2, wherein choroidal blood flow includes blood flow in the choriocapillaris.

4. The method of claim 1, wherein injecting the botulinum neurotoxin improves uveoscleral pumping on a level of Bruch's membrane and retinal pigment epithelium.

5. The method of claim 1, wherein injecting the botulinum neurotoxin aligns the patient's retinal pigment epithelium and sustains barrier function of the retinal pigment epithelium.

6. The method of claim 1, wherein injecting the botulinum neurotoxin sustains integrity of the patient's Bruch's membrane.

7. The method of claim 1, wherein the macular degeneration is non-exudative or dry macular degeneration.

8. The method of claim 7, wherein the dry macular degeneration includes macular degeneration with geographic atrophy and compromised choroidal blood flow.

9. The method of claim 1, wherein the macular degeneration is exudative or wet macular degeneration.

10. The method of claim 1, where the botulinum neurotoxin is injected into the patient using a pterygopalatine ganglion target in a para orbital region.

11. The method of claim 1, wherein the conventional dosing ranges between 5-400 units.

12. The method of claim 1 further comprising one or more repeated injections of botulinum neurotoxin into the patient.

13. Method of claim 1 further comprising measuring blood flow of the patient using a laser Doppler technique.

14. The method of claim 1, wherein injecting the botulinum neurotoxin results in a reduction in rate of drusen formation, atrophic geographic atrophy, pigment migration, leakage or choroidal neovascularization, or retinal hemorrhage.

15. The method of claim 1, wherein the patient identified for treatment was previously treated with an anti-VEGF agent and exhibited vaso-occlusive properties, wherein the patient also has evidence of decreased blood flow in the choriocapillaris, and wherein injecting the botulinum neurotoxin slows or stops the development of dry macular degeneration.

16. The method of claim 15, wherein the slowing or stopping development of dry macular degeneration is characterized by observed drusen, drusenoids, geographic atrophy, hyper-reflective foci migration into the neuro-retina, and photo receptor atrophy.

17. The method of claim 15, wherein the method results in improved vision for the patient as measured by acuity, visual field, contrast sensitivity, and/or color vision.

18. The method of claim 1, wherein the patient presents with central serous retinopathy.

* * * * *